United States Patent
Gu et al.

(10) Patent No.: US 11,865,178 B2
(45) Date of Patent: Jan. 9, 2024

(54) DERMAL APPLICATOR FOR USE IN CANCER PHOTOIMMUNOTHERAPY

(71) Applicant: North Carolina State University, Raleigh, NC (US)

(72) Inventors: Zhen Gu, Raleigh, NC (US); Yanqi Ye, Raleigh, NC (US)

(73) Assignee: North Carolina State University, Raleigh, NC (US)

(*) Notice: Subject to any disclaimer, the term of this patent is extended or adjusted under 35 U.S.C. 154(b) by 927 days.

(21) Appl. No.: 16/759,035

(22) PCT Filed: Oct. 25, 2018

(86) PCT No.: PCT/US2018/057494
§ 371 (c)(1),
(2) Date: Apr. 24, 2020

(87) PCT Pub. No.: WO2019/084259
PCT Pub. Date: May 2, 2019

(65) Prior Publication Data
US 2021/0177968 A1 Jun. 17, 2021

Related U.S. Application Data

(60) Provisional application No. 62/576,774, filed on Oct. 25, 2017.

(51) Int. Cl.
| | |
|---|---|
| A61K 41/00 | (2020.01) |
| A61P 35/00 | (2006.01) |
| A61K 39/00 | (2006.01) |
| A61K 9/00 | (2006.01) |
| A61K 31/407 | (2006.01) |
| A61K 38/19 | (2006.01) |
| A61K 45/06 | (2006.01) |
| A61K 47/36 | (2006.01) |
| A61N 5/06 | (2006.01) |
| A61N 5/067 | (2006.01) |

(52) U.S. Cl.
CPC ........ A61K 41/0057 (2013.01); A61K 9/0021 (2013.01); A61K 31/407 (2013.01); A61K 38/193 (2013.01); A61K 39/0011 (2013.01); A61K 39/00119 (2018.08); A61K 45/06 (2013.01); A61K 47/36 (2013.01); A61N 5/062 (2013.01); A61P 35/00 (2018.01); A61N 5/067 (2021.08); *A61N 2005/0659* (2013.01)

(58) Field of Classification Search
CPC ............ A61N 2005/0659; A61N 5/062; A61K 41/0057; A61K 39/00; A61K 39/385; A61K 39/39; A61P 35/00; A61P 35/02; A61P 35/04; A61M 2037/0046
See application file for complete search history.

(56) References Cited

U.S. PATENT DOCUMENTS

| | | | |
|---|---|---|---|
| 2014/0140959 A1 | 5/2014 | Szalay et al. | |
| 2016/0136407 A1 | 5/2016 | Falo, Jr. et al. | |
| 2017/0157036 A1 | 6/2017 | D'Souza | |
| 2017/0202939 A1 | 7/2017 | Carreno et al. | |
| 2018/0311486 A1* | 11/2018 | Park ................. | A61M 37/0015 |
| 2018/0333483 A1 | 11/2018 | Carpentier et al. | |

FOREIGN PATENT DOCUMENTS

| | | | |
|---|---|---|---|
| CN | 104645331 A | 5/2015 | |
| CN | 104936612 A | 9/2015 | |
| WO | 2013033496 A2 | 3/2013 | |
| WO | 2017089529 A1 | 6/2017 | |
| WO | WO-2017094996 A1 * | 6/2017 | ............. A61K 47/36 |
| WO | 2017151727 A1 | 9/2017 | |

OTHER PUBLICATIONS

Joshi et al (PLOS One 2012, vol. 7, No. 2, e32067, 12 pages) (Year: 2012).*
Dees et al (Photochemistry and Photobiology, 2002, vol. 75, pp. 296-301) (Year: 2002).*
Lee et al (Journal of Photochemistry & Photobiology, 2016, vol. 155, p. 98-103). (Year: 2016).*
Al-Zahrani et al (Expert opinion on Drug Delivery, 2012, vol. 9, pp. 541-550) (Year: 2012).*
Joshi et al (Expert Review of Vaccines, 2014, vol. 13, pp. 9-15) (Year: 2014).*
Prasa et al (Nanomeeicine, Nanotechnology, Biology and Medicine, 2011, vol. 7, pp. 1-10) (Year: 2011).*
Kulkarni et al (Clinical Cancer Research, Sep. 14, 2017, vol. 23, pp. 5631-5638) (Year: 2017).*
European Patent Office Extended Search Report for Application No. 18871610 dated Jul. 15, 2021 (10 pages).
Carpentier et al., "Synthetic melanin bound to subunit vaccine antigens significantly enhances CD8+T-cell responses", PLOS One, 2017, pp. 1-14.
Ye et al., "A melanin-mediated cancer immunotherapy patch", Science Immunology, vol. 2, 2017, pp. 1-12.
Kim, M., et al. "Thermohydrogel containing melanin for photothermal cancer therapy." Macromolecular bioscience 17.5 (2017).
Zaric, M., et al. "Skin dendritic cell targeting via microneedle arrays laden with antigen-encapsulated poly-D, L-lactide-co-glycolide nanoparticles induces efficient antitumor and antiviral immune responses." ACS nano 7.3 (2013): 2042-2055.
China Patent Office Action for application 201880068497.7, dated Nov. 2, 2022 (13 pages with translation).

(Continued)

*Primary Examiner* — Karen A. Canella
(74) *Attorney, Agent, or Firm* — Michael Best & Friedrich LLP

(57) ABSTRACT

Embodiments of the present disclosure relate generally to photoimmunotherapy for treating cancer. More particularly, the present disclosure provides photo-responsive dermal applicators that use transdermal microneedle arrays to administer an immunogenic composition and a photo-sensitive biological pigment to a subject to treat and/or prevent cancer. Photo-responsive dermal applicators of the present disclosure provide the ability to target cancerous tumors in a manner that is safer and less invasive than conventional means.

17 Claims, 39 Drawing Sheets

(56) References Cited

OTHER PUBLICATIONS

Japan Patent Office Action for application 2020-523318, dated Nov. 30, 2022 (6 pages with translation).
International Search Report and Written Opinion for Application No. PCT/US2018/057494 dated Feb. 22, 2019 (12 pages).
Ali et al., "In situ regulation of DC subsets and T cells mediates tumor regression in mice," Sci. Transl. Med., Nov. 2009, 1(8):8ra19.
Bachmann et al., "Vaccine delivery: a matter of size, geometry, kinetics and molecular patterns," Nat. Rev. Immunol. Nov. 2010, 10(11):787-796.
Banchereau et al., "Dendritic cells as therapeutic vaccines against cancer," Nat. Rev. Immunol., Apr. 2005, 5(4): 296-306.
Carrero et al., "Cancer immunotherapy. A dendritic cell vaccine increases the breadth and diversity of melanoma heoantigen specific T cells," Science, 2015, 348, 803-808.
Castle et al., "Exploiting the mutanome for tumor vaccination," Cancer Res., Mar. 2012, 72(5): 1081-1091.
Chen et al., "Photothermal therapy with immune-adjuvant nanoparticles together with checkpoint blockade for effective cancer immunotherapy," Nat. Commun., Oct. 2016, 7: 13193, 13 pages.
Cheng et al., "Functional Nanomaterials for Phototherapies of Cancer," Chem. Rev., Sep. 2014, 114(21):10869-10939.
Chiang et al., "Whole Tumor Antigen Vaccines: Where Are We?" Vaccines, 2015, 3(2):344-372.
Conde et al., "Local triple-combination therapy results in tumour regression and prevents recurrence in a colon cancer model," Nat. Mater., Oct. 2016, 15(10): 1128-1138.
Couzin-Frankel, "Cancer Immunotherapy," Science, Dec. 2013, 342(6165): 1432-1433.
Dankort et al., "BRafV600E cooperates with Pten loss to induce metastatic melanoma," Nat. Genet., May 2009, 41(5):544-552.
Dhodapkar et al., "Induction of Antigen-Specific Immunity with a Vaccine Targeting NY-ESO-1 to the Dendritic Cell Receptor DEC-205," Sci. Transl. Med., Apr. 2014, 6(2232): 232ra251.
Drake et al., "Breathing new life into immunotherapy: review of melanoma, lung and kidney cancer," Nat. Rev. Clin. Oncol., Jan. 2014, 11(1): 24-37.
Dudley et al., "Adoptive-cell-transfer therapy for the treatment of patients with cancer," Nat. Rev. Cancer, Sep. 2003, 3(9): 666-675.
Evans et al., "Fever and the thermal regulation of immunity: the immune system feels the heat," Nat. Rev. Immunol., Jun. 2015, 15(6): 335-349.
Fadel et al., "A carbon nanotube-polymer composite for T-cell therapy," Nat. Nanotechnol., Aug. 2014, 9(8): 639-47.
Filson et al., "Isolation of Melanin Granules," Nature, Jan. 1957, 179(4552): 211.
Fu et al., "Sting agonist formulated cancer vaccines can cure established tumors resistant to PD-1 blockade," Sci. Transl. Med., Apr. 2015, 7(283): 283ra252.
Garg et al., "Dendritic cell vaccines based on immunogenic cell death elicit danger signals and T cell-driven rejection of high-grade glioma," Sci. Transl. Med., Mar. 2016, 8(328): 328ra327.
Gu et al., "Biomaterials and emerging anticancer therapeutics: engineering the microenvironment," Nat. Rev. Cancer, Jan. 2016, 16(1): 56-66.
Hoffmann et al., "Co-potentiation of antigen recognition: A mechanism to boost weak T cell responses and provide Immunotherapy in vivo," Sci. Adv., Oct. 2015, 1(9): e1500415, 12 pages.
Holtzhausen et al., "Melanoma-Derived Wnt5a Promotes Local Dendritic-Cell Expression of IDO and Immunotolerance: Opportunities for Pharmacologic Enhancement of Immunotherapy," Cancer Immunol. Res., Sep. 2015, 3(9): 1082-1095.
Huang et al., "Active targeting of chemotherapy to disseminated tumors using nanoparticle-carrying T cells," Sci. Transl. Med., Jun. 2015, 7(291): 291ra294.
Irvine et al., "Engineering synthetic vaccines using cues from natural immunity," Nat. Mater., Oct. 2013, 12: 978-990.
Kim et al., "Injectable, spontaneously assembling, inorganic scaffolds modulate immune cells in vivo and increase vaccine efficacy," Nat. Biotechnol., Jan. 2015, 33(1): 64-72.
Kim et al., "The ABCs of artificial antigen presentation," Nat. Biotechnol., Apr. 2004, 22(4): 403-410.
Klevorn et al., "Adapting Cancer Immunotherapy Models for the Real World," Trends Immunol., Jun. 2016, 37(6): 354-363.
Kratky et al., "Direct activation of antigen-presenting cells is required for CD8+ T-cell priming and tumor vaccination," Proc. Natl. Acad. Sci. U.S.A., Oct. 2011, 108(42): 17414-17419.
Kupper et al., "Immune surveillance in the skin: mechanisms and clinical consequences," Nat. Rev. Immunol., Mar. 2004, 4(3): 211-222.
Lea, "Solubility of Melanins," Nature, Oct. 1952, 170(4330): 709.
Littman, "Releasing the Brakes on Cancer Immunotherapy," Cell, Sep. 2015, 162(6): 1186-1190.
Moraes et al., "Polymeric scaffolds for enhanced stability of melanin incorporated in liposomes," J. Colloid Interface Sci., Oct. 2010, 350(1): 268-274.
Murshid et al., "The Role of Heat Shock Proteins in Antigen Cross Presentation," Front. Immunol., 2012, 3:63, 10 pages.
Nagao et al., "Murine epidermal Langerhans cells and langerin-expressing dermal dendritic cells are unrelated and exhibit distinct functions," Proc. Natl. Acad. Sci. U.S.A., Mar. 2009, 106(9): 3312-3317.
Pardoll, "The blockade of immune checkpoints in cancer immunotherapy," Nature Reviews Cancer, Mar. 2012, 12: 252-264.
Ricklin et al., "Complement: a key system for immune surveillance and homeostasis," Nat. Immunol., Sep. 2010, 11(9): 785-797.
Rosenberg et al., "Adoptive cell transfer: a clinical path to effective cancer immunotherapy," Nat. Rev. Cancer, Apr. 2008, 8(4): 299-308.
Sato et al., "Spatially selective depletion of tumor-associated regulatory T cells with near-infrared photoimmunotherapy," Sci. Transl. Med., Aug. 2016, 8(352): 352ra110.
Stephan et al., "Biopolymer implants enhance the efficacy of adoptive T-cell therapy," Nat. Biotechnol., Jan. 2015, 33(1): 97-101.
Stephan et al., "Therapeutic cell engineering with surface-conjugated synthetic nanoparticles," Nat. Med., Sep. 2010, 16(9): 1035-1041.
Sulliivan et al., "Dissolving polymer microneedle patches for influenza vaccination," Nat. Med., Aug. 2010, 16(8): 915-920.
Sun et al., "Leveraging Physiology for Precision Drug Delivery," Physiol. Rev., Nov. 2016, 97: 189-225.
Swann et al., "Immune surveillance of tumors," J Clin. Invest., May 2007, 117(5): 1137-1146.
Wang et al., "Enhanced Cancer Immunotherapy by Microneedle Patch-Assisted Delivery of Anti-PD1 Antibody," Nano Letters, Apr. 2016, 16(4): 2334-2340.
Wang et al., "Tailoring Biomaterials for Cancer Immunotherapy: Emerging Trends and Future Outlook," Adv. Mater., Aug. 2017, 29(29): 1606036.
Yu et al., "Microneedle-array patches loaded with hypoxia-sensitive vesicles provide fast glucose-responsive insulin delivery," Proc. Natl. Acad. Sci. U.S.A., Jul. 2015, 112(27): 8260-8265.
Zhang et al., "Engineering Melanin Nanoparticles as an Efficient Drug-Delivery System for Imaging-Guided Chemotherapy," Adv. Mater., Sep. 2015, 27(34): 5063-5069.
Zhang et al., "Photoacoustic Drug Delivery," Sensors, Sep. 2017, 17(6): 1400.
European Patent Office Action for Application No. 18871610.4 dated Jun. 16, 2023 (5 pages).
Japanese Patent Office Action for Application No. 2020-523318 dated Jul. 27, 2023 (9 pages including English translation).

* cited by examiner

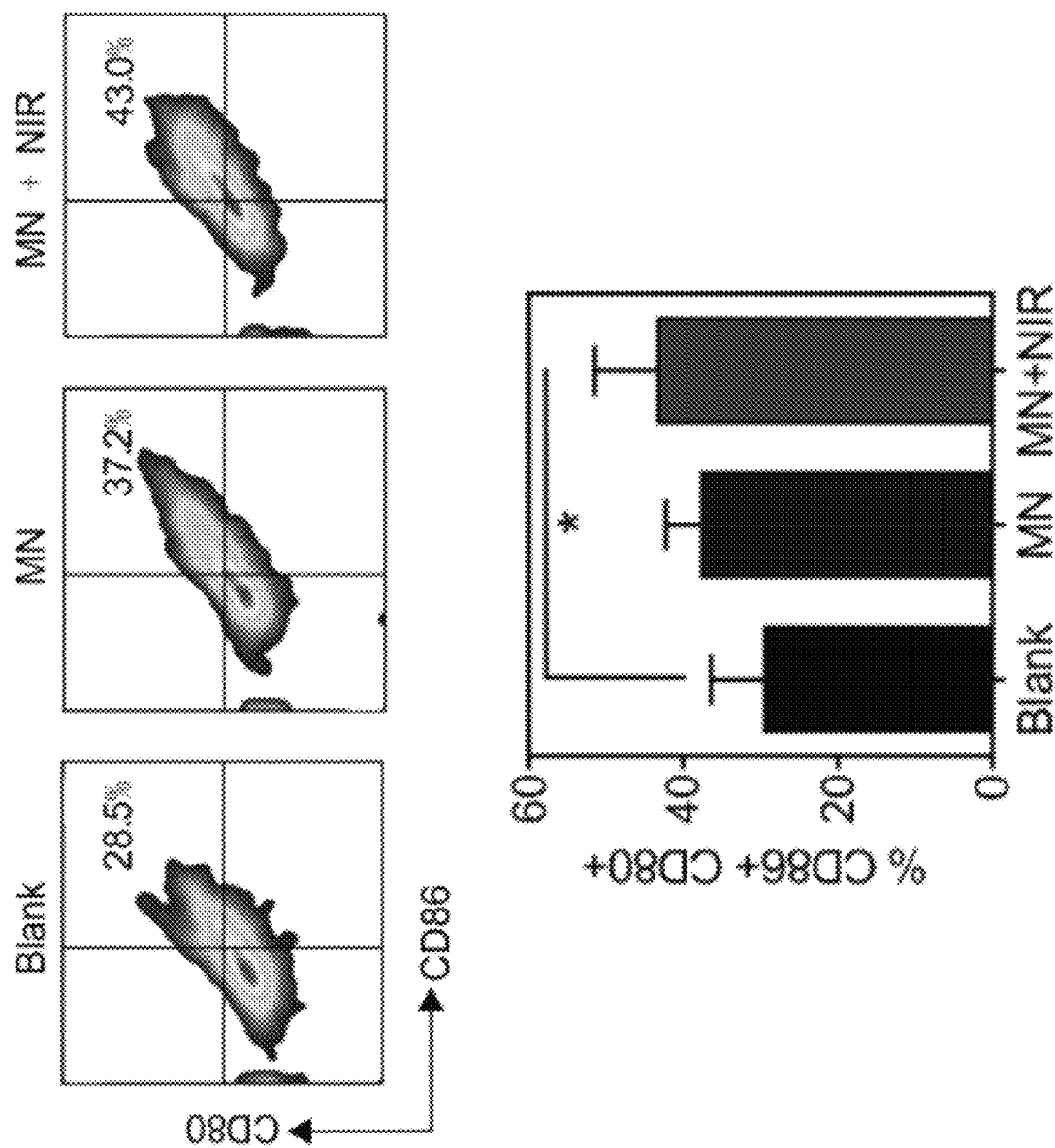

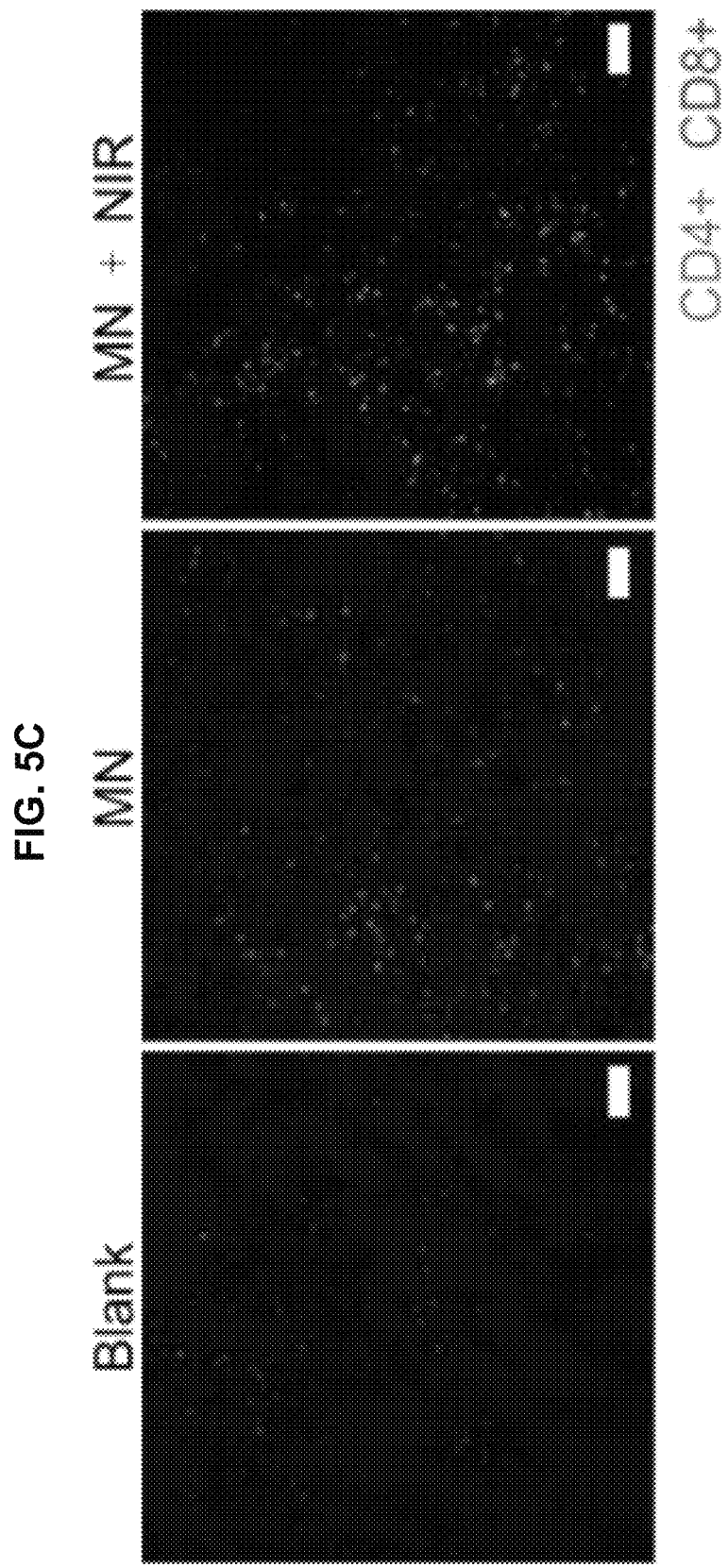

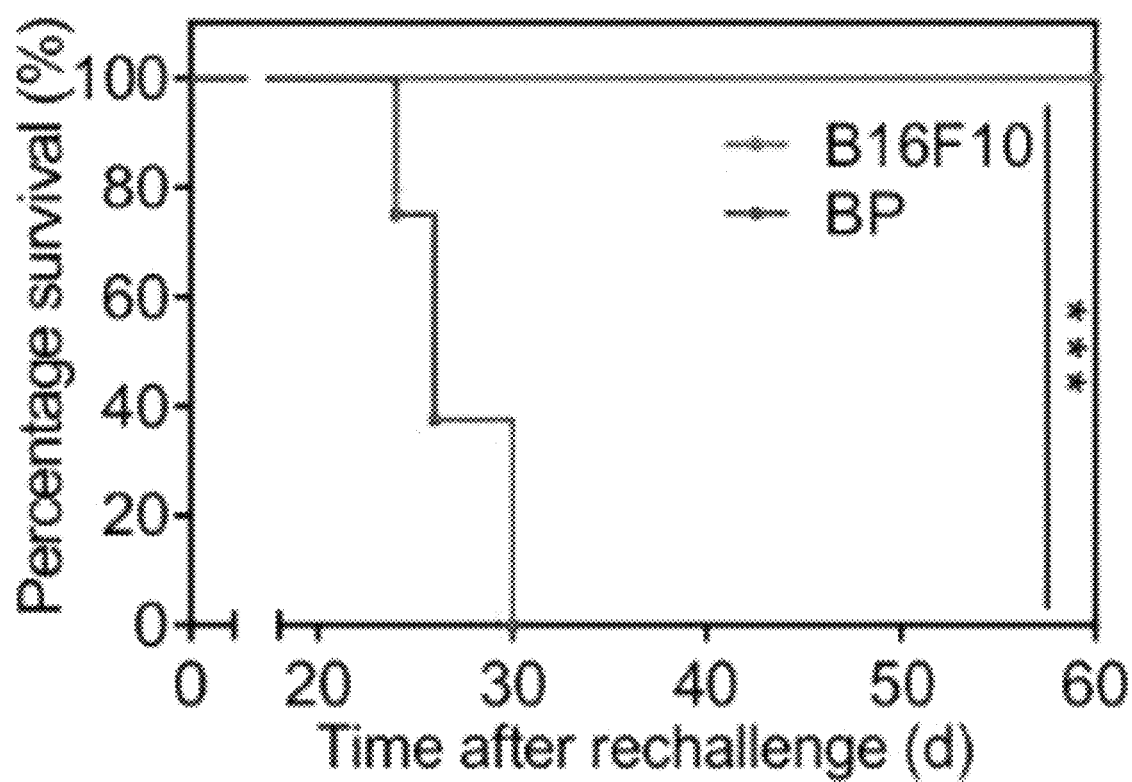

DERMAL APPLICATOR FOR USE IN CANCER PHOTOIMMUNOTHERAPY

CROSS REFERENCE TO RELATED APPLICATIONS

This application claims the benefit of U.S. Provisional Application No. 62/576,774, filed Oct. 25, 2017, which is incorporated herein by reference in their entirety.

GOVERNMENT FUNDING

This patent application is the U.S. national stage entry, under 35 U.S.C. § 371, of International Application Number PCT/US2018/057494, filed Oct. 25, 2018, which claims the benefit of U.S. Provisional Application No. 62/576,774, filed Oct. 25, 2017, the entire contents of each of which are hereby incorporated by reference.

FIELD

Embodiments of the present disclosure relate generally to photoimmunotherapy for treating cancer. More particularly, the present disclosure provides a photo-responsive dermal applicator that uses a transdermal microneedle (MN) array to administer an immunogenic composition and a photo-sensitive biological pigment to a subject to treat and/or prevent cancer.

BACKGROUND

Emerging technologies associated with immunotherapy hold tremendous promise in cancer therapy. Micro- or nanoformulations or engineered immune cells can be used to deliver a variety of immune modulators. Scaffolds, such as hydrogel, have also been developed to generate an immunogenic microenvironment that recruits and activates immune cells in situ. Moreover, T cell engineering that incorporates antibodies or therapeutics facilitates immune targeting and treatment. Among them, dendritic cell (DC)-based vaccination can effectively capture antigens to improve the effectiveness of the immune response and is a powerful tool for cancer therapy. However, engineering of DCs often involves complex and expensive ex vivo manipulation. In addition, the limited lymph-node homing capability of ex vivo manipulated DCs is at least in part responsible of the limited anticancer efficacy. Vaccination with whole tumor antigens provides a broad source of tumor-associated antigens that elicit significantly enhanced immune responses compared to narrowly-defined tumor antigens. Additionally, presenting a broad spectrum of immunogenic epitopes not only augments the immunity mediated by the DC antigen uptake and processing, but also directly activates CD4+T helper and CD8+ cytotoxic T lymphocytes (CTLs).

SUMMARY

Embodiments of the present disclosure relate generally to photoimmunotherapy for treating cancer. More particularly, the present disclosure provides a photo-responsive dermal applicator that uses a transdermal microneedle array to administer an immunogenic composition and a photo-sensitive biological pigment to a subject to treat and/or prevent cancer.

Embodiments of the present disclosure include a photo-responsive dermal applicator for use in photoimmunotherapy. In accordance with these embodiments, the dermal applicator includes a transdermal microneedle array comprising a plurality of microneedles, with each microneedle having a base portion and a tip portion, an immunogenic composition that includes at least one tumor antigen, and a photo-sensitive biological pigment.

In some embodiments, the immunogenic composition and the biological pigment are encapsulated within the microneedle array using a polymeric matrix, such as a hyaluronic acid-based matrix. The immunogenic composition can include at least one tumor antigen derived from inactivated tumor lysate, such as from a melanoma or a synthetic antigen, such as a neoantigen, and the photo-sensitive biological pigment can include melanin. In some embodiments, the immunogenic composition can further include an immunostimulant that is capable of stimulating an immune cell.

Embodiments of the present disclosure include methods of treating a subject with a tumor, and/or preventing tumor formation in a subject. In accordance with these embodiments, the methods include contacting an area of the subject's skin with a photo-responsive dermal applicator described above, and delivering light energy to the dermal applicator, wherein the delivery of light energy transforms into local heat stimulating an immune response in the subject against the tumor. In some embodiments, the delivery of light energy to the dermal applicator comprises delivering near infrared (NIR) light, UV light, or light with wavelengths from about 10 nm to about 1000 nm. Delivering light to the dermal applicator can stimulate the photo-sensitive biological pigment, such as melanin, to create a hyperthermic microenvironment to stimulate an immune response to treat the tumor and/or prevent tumor formation.

BRIEF DESCRIPTION OF THE DRAWINGS

FIGS. 5A-5G demonstrate immunologic responses after the MN-mediated cancer immunotherapy. (A) Representative quantitative analysis of T cells (gated on CD3+ T cells) in treated tumors analyzed by flow cytometry. (B) Representative quantitative analysis of activated DCs (CD86+, CD80+) in the draining lymph nodes analyzed by flow cytometry. Data points represent mean±SD (n=8) (C) Immunofluorescent staining of the tumors showing CD4+ T cell and CD8+ T cell infiltration (scale bar: 100 μm). (D) Quantification of IgG1 subtypes in serum collected at day 10. Data points represent mean±SD (n=8). (E) Cytotoxic responses of splenocytes against B16F10 cells in vitro. Data points represent mean±SD (n=6). (F) Immunofluorescent staining of HSP70 (green) in the regional skin with actin filaments visualized by Alexa Fluor 660-phalloidin (red) and cell nuclei stained with Hoechst (blue) (scale bar: 100 μm). (G) In vivo local detection of cytokines from extracted applicators at day 3. Statistical significance was calculated by the Student t-test (* P<0.05; ** P<0.01). Data points represent mean±SD (n=8). Error bars indicate SD.

FIGS. 6A-6K demonstrate antitumor effects of local cancer immunotherapy treatment toward distant B16F10 tumors. (A) Schematic representation of the B16F10 tumor model. (B) Photograph of a mouse before and after MN administration. Red arrows indicate established tumors on both sides. The red line indicates the MN injection site. (C) Tumor weights in different experimental groups (n=3). (D) Tumor-infiltrating CD8+ T cells after treatments in different experimental groups (n=6). Asterisks in C, D indicate statistically significant differences between blank MN and other groups. (E) Images of tumors extracted from treated mice indicated by the labels in (D). (F) In vivo bioluminescence imaging of treated B16F10 melanoma at different time points after treatment. Shown were one representative mouse per treatment group. (G) Average tumor volumes in treated mice. (H) Body weights of treated mice (n=6). (I) Average B16F10 tumor volumes in mice treated with MNs loaded with BP lysate with melanin and blank MN (n=8). (J) Average tumor volumes in vaccinated mice rechallenged with either B16F10 cells or BP cells on day 80. (K) Kaplan-Meier survival curves for rechallenged mice. Data points represent mean±SD (n=8). Error bars indicate SD. Statistical significance was calculated by the Student t-test and Log-rank test (NS. P>0.05; * P<0.05;  P<0.01; * P<0.001).

FIGS. 17A-17C demonstrate that Melanin-loaded MNs confer protective immunity in vivo. (A) Surface temperature changes of individual animal in real time after MN insertion into the skin and NIR (1.0 W/cm$^2$) irradiation measured by an infrared thermal camera. (B) Average tumor volumes for treated and control mice. (C) Kaplan-Meier survival curves for treated and control mice. Data points represent mean±SD (n=6). Error bars indicate SD. Statistical significance was calculated by the Student t-test and Log-rank test (* P<0.05; ** P<0.01).

FIGS. 18A-18B demonstrate tumor growth in control and treated mice. (A) Average and (B) individual B16F10 tumor growth curves for mice after tumor inoculation and the indicated treatments. The tumor growth curve was plotted 10 days after tumor cell inoculation. Data points represent mean±SD (n=8). Error bars indicate SD. Statistical significance was calculated by the Student t-test (* P<0.05;  P<0.01; * P<0.001).

FIG. 19 includes data quantifying B16F10 bioluminescent tumor signals in control and treated mice. Error bars indicate SD (n=3). Statistical significance was calculated by the Student t-test (NS. P>0.05; * P<0.05; ** P<0.01).

FIG. 20 includes data of tumor weights in control and treated mice. Data points represent mean±SD (n=8). Error bars indicate SD. Statistical significance was calculated by the Student t-test (** P<0.01).

FIGS. 21A-21B include histology and apoptosis analysis of tumor sections. (A) H&E staining and quantitative analysis of melanin content in tumor sections. (B) Fluorescence images and quantitative analysis of in situ TUNEL-positive nuclei of tumors collected from mice after each indicated treatments. The tumor sections were stained with the fluorescein-dUTP (green) for apoptosis and DAPI for nuclei (blue) (scale bar: 100 μm). Data points represent mean±SD (n=3). Error bars indicate SD. Statistical significance was calculated by the Student t-test (* P<0.05;  P<0.01; * P<0.001).

FIG. 22 includes data of tumor growth of mice receiving the transdermal cancer immunotherapy. Average tumor volumes in mice after tumor inoculation and treatments of vaccine MNs and NIR irradiation under conditions of CD8 T cell depletion (CD8), CD4 T cell depletion (CD4), natural killer (NK) cell depletion (NK) and B cell depletion (B). Controls are naive mice treated with blank MN (blank) and vaccine MN with NIR irradiation (MN+NIR). Data points represent mean±SD (n=8). Error bars indicate SD. Statistical significance was calculated by the Student t-test (NS. P>0.05; * P<0.05;  P<0.01; * P<0.001).

FIGS. 23A-23C include measurements of local microcirculatory blood perfusion of mice. Data were collected right after treatment of different conditions using the Laser Doppler flowmetry. Mice were treated with: (A) blank MN, (B) vaccine MN and (C) vaccine MN and NIR irradiation. The experiments were repeated three times and quantitative analysis is summarized in Table 2.

FIGS. 24A-24B demonstrate immunologic responses after the transdermal cancer immunotherapy. (A) Representative plots and (B) quantitative analysis of tetramer GP100 staining in CD8+ T cells from tumors in treated mice analyzed by flow cytometry. Data points represent mean±SD (n=3). Error bars indicate SD. Statistical significance was calculated by the Student t-test (* P<0.05).

FIG. 25 includes quantification of IgG1 subtypes in serum. Serum was collected at day 15 post treatment with blank, MN or MN+NIR. Data points represent mean±SD (n=8). Error bars indicate SD. Statistical significance was calculated by the Student t-test (* P<0.05; ** P<0.01).

FIGS. 26A-26B demonstrate reactive oxygen species (ROS) detection by flow cytometry in tumor sections. (A) Normalized mean ROS signal intensity in tumors collected from different experimental groups. (B) Quantitative mean ROS signal intensity (n=6). Error bars indicate SD. Statistical significance was calculated by the Student t-test (* P<0.05).

FIGS. 27A-27B demonstrate HSP90 expression after the transdermal cancer immunotherapy. (A) Immunofluorescent staining of HSP90 (green) in the skin collected after the indicated treatments. Actin filaments were visualized by phalloidin (red) and cell nuclei stained with Hoechst (blue) (scale bar: 100 μm). (B) Quantitative analysis of HSP 90 signal intensity in the immunofluorescent staining images. Data points represent mean±SD (n=3). Error bars indicate SD. Statistical significance was calculated by the Student t-test (* P<0.05).

FIG. 28 includes cytokine kinetics after the transdermal cancer immunotherapy. Cytokine concentration was measured in extracted applicator and surrounding tissue in B16F10 tumor model at the indicated time points. Data points represent mean±SD (n=3). Error bars indicate SD. Statistical significance was calculated by the Student t-test (* P<0.05; ** P<0.01).

FIGS. 29A-29B include histology analysis after the transdermal cancer immunotherapy. (A) H&E staining of organs collected from mice after combinational treatments and control mice with lung metastasis as well as healthy mice. The dark blue arrows indicate the metastatic tumors in the lung. (B) Pictures of lungs collected (scale bar: 100 μm) and quantification of the lung nodules from mice receiving different treatments. Data points represent mean±SD (n=3). Error bars indicate SD. Statistical significance was calculated by the Student t-test (*** P<0.001).

FIGS. 30A-30B demonstrate antitumor effects of the transdermal cancer immunotherapy toward different tumor models. (A) Average and (B) individual B16F10 and BP tumor growth curves for mice receiving the indicated treatments. Data points represent mean±SD (n=8). Error bars indicate SD. Statistical significance was calculated by the Student t-test (*** P<0.001).

FIG. 31 demonstrates surface temperature changes of the melanin-loaded MNs. Images were measured by an infrared thermal camera in real time after insertion into mouse skin and 1.0 W/cm$^2$ NIR irradiation. MNs were loaded with melanoma BP lysate or breast cancer 4T1 lysate with melanin.

FIGS. 32A-32D demonstrate antitumor effects of the transdermal cancer immunotherapy. (A) Tumor growth of vaccinated C57BL/6J mice after BP tumor cell challenge. Mice were pretreated with blank MN (blank), MN loaded with BP tumor lysate and melanin (MN) or loaded MN combined with NIR irradiation (MN+NIR). (B) Tumor growth of C57BL/6J mice bearing established BP tumors before therapeutic treatment with blank MN (blank), MN loaded with BP tumor lysate and melanin (MN) or loaded MN combined with NIR irradiation (MN+NIR) (C) Tumor growth of vaccinated BALB/cJ mice after 4T1 tumor cell challenge. Mice were pretreated with blank MN (blank), MN loaded with 4T1 tumor lysate and melanin (MN) or loaded MN combined with NIR irradiation (MN+NIR). (D) Tumor growth of BALB/cJ mice bearing established 4T1 tumors before therapeutic treatment with blank MN (blank), MN loaded with 4T1 tumor lysate and melanin (MN) or loaded MN combined with NIR irradiation (MN+NIR). Data points represent mean±SD (n=8). Statistical significance was calculated by the Student t-test (* P<0.05;  P<0.01; * P<0.001). Asterisks indicate statistically significant differences between MN+NIR group and all other treatment groups.

FIGS. 33A-33B demonstrate HSP70 expression after the transdermal cancer immunotherapy. (A) Immunofluorescent staining of HSP70 (green) in the regional skin with actin filaments visualized by phalloidin (red) and cell nuclei stained with Hoechst (blue) in BP and 4T1 tumor models respectively (scale bar: 100 μm). (B) Quantitative intensity of HSP70 in the in the regional skin samples. Data points represent mean±SD (n=3). Error bars indicate SD. Statistical significance was calculated by the Student t-test (* P<0.05; ** P<0.01).

FIGS. 34A-34B include representative quantitative analysis of DC activation. Activated DCs (CD86+, CD80+) were collected in the draining lymph nodes in (A) BP and (B) 4T1 tumor models. Data points represent mean±SD (n=3). Error bars indicate SD. Statistical significance was calculated by the Student t-test (* P<0.05).

FIGS. 35A-35B include cytokine kinetics after the transdermal cancer immunotherapy in different tumor models. Cytokine concentrations were measured in the extracted applicator and surrounding tissue in (A) BP and (B) 4T1 tumor models. Data points represent mean±SD (n=3). Error bars indicate SD. Statistical significance was calculated by the Student t-test (* P<0.05).

FIGS. 36A-36D include average weights of mice after the transdermal cancer immunotherapy in control and treated mice. (A) Average weight of vaccinated C57BL/6J mice after BP tumor cell challenge. (B) Average weight of C57BL/6J mice bearing established BP tumors before therapeutic treatment. (C) Average weight of vaccinated BALB/cJ mice after 4T1 tumor cell challenge. (D) Average weight of BALB/cJ mice bearing established 4T1 tumors before therapeutic treatment. Data points represent mean±SD (n=8).

FIG. 37 includes representative H&E staining of organs collected after the transdermal cancer immunotherapy in (A) C57BL/6J mice bearing BP tumors and (B) BALB/cJ mice bearing 4T1 tumors post vaccinations (scale bar: 100 μm).

DETAILED DESCRIPTION

Figure 1A:
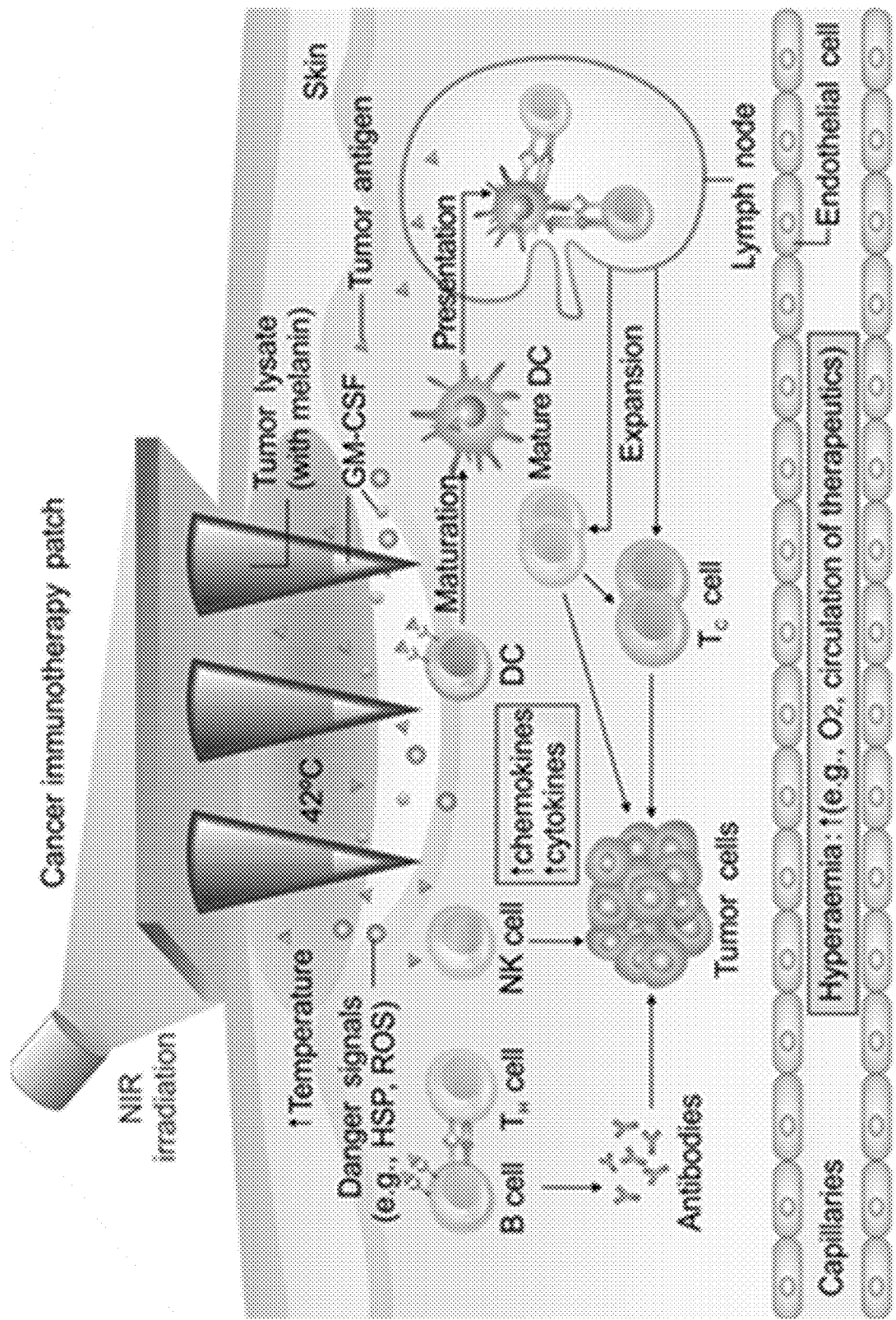
FIGS. 1A-1B include representative schematics and images of a transdermal MN-based applicator for melanin-mediated cancer immunotherapy. (A) Schematic illustration of MN-based transdermal vaccination. Tx cell: T helper cell, Tc cell: cytotoxic T cell. (B) Photograph of representative MN applicators without (w/o) melanin and with (w/) melanin (scale bar: 4 mm). (C) Scanning electron microscopy image of the MN applicator (scale bar: 400 µm). (D) Fluorescent cross-sectional images of a representative MN. Actin filaments in cells were visualized by Alexa Fluor 488-phalloidin (green), cell DNA fragments were stained with Hoechst (blue), and hyaluronic acid polymer matrix was stained with rhodamine (red) (scale bar: 200 µm). (E) Fluorescence imaging of a representative MN-array applicator that contained the Alexa Fluor 488-phalloidin-labeled tumor lysate and rhodamine labeled-hyaluronic acid (scale bar: 400 µm).

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The term "administering" refers to an administration that is oral, topical, intravenous, subcutaneous, transcutaneous, transdermal, intramuscular, intra joint, parenteral, intra-arteriole, intradermal, intraventricular, intracranial, intraperitoneal, intralesional, intranasal, rectal, vaginal, by inhalation or via an implanted reservoir. Administering can be performed using transdermal microneedle-array patches. The term "parenteral" includes subcutaneous, intravenous, intramuscular, intra-articular, intra-synovial, intrasternal, intrathecal, intrahepatic, intralesional, and intracranial injections or infusion techniques. "Biocompatible" generally refers to a material and any metabolites or degradation products thereof that are generally non-toxic to the recipient and do not cause any significant adverse effects to the subject.

The term "carrier" or "pharmaceutically acceptable carrier" means a carrier or excipient that is useful in preparing a pharmaceutical or therapeutic composition that is generally safe and non-toxic, and includes a carrier that is acceptable for veterinary and/or human pharmaceutical or therapeutic use. As used herein, the terms "carrier" or "pharmaceutically acceptable carrier" encompasses can include phosphate buffered saline solution, water, emulsions (such as an oil/water or water/oil emulsion) and/or various types of wetting agents. As used herein, the term "carrier" encompasses any excipient, diluent, filler, salt, buffer, stabilizer, solubilizer, lipid, stabilizer, or other material well known in the art for use in pharmaceutical formulations and as described further below.

As used herein, the term "pharmaceutically acceptable" can refer to a component that is not biologically or otherwise undesirable. For example, the component may be incorporated into a pharmaceutical formulation of the invention and administered to a subject as described herein without causing any significant undesirable biological effects or interacting in a deleterious manner with any of the other components of the formulation in which it is contained. When the term "pharmaceutically acceptable" is used to refer to an excipient, it is generally implied that the component has met the required standards of toxicological and manufacturing testing or that it is included on the Inactive Ingredient Guide prepared by the U.S. Food and Drug Administration.

The term "immune checkpoint inhibitor" or "immunotherapeutic" refers to molecules that totally or partially reduce, inhibit, interfere with or modulate one or more checkpoint proteins. Checkpoint proteins regulate immune cell activation or function. Numerous checkpoint proteins are known, such as CTLA-4 and its ligands CD 80 and CD86; and PD1 with its ligands PDL1 and PDL2 (see, e.g., Pardoli, Nature Reviews Cancer 12: 252-264, 2012). These proteins are responsible for co-stimulatory or inhibitory interactions of immune cell responses. Immune checkpoint proteins regulate and maintain self-tolerance and the duration and amplitude of physiological immune responses. Immune checkpoint inhibitors include antibodies or are derived from antibodies.

As used herein, the term "polymer" refers to a relatively high molecular weight organic compound, natural or synthetic, whose structure can be represented by a repeated small unit, the monomer (e.g., polyethylene, rubber, cellulose), which can be joined to form a larger polymeric matrix. Synthetic polymers are typically formed by addition or condensation polymerization of monomers. As used herein, the term "copolymer refers to a polymer formed from two or more different repeating units (monomer residues). By way of example and without limitation, a copolymer can be an alternating copolymer, a random copolymer, a block copolymer, or a graft copolymer. It is also contemplated that, in certain aspects, various block segments of a block copolymer can themselves comprise copolymers.

"Prevention," "prevent," and/or "preventing" (and any derivatives thereof) as used herein refers to arresting, halting, and/or inhibiting the growth or advancement of a tumor, including arresting, halting, and/or inhibiting the metastatic process or progression and subsequent metastasis.

"Subject" and "patient" as used herein interchangeably refers to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgous or rhesus monkey, chimpanzee, etc.) and a human). In some embodiments, the subject may be a human or a non-human. The subject or patient may be undergoing other forms of treatment.

As used herein, a "therapeutically effective amount" of a therapeutic agent refers to an amount that is effective to achieve a desired therapeutic result, and a "prophylactically effective amount" of a therapeutic agent refers to an amount that is effective to prevent an unwanted physiological condition. Therapeutically effective and prophylactically effective amounts of a given therapeutic agent will typically vary with respect to factors such as the type and severity of the disorder or disease being treated and the age, gender, and weight of the subject. The term "therapeutically effective amount" can also refer to an amount of a therapeutic agent, or a rate of delivery of a therapeutic agent (e.g., amount over time), effective to facilitate a desired therapeutic effect. The precise desired therapeutic effect will vary according to the condition to be treated, the tolerance of the subject, the drug and/or drug formulation to be administered (e.g., the potency of the therapeutic agent (drug), the concentration of drug in the formulation, and the like), and a variety of other factors that are appreciated by those of ordinary skill in the art.

"Treat," "treated," or "treating," as used herein, refer to a therapeutic method wherein the object is to slow down (lessen) an undesired physiological condition, disorder or disease, or to obtain beneficial or desired clinical results. In some aspects of the present disclosure, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment also includes prolonging survival as compared to expected survival if not receiving treatment.

"Variant" with respect to a peptide or polypeptide that differs in amino acid sequence by the insertion, deletion, or conservative substitution of amino acids, but retain at least one biological activity. Variant may also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes may be identified, in part, by considering the hydropathic index of amino acids, as understood in the art. The hydropathic index of an amino acid is based on a consideration of its hydrophobicity and charge. It is known in the art that amino acids of similar hydropathic indexes may be substituted and still retain protein function. In one aspect, amino acids having hydropathic indexes of ±2 are substituted. The hydrophilicity of amino acids may also be used to reveal substitutions that would result in proteins retaining biological function. A consideration of the hydrophilicity of amino acids in the context of a peptide permits calculation of the greatest local average hydrophilicity of that peptide. Substitutions may be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

"Vector" is used herein to describe a nucleic acid molecule that can transport another nucleic acid to which it has been linked. One type of vector is a "plasmid", which refers to a circular double-stranded DNA loop into which additional DNA segments may be ligated. Another type of vector is a viral vector, wherein additional DNA segments may be ligated into the viral genome. Certain vectors can replicate autonomously in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. "Plasmid" and "vector" may be used interchangeably as the plasmid is the most commonly used form of vector. However, other forms of expression vectors, such as viral vectors (e.g., replication defective retroviruses, adenoviruses and adeno-associated viruses), which serve equivalent functions, can be used. In this regard, RNA versions of vectors (including RNA viral vectors) may also find use in the context of the present disclosure.

Before any embodiments of the present disclosure are explained in detail, it is to be understood that the present disclosure is not limited in its application to the details of construction and the arrangement of components set forth in the following description or illustrated in the accompanying drawings. The present disclosure is capable of other embodiments and of being practiced or of being carried out in various ways.

Other aspects of the invention will become apparent by consideration of the detailed description and accompanying drawings.

Embodiments of the present disclosure relate generally to photoimmunotherapy for treating cancer. More particularly, the present disclosure provides a photo-responsive dermal applicator that uses a transdermal microneedle array to administer an immunogenic composition and a photo-sensitive biological pigment to a subject to treat and/or prevent cancer.

Melanin is capable of transforming 99.9% of the absorbed sunlight energy into heat, reducing the risk of skin cancer. Embodiments of the present disclosure include a melanin-mediated cancer immunotherapy strategy through a transdermal microneedle-array applicator (also referred to as an "applicator patch" or "patch"). In accordance with these embodiments, For example, B16F10 whole tumor lysate containing melanin can be loaded into polymeric microneedles that allow sustained release of the lysate upon insertion into the skin. In combination with light energy, such as near-infrared light irradiation, melanin in the applicator mediates the generation of heat which further promotes tumor-antigen uptake by dendritic cells, and leads to enhanced antitumor treatment and vaccination. Without being bound to any particular theory, the spatiotemporal photo-responsive immunotherapy increases infiltration of polarized T cells and local cytokines release. For example, these immunologic effects increase the survival of mice after tumor challenge and elicited antitumor effects towards established primary tumor and distant tumor. Collectively, melanin generates local heat, boosts T cell activities by transdermal vaccines and promotes antitumor immune responses.

As would be recognized by one of skill in the art based on the present disclosure, the immunogenic compositions used in the photo-responsive MN applicators of the present disclosure can be used to both treat and prevent/inhibit cancerous tumor formation. Generally, cancer vaccines belong to a class of substances known as biological response modifiers. Biological response modifiers work by stimulating or restoring the immune system's ability to fight infections and disease. There are two broad types of cancer vaccines: preventive (or prophylactic) vaccines, which are intended to prevent cancer from developing in healthy people; and treatment (or therapeutic) vaccines, which are intended to treat an existing cancer by strengthening the body's natural immune response against the cancer. Treatment vaccines are a form of immunotherapy. Both preventative (e.g., prophylactic treatment) and treatment (e.g., treatment after diagnosis) vaccine functions are described herein.

Photo-responsive dermal applicators of the present disclosure can include immunogenic compositions comprising whole tumor lysate that targets antigen-presenting cells (APCs) directly via transdermal delivery of tumor lysates combined with a photo-responsive biological pigment, such as melanin (FIG. 1A). This immunogenic composition involves the encapsulation of inactive tumor lysate that is gradually released by an intradermal microneedle (MN) array applicator inserted into the skin. Tumor lysate can be whole or partial tumor lysate, and in some cases can be inactivated whole or partial tumor lysate (e.g., heat inactivated). MNs facilitate the uptake and presentation of antigens by DCs and in turn promote immune activation through the extensive network of lymphatic vessels in the dermis. At the same time, the presence of melanin, which may or may not exist as a natural biological pigment in tumor lysate, allows the local release of heat via remotely-controllable near infrared (NIR) light-emission. Local heat can cause the release of inflammatory cytokines that attract immune cells; the generation of immunogenic substrates such as extracellular heat shock proteins (HSPs), reactive oxygen species (ROS), antigen adjuvants and some other danger signals can activate the immune system. The mild increase in the local temperature of the interstitial tissues can also contribute to the increased blood and lymphatic flow that facilitate the migration of APCs and T cells, thus initiating tumor antigen-specific immune responses. The increased blood flow may also allow the recruitment of other cell subsets such as natural killer (NK) cells. In some embodiments, administration of the photo-responsive dermal applicator can generate robust innate and adaptive immune responses and provided tumor regression in a B16F10 melanoma model. Moreover, the NIR-enhanced transdermal vaccination delayed the growth of distant tumor and improved long-term survival, paving a strong rationale for pursuing this strategy in clinical studies.

In accordance with these embodiments, the present disclosure has demonstrated that integrating B16F10 whole tumor lysate and an immunostimulant, (e.g., granulocyte-macrophage colony-stimulating factor (GM-CSF)), into a transdermal MN applicator can sustain the delivery of an immunogenic composition and target immune cell populations in the epidermis. The incorporation of melanin facilitates local immune activation upon near infrared (NIR) irradiation through the recruitment of DCs and other immune cells. Compared to other photosensitizing agents, melanin is a natural pigment with high biocompatibility and broad absorption spectrum. The efficient light-to-heat transduction mediated by melanin contributes to rapid increase of skin temperature up to about 42° C.

Embodiments of the immunogenic compositions described herein can be used as part of treatment regimens to treat and/or prevent tumor formation in a subject. In accordance with these embodiments, treating a subject with a photo-responsive dermal applicator can increase survival and lead to tumor rejection in 87% of C57BL/6J vaccinated mice. Complete tumor protection was further demonstrated in mice re-challenged with B16F10 tumor cells. After NIR treatment, the elevated local microcirculatory blood perfusion correlated with the migration of local DCs and NK cells. Depletion of B cells, NK cells and T cells attenuated the treatment efficacy in vaccinated mice, highlighting the relevance of immune control in tumor development. Additionally, the production of danger signals and pro-inflammatory cytokines trigger immune activation, including elevated HSP70 and HSP90 expression, and increased ROS levels in the surrounding tissues. This effect was also associated with local enrichment of IFN-γ, TNF-α and IL-6.

Embodiments of the present disclosure demonstrate that photo-responsive dermal applicators containing whole tumor lysate and melanin in a light-irradiated MN applicator patch generate a hyperthermic-mimicking microenvironment that effectively recruits and activates immune cells at the vaccination site. As a result, the melanin-mediated applicator prevents tumor engraftment in prophylactic models and causes sustained tumor regression in tumor-bearing mice. In addition, the use of a photo-sensitive biological pigment can be extended to other biological pigments in addition to melanin, such as carotenoids, xanthophylls, bilirubin, and/or combination and derivatives of these biological pigments, both natural as well as synthetic. Additionally, the methods described herein are also adaptable to deep tissue photoacoustic imaging, biological labeling, and can be used to target a variety of diseases in a photo/thermo-responsive manner.

Embodiments of the present disclosure include photo-responsive dermal applicators for use in photoimmunotherapy. The dermal applicator includes a transdermal microneedle array comprising a plurality of microneedles (or MNs), each microneedle comprising a base portion and a tip portion. The microneedles should have the mechanical strength to remain intact while being inserted into the biological barrier, while remaining in place for up to a number of days, and while being removed. In some embodiments, the microneedle must remain intact at least long enough for the microneedle to serve its intended purpose (e.g., delivery of immunogenic composition). The microneedles can have straight or tapered shafts. In one embodiment, the diameter of the microneedle is greatest at the base end of the microneedle and tapers to a point at the end distal the base. The microneedle can also be fabricated to have a shaft that includes both a straight (untapered) portion and a tapered portion. The needles may also not have a tapered end at all, i.e. they may simply be cylinders with blunt or flat tips. The microneedles can be oriented perpendicular or at an angle to the substrate. In one embodiment, the microneedles are oriented perpendicular to the substrate so that a larger density of microneedles per unit area of substrate can be provided. An array of microneedles can include a mixture of microneedle orientations, heights, or other parameters. The microneedles can be formed with shafts that have a circular cross-section in the perpendicular, or the cross-section can be non-circular. For example, the cross-section of the microneedle can be polygonal (e.g. star-shaped, square, triangular), oblong, or another shape. The cross-sectional dimensions can be from about 1 μm to about 1000 μm, such that the base can be from about 100 to about 500 μm, and the tip can be from about 1 μm to about 20 μm. In one embodiment, the microneedle can be approximately 300 μm at the base, and approximately 5μ, μm at the tip. The length of the microneedles typically is from about 10 μm to about 1 mm, including from about 400 μm and 1 mm. In one embodiment, the length (or height) of the microneedle is about 800 μm. The length is selected for the particular application, accounting for both an inserted and uninserted portion. An array of microneedles can include a mixture of microneedles having, for example, various lengths, outer diameters, inner diameters, cross-sectional shapes, and spacings between the microneedles. In one embodiment, the microneedles are arranged in a 15 by 15 array with 600 μm tip-to-tip spacing.

Embodiments of the present disclosure also include an immunogenic composition comprising at least one tumor antigen. The tumor antigen can include any antigen or neoantigen, either synthetic or naturally-occurring, associated with the onset or development of a cancerous tumor in a subject. The antigenic epitopes on the tumor antigen can be known or not yet identified. Tumor antigens in the immunogenic compositions of the present disclosure can be synthetic tumor antigens, such as neoantigens, or derived from tumor lysate (or any antigenic components thereof) of any cancer, such as, but not limited to, a solid tumor, for example, melanoma, lung cancer (including lung adenocarcinoma, basal cell carcinoma, squamous cell carcinoma, large cell carcinoma, bronchioloalveolar carcinoma, bronchogenic carcinoma, non-small-cell carcinoma, small cell carcinoma, mesothelioma); breast cancer (including ductal carcinoma, lobular carcinoma, inflammatory breast cancer, clear cell carcinoma, mucinous carcinoma, serosal cavities breast carcinoma); colorectal cancer (colon cancer, rectal cancer, colorectal adenocarcinoma); anal cancer; pancreatic cancer (including pancreatic adenocarcinoma, islet cell carcinoma, neuroendocrine tumors); prostate cancer; prostate adenocarcinoma; ovarian carcinoma (ovarian epithelial carcinoma or surface epithelial-stromal tumor including serous tumor, endometrioid tumor and mucinous cystadenocarcinoma, sex-cord-stromal tumor); liver and bile duct carcinoma (including hepatocellular carcinoma, cholangiocarcinoma, hemangioma); esophageal carcinoma (including esophageal adenocarcinoma and squamous cell carcinoma); oral and oropharyngeal squamous cell carcinoma; salivary gland adenoid cystic carcinoma; bladder cancer; bladder carcinoma; carcinoma of the uterus (including endometrial adenocarcinoma, ocular, uterine papillary serous carcinoma, uterine clear-cell carcinoma, uterine sarcomas, leiomyosarcomas, mixed mullerian tumors); glioma, glioblastoma, medulloblastoma, and other tumors of the brain; kidney cancers (including renal cell carcinoma, clear cell carcinoma, Wilm's tumor); cancer of the head and neck (including squamous cell carcinomas); cancer of the stomach (gastric cancers, stomach adenocarcinoma, gastrointestinal stromal tumor); testicular cancer; germ cell tumor; neuroendocrine tumor; cervical cancer; carcinoids of the gastrointestinal tract, breast, and other organs; signet ring cell carcinoma; mesenchymal tumors including sarcomas, fibrosarcomas, haemangioma, angiomatosis, haemangiopericytoma, pseudoangiomatous stromal hyperplasia, myofibroblastoma, fibromatosis, inflammatory myofibroblastic tumor, lipoma, angiolipoma, granular cell tumor, neurofibroma, schwannoma, angiosarcoma, liposarcoma, rhabdomyosarcoma, osteosarcoma, leiomyoma, leiomysarcoma, skin, including melanoma, cervical, retinoblastoma, head and neck cancer, pancreatic, brain, thyroid, testicular, renal, bladder, soft tissue, adenal gland, urethra, cancers of the penis, myxosarcoma, chondrosarcoma, osteosarcoma, chordoma, malignant fibrous histiocytoma, lymphangiosarcoma, mesothelioma, squamous cell carcinoma; epidermoid carcinoma, malignant skin adnexal tumors, adenocarcinoma, hepatoma, hepatocellular carcinoma, renal cell carcinoma, hypernephroma, cholangiocarcinoma, transitional cell carcinoma, choriocarcinoma, seminoma, embryonal cell carcinoma, glioma anaplastic; glioblastoma multiforme, neuroblastoma, medulloblastoma, malignant meningioma, malignant schwannoma, neurofibrosarcoma, parathyroid carcinoma, medullary carcinoma of thyroid, bronchial carcinoid, pheochromocytoma, Islet cell carcinoma, malignant carcinoid, malignant paraganglioma, melanoma, Merkel cell neoplasm, cystosarcoma phylloide, salivary cancers, thymic carcinomas, and cancers of the vagina among others. In the case of melanoma, the tumor antigen can be derived from a B16F10 melanoma or a BRAFv600E melanoma. In other cases, the tumor antigen can be derived from a 4T1 breast tumor.

Embodiments of the present disclosure can also include an immunogenic composition comprising a photo-sensitive biological pigment. A pigment is a chemical that has a specific color. Biological pigments play vital roles in the daily operation of a subject's body. For example, melanin is a yellow to black pigment in skin that helps to protect it from sun damage by absorbing light energy and dissipating it as heat. Melanin is a broad term for a group of natural pigments found in most organisms. Melanin is produced by the oxidation of the amino acid tyrosine, followed by polymerization. The melanin pigments are produced in a specialized group of cells known as melanocytes. There are three basic types of melanin: eumelanin, pheomelanin, and neuromelanin. The most common type is eumelanin, of which there are two types—brown eumelanin and black eumelanin. Pheomelanin is a cysteine that contains red polymer of benzothiazine units largely responsible for red hair, among other pigmentation. Neuromelanin is found in the brain, though its function remains obscure. In human skin, melanogenesis is initiated by exposure to UV radiation, causing the skin to turn tan. Melanin is an effective absorbent of light; the pigment is able to dissipate over 99.9% of absorbed UV radiation. Because of this property, melanin is thought to protect skin cells from UVB radiation damage, reducing the risk of cancer, and it's considered that exposure to UV radiation is associated with increased risk of malignant melanoma, a cancer of the melanocytes cells.

As one of ordinary skill in the art would recognize based on the present disclosure, other biological pigments can also be used with the immunogenic compositions of the present disclosure, in combination with or as a replacement for melanin. These biological pigments include, but are not limited to, heme/porphyrin-based pigments, such as chlorophyll, bilirubin, hemocyanin, hemoglobin, myoglobin; light-emitting pigments, such as luciferin; carotenoids; hematochromes, such as algal pigments, mixes of carotenoids and their derivates; carotenes, such as alpha and beta carotene, lycopene, rhodopsin; xanthophylls, such as canthaxanthin, zeaxanthin, lutein; proteinaceous pigments, such as phytochrome, phycobiliproteins; polyene enolates; urochrome; and flavonoids. In some embodiments, the photo-sensitive biological pigment is at least one of a melanin, a carotenoid, a xanthophyll, a bilirubin, or a combination thereof. The photo-sensitive biological pigment can also be synthetic, natural, or a combination thereof.

The amount or concentration of the biological pigment(s) that can be included in the immunogenic composition can vary depending on various factors, including but not limited to the nature of the tumor being treated, the characteristics of the subject, etc. In some cases, the amount of biological pigment can be from about 0.01% to about 10% by weight. In some cases, the amount of biological pigment can be from about 0.1% to about 10% by weight. In some cases, the amount of biological pigment can be from about 1% to about 10% by weight. In some cases, the amount of biological pigment can be from about 5.0% to about 10% by weight. In some cases, the amount of biological pigment can be from about 0.1% to about 5% by weight. In some cases, the amount of biological pigment can be from about 0.1% to about 2.5% by weight. Stock solutions of the biological pigment can also be prepared and subsequently diluted before being added to the immunogenic composition. In some cases, the biological pigment stock solution can be about 200 mg/mL, about 150 mg/mL, about 100 mg/mL, about 75 mg/mL, or about 50 mg/mL. These stock solutions can be diluted at ratios ranging from about 1:1000, 1:500 1:250, 1:100, 1:10, and at any other ratio as determined by one of ordinary skill in the art based on the present disclosure.

Embodiments of the present disclosure can also include an immunogenic composition comprising an immunostimulant. Immunostimulants are substances that stimulate the immune system. Specific immunostimulants such as vaccines stimulate an immune response to specific antigenic types. Non-specific immunostimulants do not have antigenic specificity and are widely used in chronic infections, immunodeficiency, autoimmunity and neoplastic diseases. In some immunogenic compositions, adjuvants can be considered immunostimulants that have the important task of presenting antigens to the immune system, eliciting an amplified and antigen-specific immune response. In some embodiments, immunostimulants include granulocyte-macrophage colony-stimulating factor (GM-CSF), a CpG nucleotide, interleukin (IL)-7, IL-15, and combinations thereof. In accordance with these embodiments, immunostimulants can stimulate various immune cells, including NK cells, T cells, B cells, dendritic cells, macrophages, and the like.

In some embodiments, the immunostimulant can include an immune checkpoint inhibitor. There are a number of immunotherapeutic agents that are known to inhibit immune checkpoint proteins (immune checkpoint inhibitors). Known immune checkpoint proteins include CTLA-4, PD1 and its ligands PD-L1 and PD-L2 and in addition LAG-3, BTLA, B7H3, B7H4, TIMS, KIR. The pathways involving LAGS, BTLA, B7H3, B7H4, TFM3, and KIR are recognized in the art to constitute immune checkpoint pathways similar to the CTLA-4 and PD-1 dependent pathways (see, e.g., Pardoll, 2012. Nature Rev Cancer 12:252-264). An immune checkpoint inhibitor is any compound inhibiting the function of an immune checkpoint protein. Inhibition includes reduction of function and/or full blockade. In one embodiment, the immune checkpoint protein is a human immune checkpoint protein. Thus, the immune checkpoint protein inhibitor can be an inhibitor of a human immune checkpoint protein. Immune checkpoint proteins are described in the art (see, e.g., Pardoll, 2012. Nature Rev. Cancer 12: 252-264). Immune checkpoint protein inhibitors can include antibodies that specifically recognize immune checkpoint proteins. A number of PD1, PDL-1, PD-L2, CTLA-4, LAG-3, BTLA, B7H3, B7H4, 4-1BB (CD137), TEVI3 and KIR inhibitors are known and in analogy of these known immune checkpoint protein inhibitors, alternative immune checkpoint inhibitors may be administered using the devices and methods disclosed herein. Examples of PD-1 inhibitors include without limitation humanized antibodies blocking human PD-1 such as pembrolizumab (formerly lambrolizumab), or pidilizumab as well as fully human antibodies such as nivolumab (previously known as MDX-1 106 or BMS-936558). Ipilimumab is a fully human CTLA-4 blocking antibody presently marketed under the name Yervoy (Bristol-Myers Squibb). A second CTLA-4 inhibitor is tremelimumab. In one embodiment, the immunotherapeutic is nivolumab. In addition, immune checkpoint inhibitors may include without limitation humanized or fully human antibodies blocking PD-L1 such as MED 1-4736, MPDL328 OA, and MIH1, as well as other PD-L1 inhibitors. Additional antibodies to PD-LI include atezolizumab and durvalumab.

Embodiments of the present disclosure can also include immunogenic compositions and the biological pigments that are encapsulated within the microneedle array using a polymeric matrix. In some embodiments, the polymeric matrix includes at least one of a glycosaminoglycans, a polysulfated glycosaminoglycans, a glucosoglycans, a polysulfated glucosoglycans, a glucosaminoglycans, a mucopolysaccharides, a carboxymethylcellulose (CMC), a poly(lactide-co-glycolide) (PLGA), a polyvinylpyrrolidone (PVP), a polyvinyl alcohol (PVA), a poly(acrylic acid) (PAA), a poly-L-lactic acid (PLA), maltose, chitosan, alginate, and derivatives and combinations thereof. In some embodiments, the polymeric matrix includes hyaluronic acid. In accordance with these embodiments, the immunogenic composition and the photo-sensitive biological pigment can be encapsulated within the base portion of the plurality of microneedles, while the immunostimulant is encapsulated within the tip portion of the plurality of microneedles, the tip portion distal to the base portion (FIG. 1). In some embodiments, the immunostimulant is encapsulated within the tip portion of the plurality of microneedles by crosslinking methacrylated hyaluronic acid.

As part of the MN dermal applicators disclosed herein, immunogenic compositions can also include a carrier or pharmaceutically acceptable carrier, which can include, but are not limited to, phosphate buffered saline solutions, water, emulsions (such as an oil/water or water/oil emulsion) and/or various types of wetting agents and/or surfactants, any excipient, diluent, filler, salt, buffer, stabilizer, solubilizer, lipid, stabilizer, or other material well known in the art for use in pharmaceutical formulations and as described herein.

Embodiments of the present disclosure also include a means for delivering light energy to the photo-responsive MN dermal applicator in order to stimulate an immune response in a subject. The use of melanin as the biological pigment allows for the use of near infrared (NIR) light energy for various amounts of time and exposure regimens to increase the temperature of the microenvironment around the MN applicator (hyperthermic), as described herein, such as from about 35° C. to about 45° C., or from about 38° C. to about 42° C. This temperature increase can act as an immunostimulant and can recruit various immune cells to the site of the applicator to facilitate the treatment and/or prevention of cancer in a subject.

In some embodiments, methods of treatment and/or prevention of cancer include delivering NIR light, UV light, or light with wavelengths from about 10 nm to about 1000 nm to the dermal applicator. In some cases, light from about 100 nm to about 1000 nm is delivered to the dermal applicator. In some cases, light from about 200 nm to about 1000 nm is delivered to the dermal applicator. In some cases, light from about 300 nm to about 1000 nm is delivered to the dermal applicator. In some cases, light from about 400 nm to about 1000 nm is delivered to the dermal applicator. In some cases, light from about 500 nm to about 1000 nm is delivered to the dermal applicator. In some cases, light from about 800 nm to about 900 nm is delivered to the dermal applicator. In some cases, NIR light is delivered at about 808 nm to the dermal applicator. Although a particular treatment regimen will vary based, for example, on the needs of the subject, the type of tumor, etc., the delivery of light energy to the dermal applicator can include delivering NIR light for about 5 minutes to about 20 minutes. In some embodiments, the delivery of light energy to the dermal applicator includes delivering NIR light at least once per day for about one day to about five consecutive days. In other embodiments, methods of treatment and/or prevention of cancer include delivering light energy multiple times a day for about one day to about five consecutive days.

Examples

The following examples are illustrative of disclosed methods. In light of the present disclosure, those of skill in the art will recognize that variations of these examples and other examples of the disclosed method would be possible without undue experimentation.

Figure 1B:
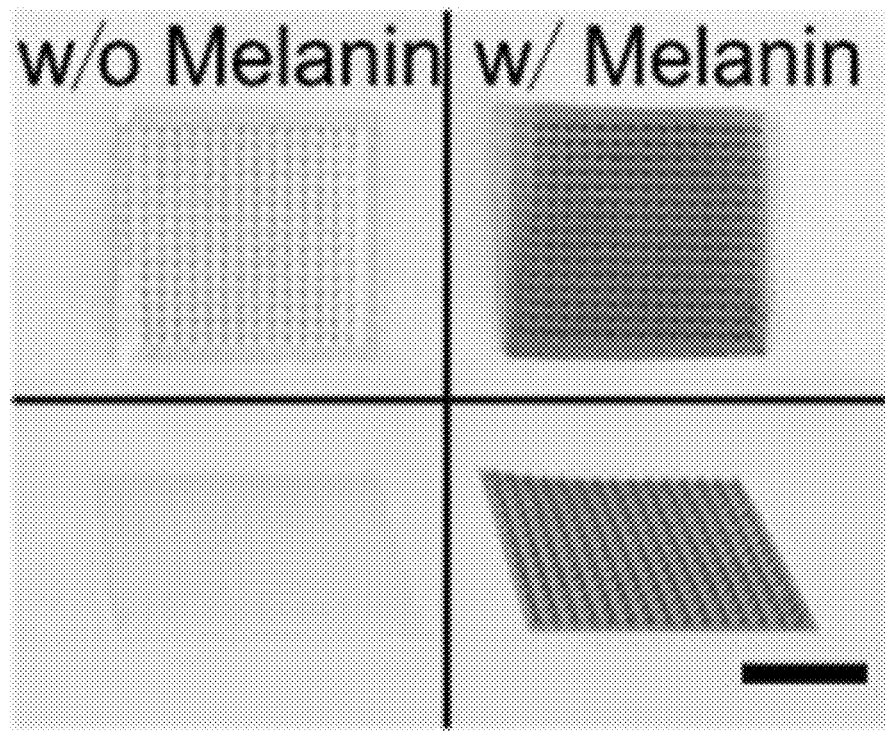
Figure 1C:
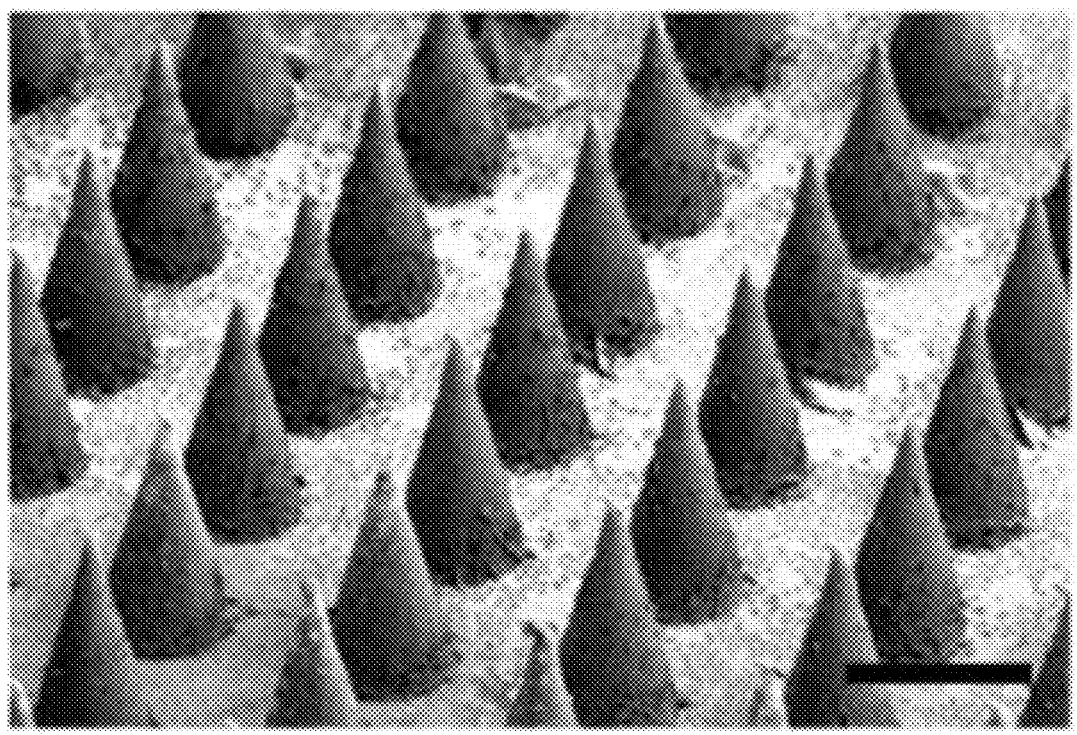
Figure 1D:
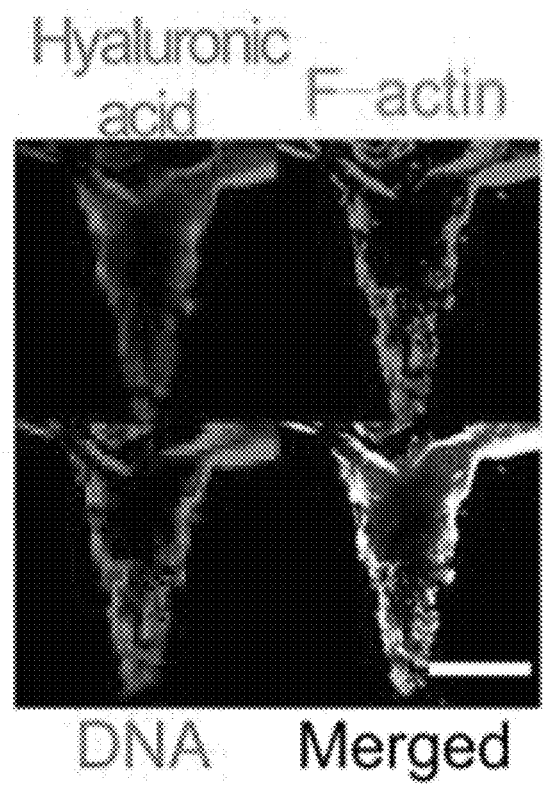
Figure 1E:
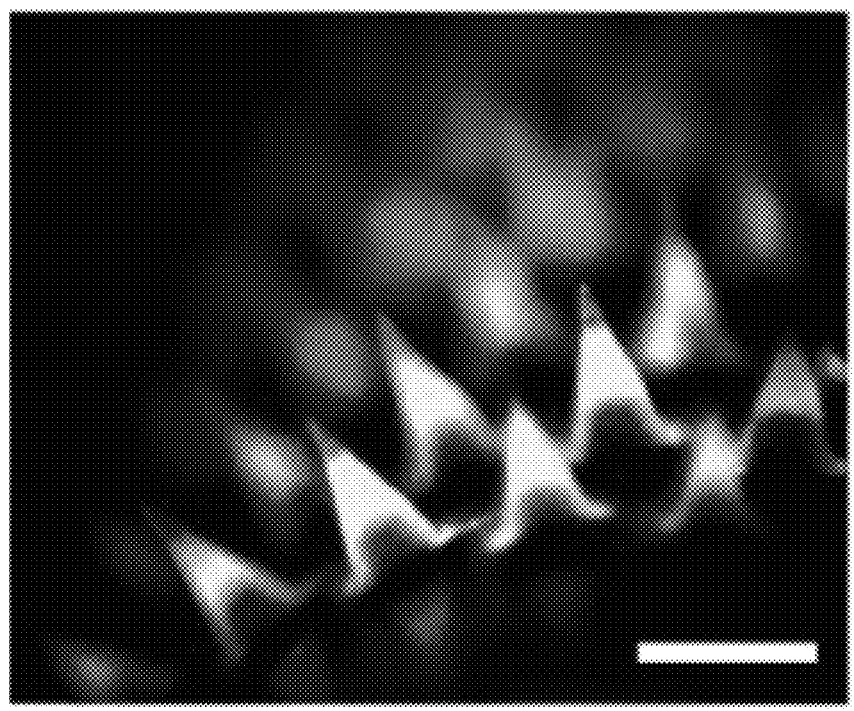
Figure 8:
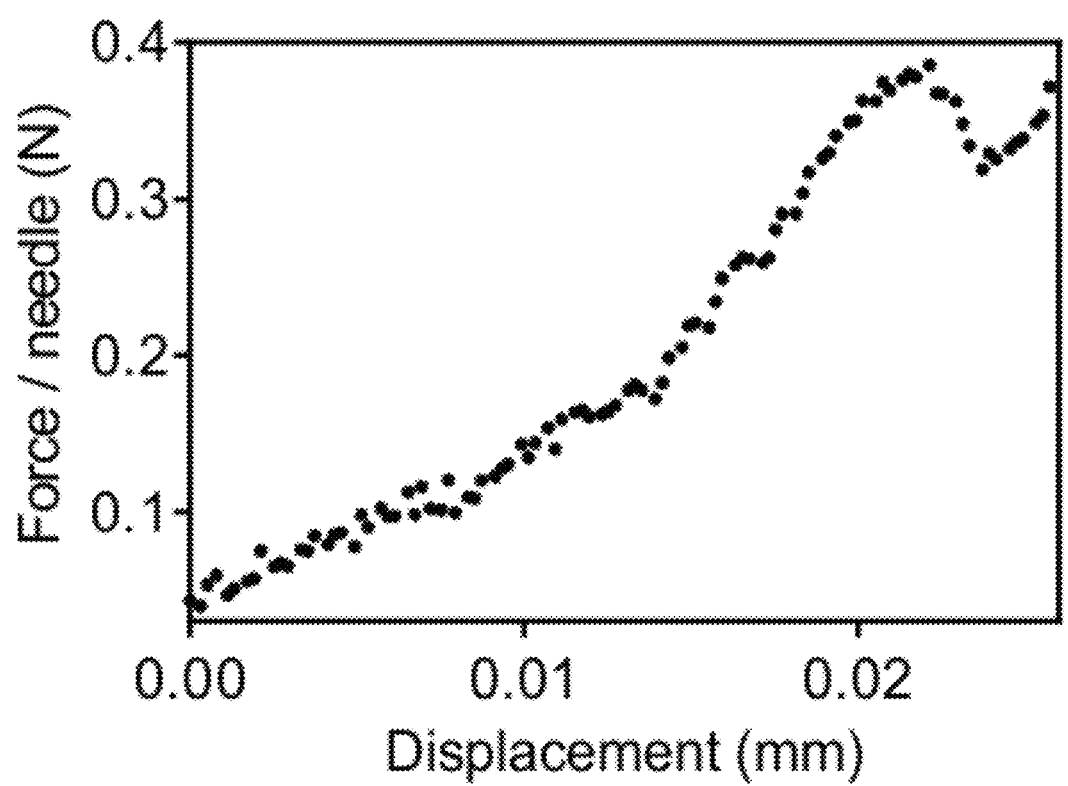
FIG. 8 demonstrates the mechanical properties of transdermal MN-based applicators. Data points show one representative MN. The experiments were repeated three times and similar results were obtained.

Example 1: Preparation and characterization of the photo-responsive dermal applicator for use in photoimmunotherapy. First, it was investigated whether tumor lysate can be loaded and released from transdermal MN applicators in a sustained manner. MN applicators were fabricated within a micromold to form hyaluronic acid-based MNs that encapsulate the whole tumor lysate (with melanin) and the immunostimulants, granulocyte-macrophage colony-stimulating factor (GM-CSF). Applicators with and without tumor lysate are shown from the axial and transverse perspectives, respectively (FIG. 1B). An array of 15×15 MNs was assembled on a 9×9 mm² applicator patch with a center-to-center interval of 600 µm. The detailed dimensions of the MNs were visualized by the scanning electron microscopy (FIG. 1C). Each MN had a conical construction with a diameter of 300 µm at the base, a height of 800 µm and a sharp tip tapering to a 5 µm radius of curvature. Upon loading with the tumor lysate, MNs appeared significantly darker than the blank hyaluronic acid MNs, due to the presence of melanin in the applicator patch. The amount of melanin was around 50 µg per applicator patch which is within the safe dosage range of a single administration. A representative MN was constructed with rhodamine-labelled hyaluronic acid encapsulating tumor lysate with actin filaments and DNA stained with phalloidin and Hoechst, respectively (FIG. 1D). A fluorescent view of the array further showed the uniform loading of tumor lysate and alignment of the MNs (FIG. 1E). The MN underwent failure at 0.39 N in a strain testing, while being compressed to a quarter of its height (FIG. 8), demonstrating sufficient strength for potential skin insertion without buckling.

Figure 2A:
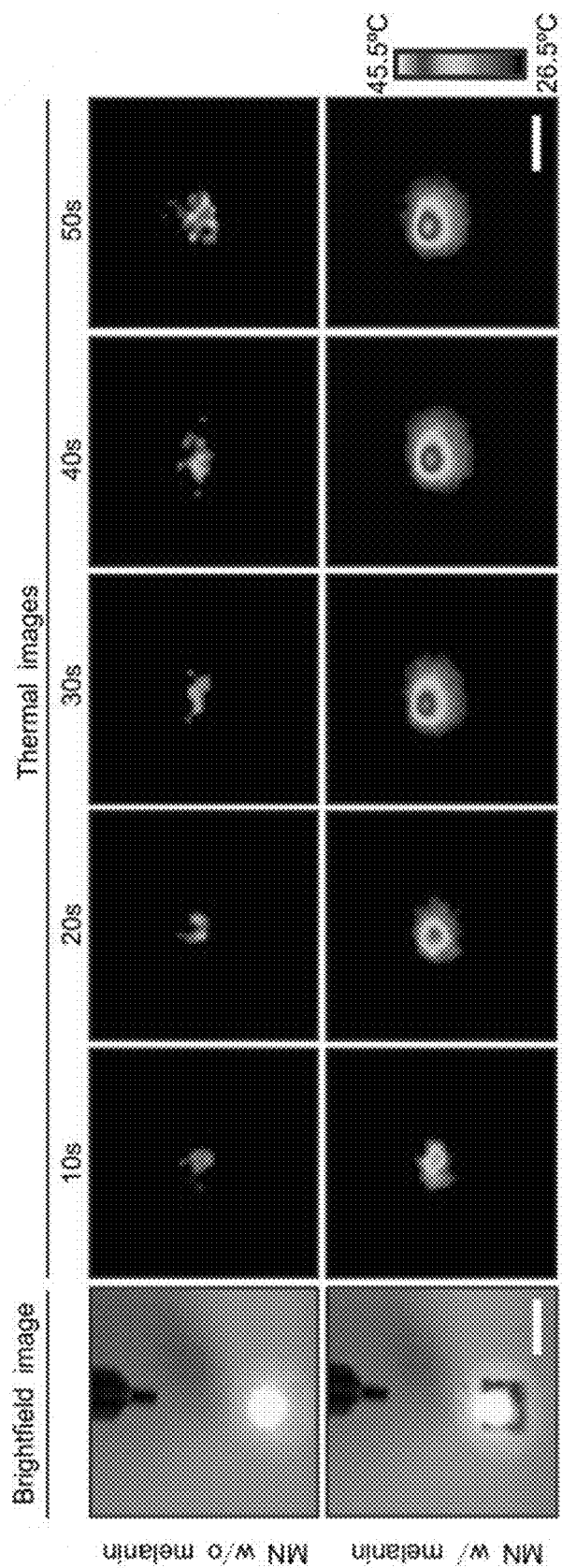
FIGS. 2A-2G characterize light-responsive transdermal MNs. (A) Surface temperature changes of the MNs with or without tumor lysate in real time with continuous 808 nm NIR irradiation at 1.0 W/cm$^2$, characterized by an infrared thermal camera (scale bar: 1 mm). (B) Quantitative surface temperature changes of representative MNs with continuous NIR irradiation at 1.0 W/cm2 (n=3). (C) Quantitative temperature changes of representative MN-array applicator with increasing laser power flux (n=3). (D) In vitro collective release of tumor lysate proteins from the MN-array applicator (n=3). (E) In vitro activation of DCs in response to MNs loaded with tumor lysate and GM-CSF or LPS and exposed to NIR irradiation for different time (n=3). (F) Live/Dead assay of DCs after treatments with (i) blank MN, (ii) 10 minutes of NIR, (iii) MN and (iv) MN and 10 minutes of NIR. (G) Quantification of DC viability after treatments. Data points represent mean±standard deviations (SD) (n=3). Error bars indicate SD. Statistical significance was calculated by the Student t-test (NS. P>0.05; * P<0.05).
Figure 2B:
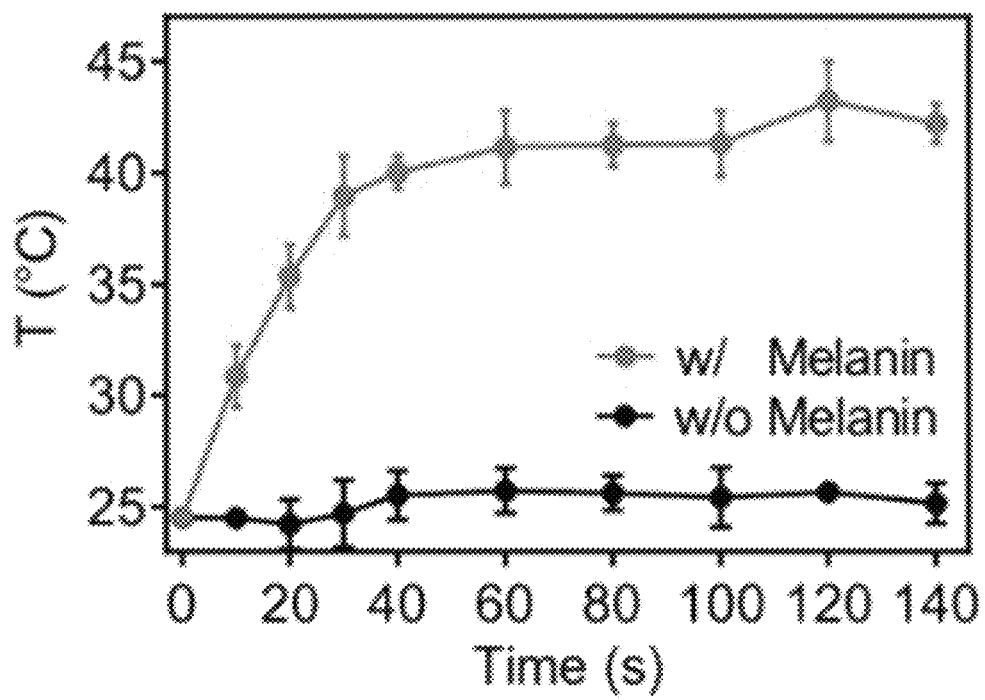
Figure 2C:
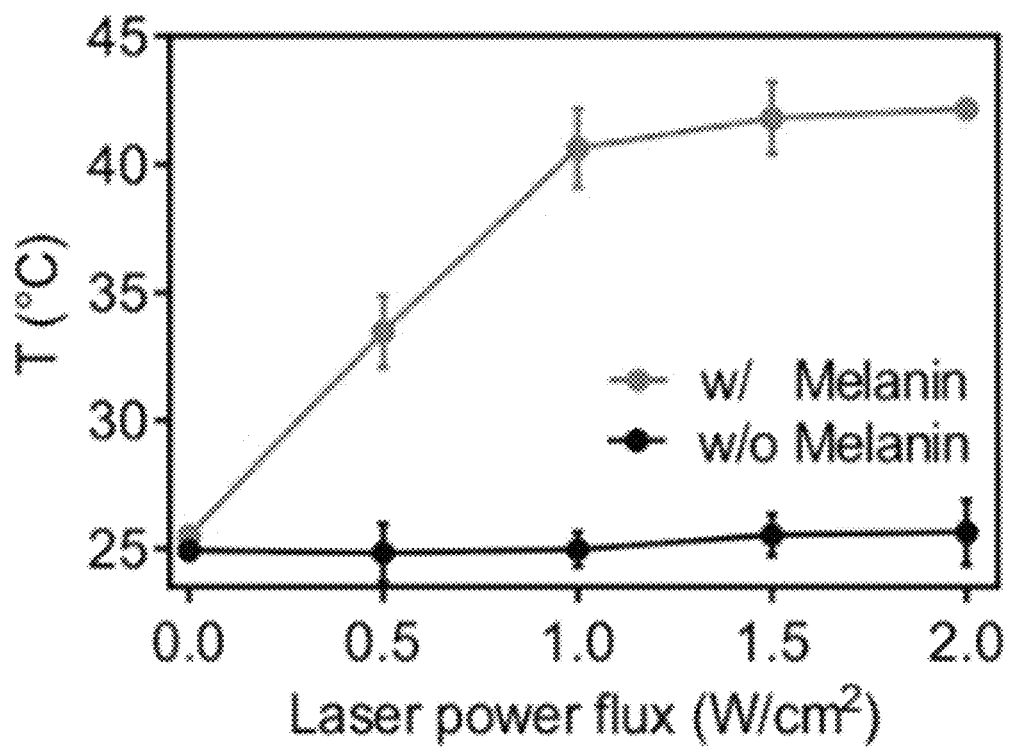
Figure 9A:
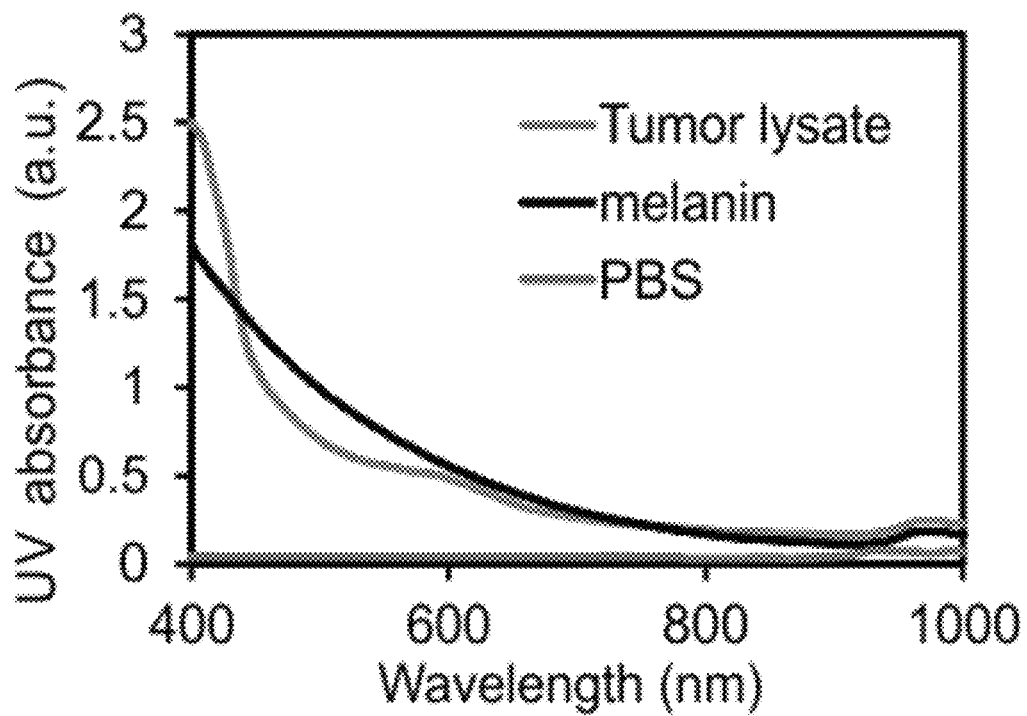
FIGS. 9A-9B include data characterizing tumor lysate solution and synthetic melanin. (A) Absorption spectrum of B16F10 whole tumor lysate solution, synthetic melanin and PBS. (B) Fourier transform infrared spectroscopy of melanin treated with or without 1.0 W/cm$^2$ NIR irradiation for 10 min.
Figure 9B:
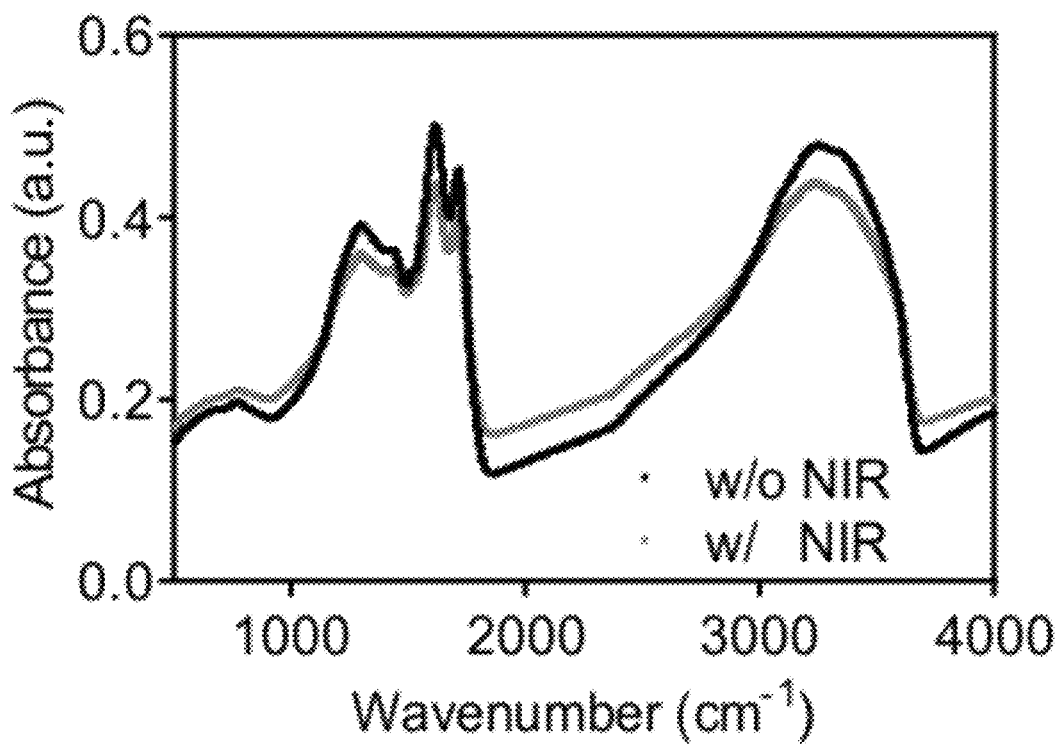
Figure 10A:
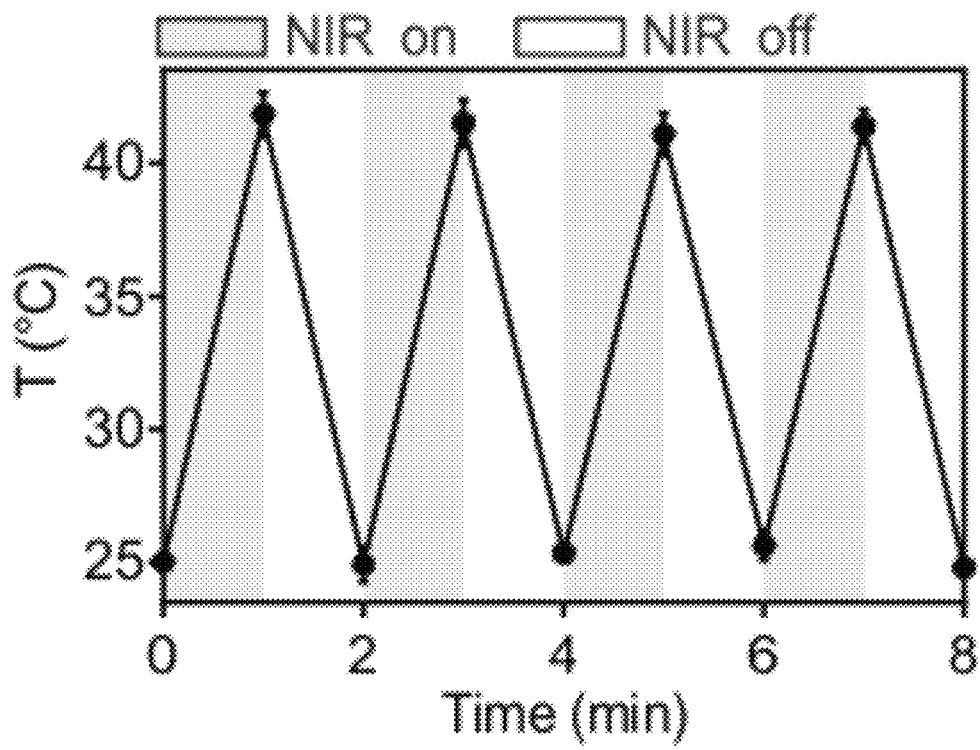
FIGS. 10A-10B demonstrate the heating behavior of MN-array applicators by repetitive NIR irradiation. (A) Pink zone indicates the NIR light on, white zone indicates the NIR light off. (B) Surface temperature changes of the MN applicator when exposed to 1.0 W/cm$^2$ NIR light or no NIR light. Data points represent mean±SD (n=3). Error bars indicate SD.
Figure 10B:
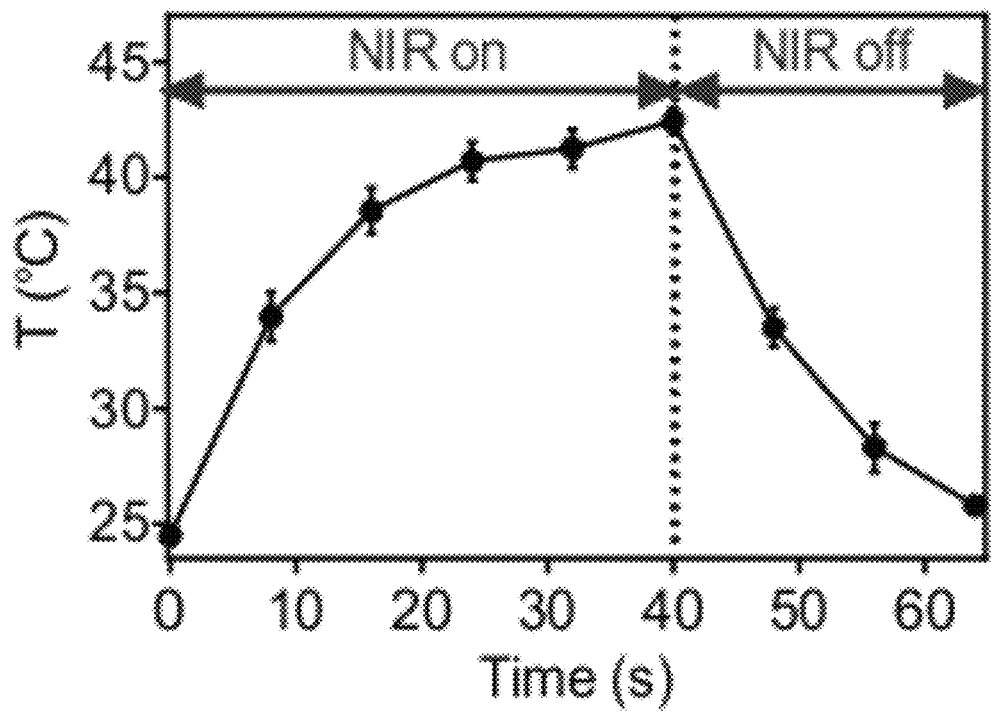
Figure 11A:
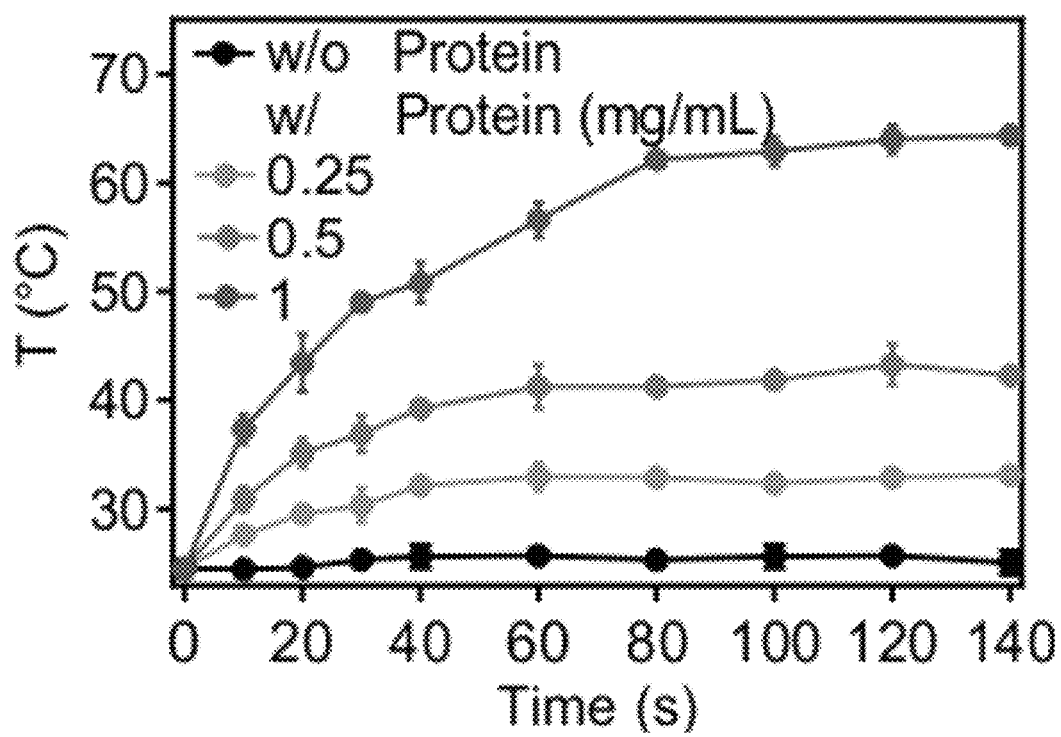
FIGS. 11A-11B demonstrate surface temperature of MN-array applicators with various loadings of tumor lysates upon NIR irradiation. MN-array applicators were exposed to 1.0 W/cm2 NIR light. (A) The surface temperature changes of MN-array applicators with different concentration of extracted tumor lysate proteins. Data points represent mean±SD (n=3). Error bars indicate SD. (B) The surface temperature change of MN-array applicators with different thickness of MN backing. MN-array applicators with different backing thickness were used: (1) 169 μm, (2) 175 μm, (3) 179 μm, (4) 181 μm and (5) 202 μm.
Figure 11B:
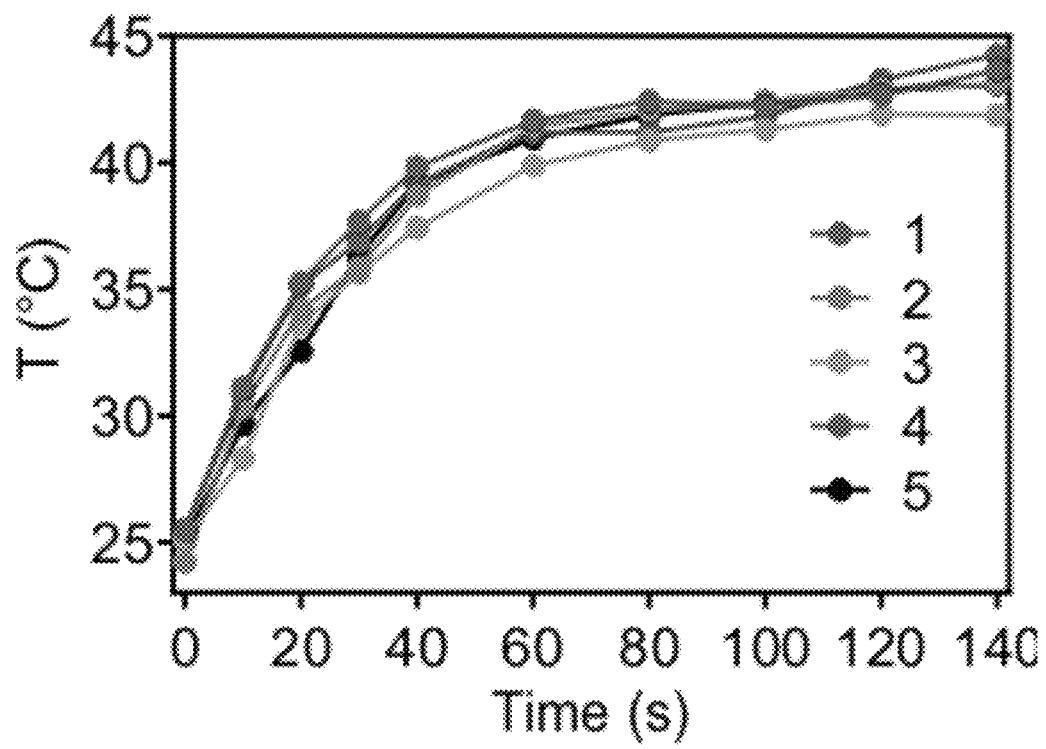

Next, the effects of the NIR laser irradiation on melanin-induced heat generation were evaluated. The temperature variations of the MNs were recorded in real time using an infrared thermal camera (FIG. 2A). Compared to the transparent hyaluronic acid MNs, the surface temperature of the MNs loaded with tumor lysate increased dramatically within one minute due to the melanin-induced light-to-heat transduction (FIG. 2B). NIR irradiation at 808 nm could be absorbed by the melanin contained in the tumor lysate as demonstrated by the melanin's absorption spectrum (FIG. 9A). The absorption coefficient of the melanin content in the tumor lysate was also comparable to that of the synthetic melanin (FIG. 9A and Table 1). Despite the temperature increase, the morphology of the MNs was kept unchanged and the photothermal property of melanin remained stable during the treatment (FIG. 9B). The heating behavior of the MN applicator was also maintained when repeated NIR light exposures were performed (FIG. 10). Furthermore, the steady state of the applicator's surface temperature was lysate concentration- and NIR light intensity-dependent, while the thickness of the MN backing had a minimum effect (FIG. 11 and FIG. 2C). The surface temperature of the applicator could be easily controlled under hyperthermia (42° C.) to minimize the potential thermal-induced denaturation of the tumor antigen and other biomolecules.

TABLE 1

Melanin content of tumors excised from tumor-bearing mice.

| Tumor model | B16F10 | BP | 4T1 |
| --- | --- | --- | --- |
| Melanin content (µg/mg tumor) | 2.10 ± 0.20 | 0.00 ± 0.01 | 0.0 0.01 |

Figure 2D:
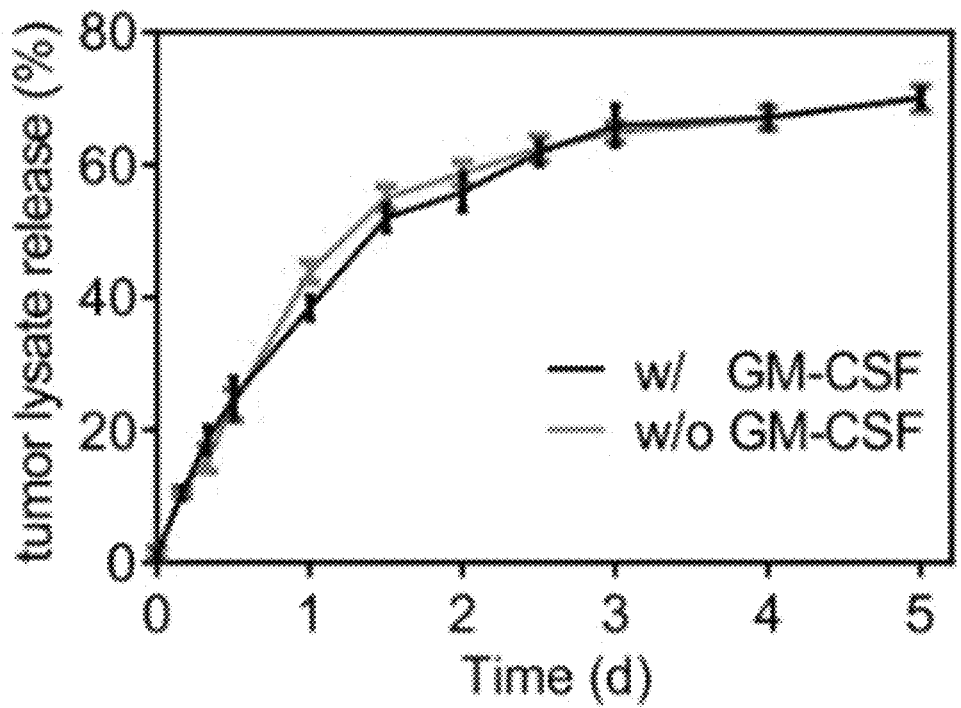
Figure 12A:
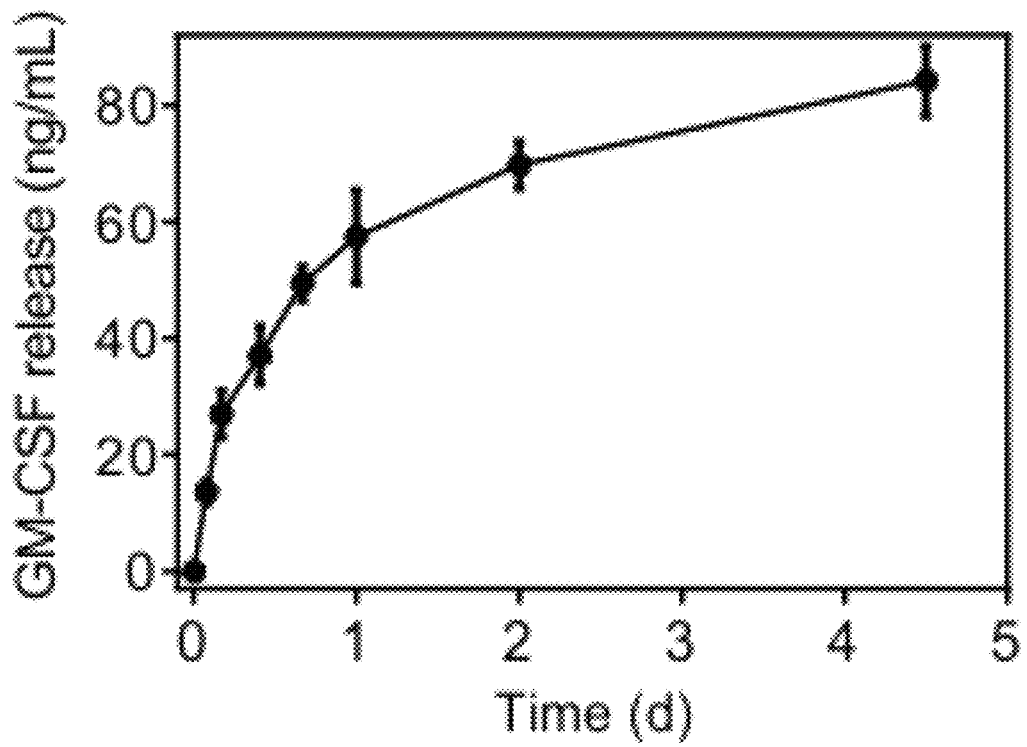
FIGS. 12A-12D demonstrate the in vitro release profiles of GM-CSF and tumor lysate proteins. Profiles of (A) in vitro collective release and (B) bioactivity of GM-CSF from MN-array applicators over time. The collective release of (C) GM-CSF and (D) tumor lysate proteins in buffer solution with 10 min/day NIR treatment of MN-array applicator over time. Data points represent mean±SD (n=3). Error bars indicate SD. Statistical significance was calculated by the Student t-test (NS. P>0.05).
Figure 12B:
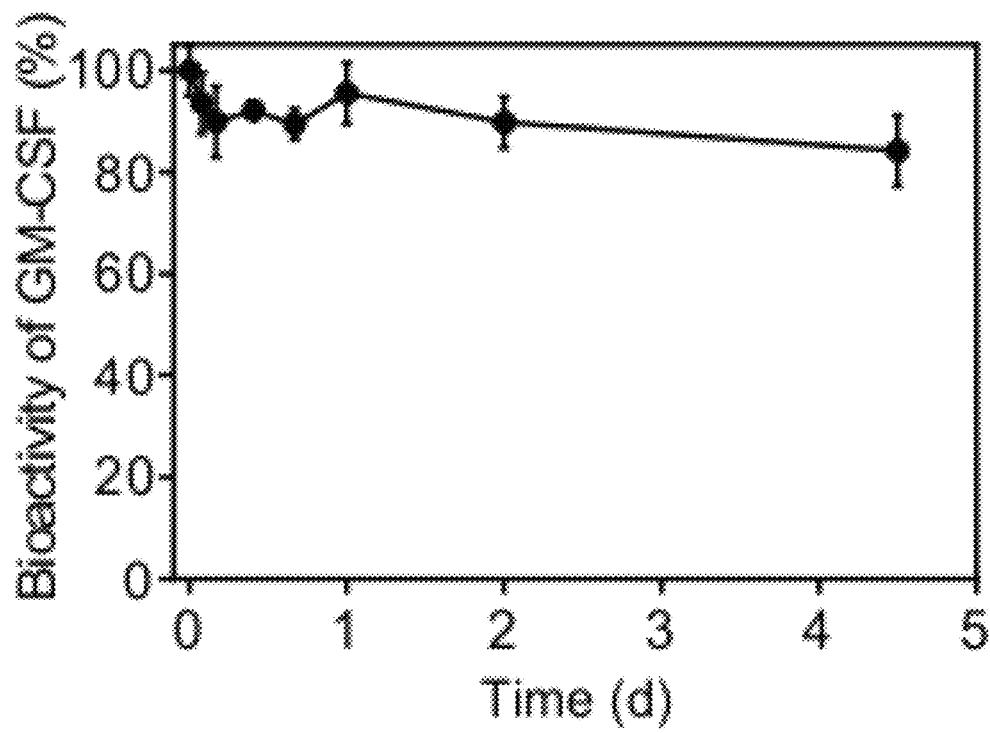
Figure 12C:
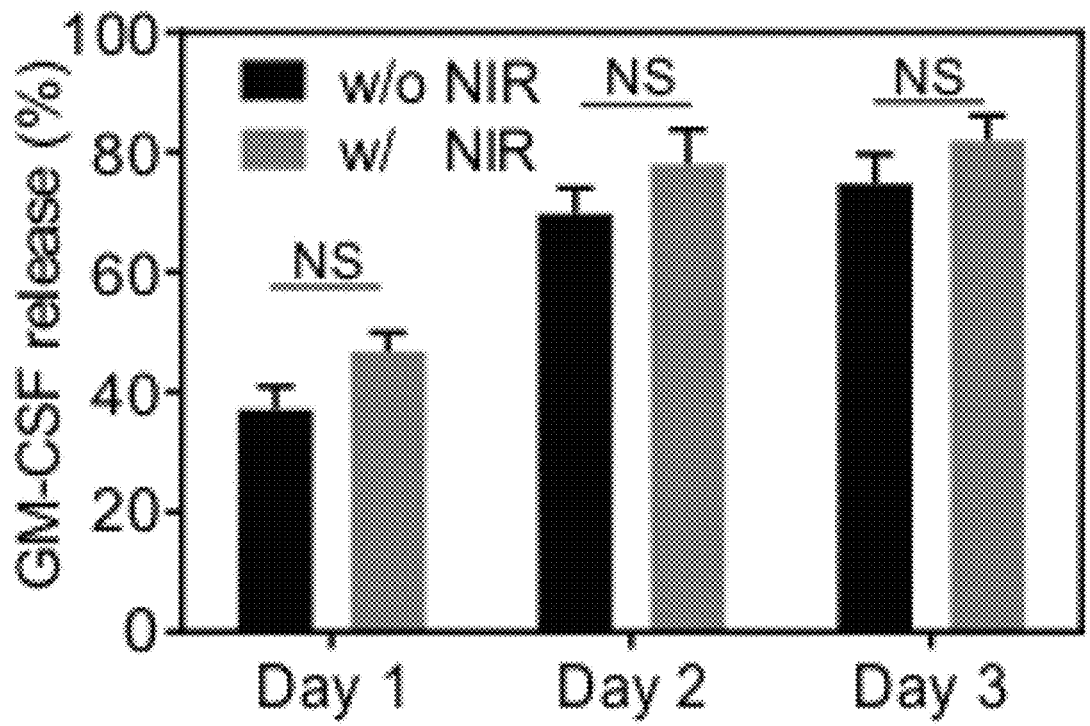
Figure 12D:
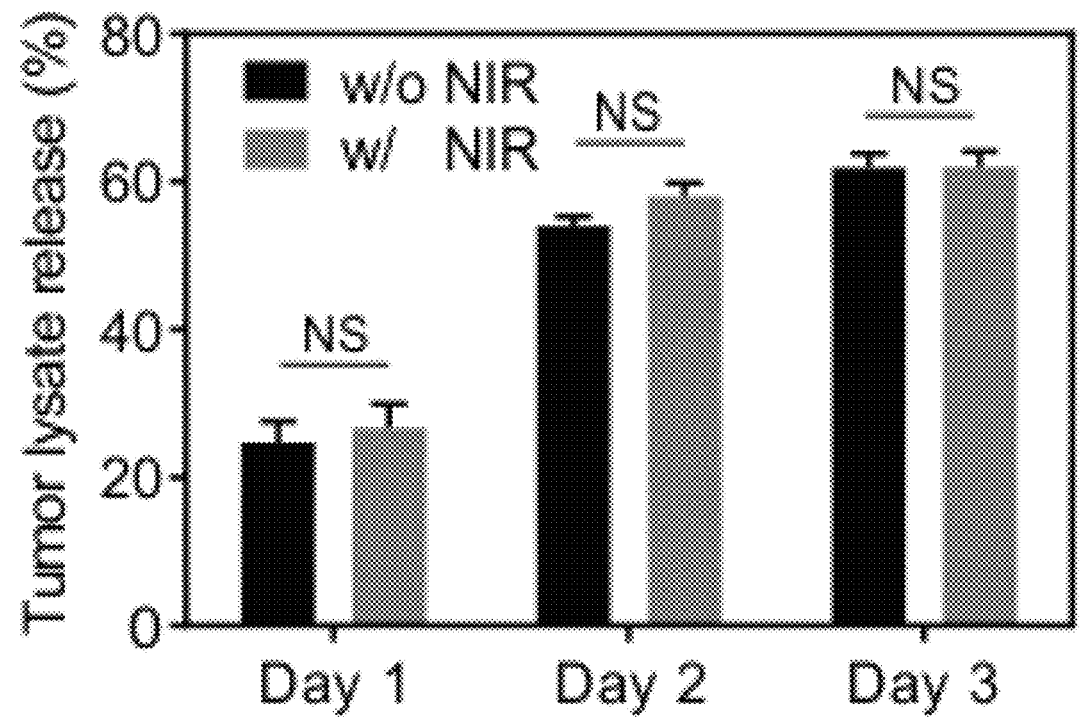
Figure 13:
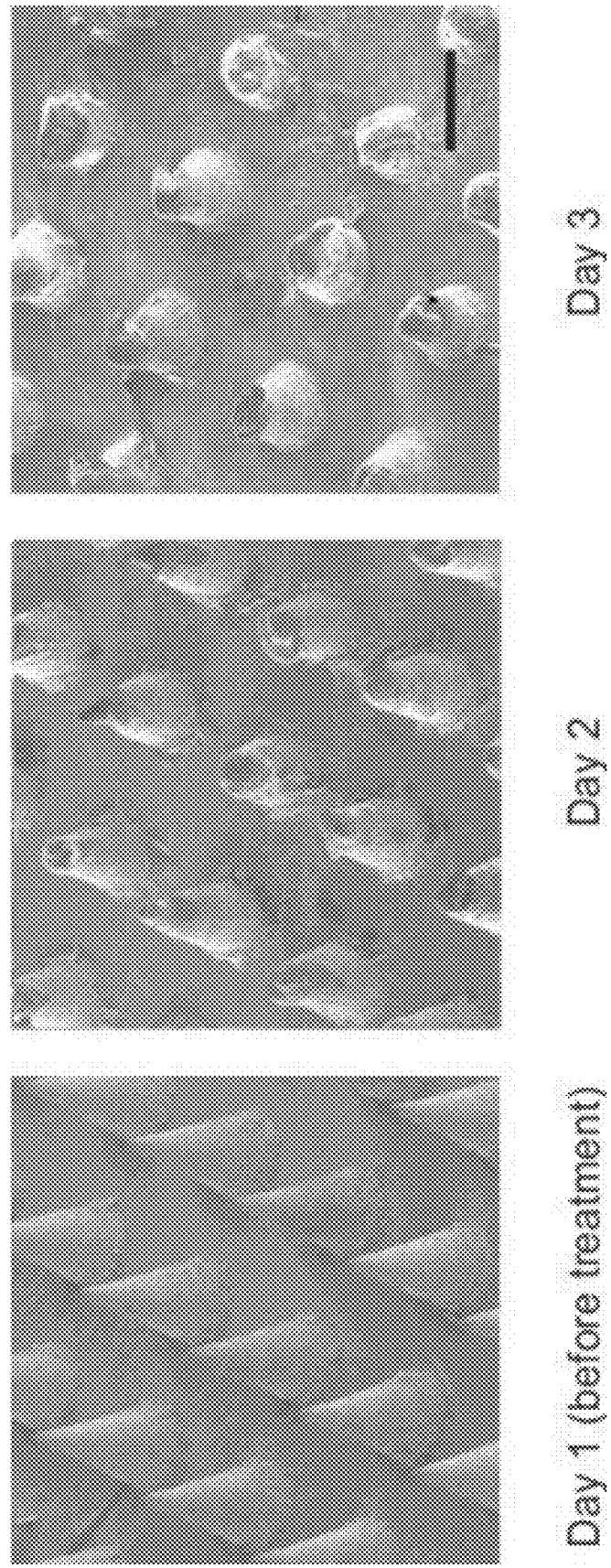
FIG. 13 includes representative scanning electron microscope images of MN-array applicators after insertion into the mouse skin assessed on days 1, 2 and 3 (scale bar: 400 μm).

Example 2: In vitro activation of DCs in response to MN vaccine. GM-CSF that serves as a potent cytokine for DC recruitment and activation was physically encapsulated into MN tips by crosslinking methacrylated hyaluronic acid upon ultraviolet irradiation. It was found that 60% of the bioactive GM-CSF was released from MN within 48 hours (FIGS. 12A-12B), while sustained release of the tumor lysate protein was observed over five days (FIG. 2D). Incorporation of the NIR treatment did not alter the release profiles of GM-CSF and tumor lysate (FIG. 12C-12D). Scanning electron microscopy images of vaccine MNs showed gradual dissociation of tips overtime (FIG. 13).

Figure 2E:
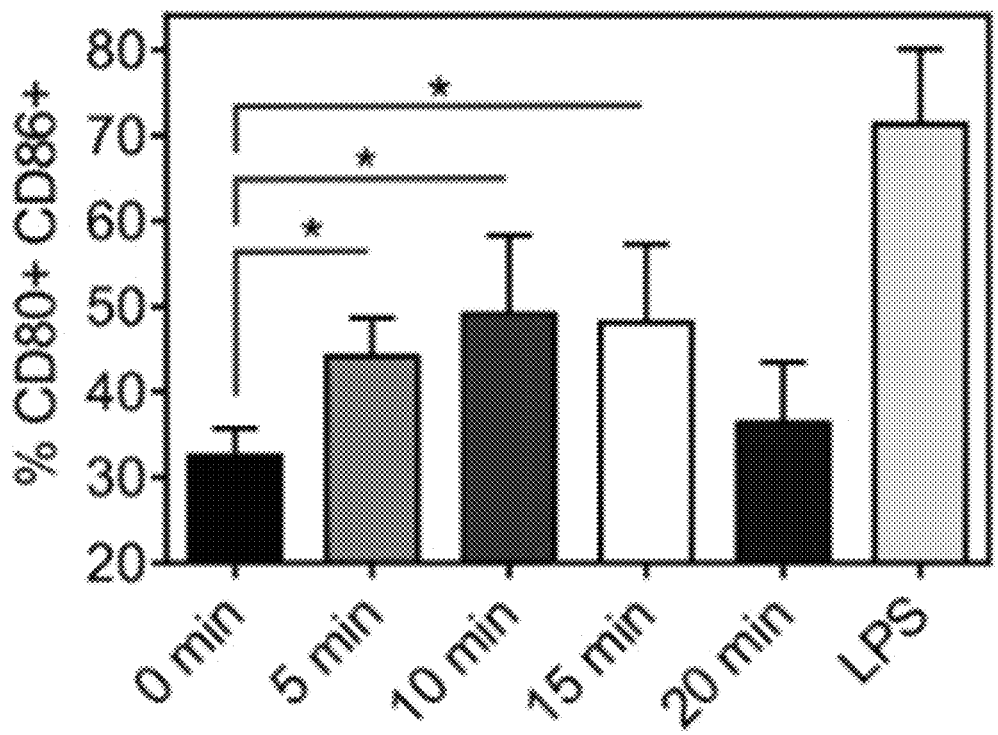
Figure 2F:
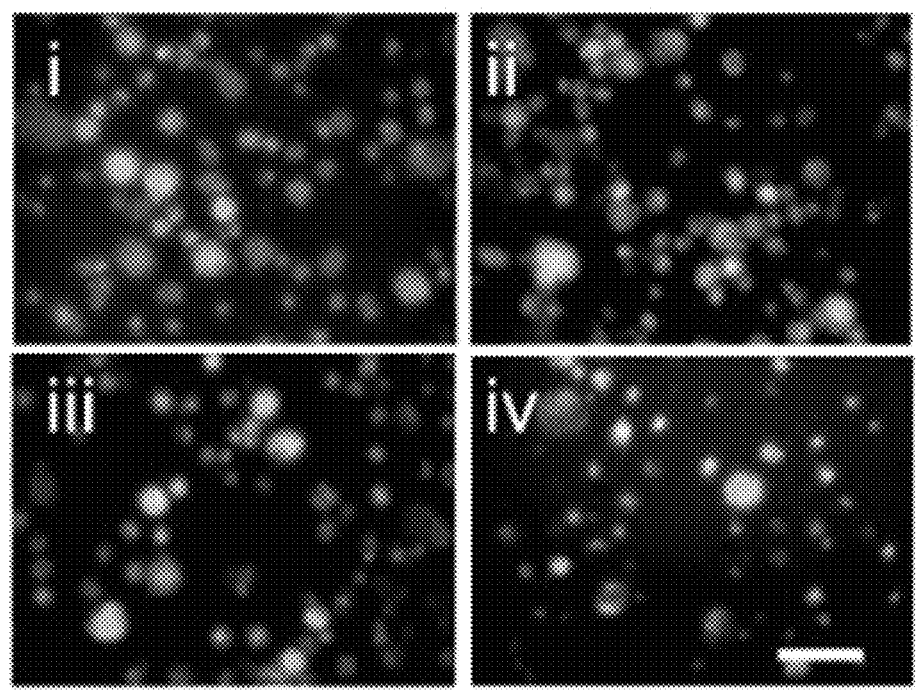
Figure 2G:
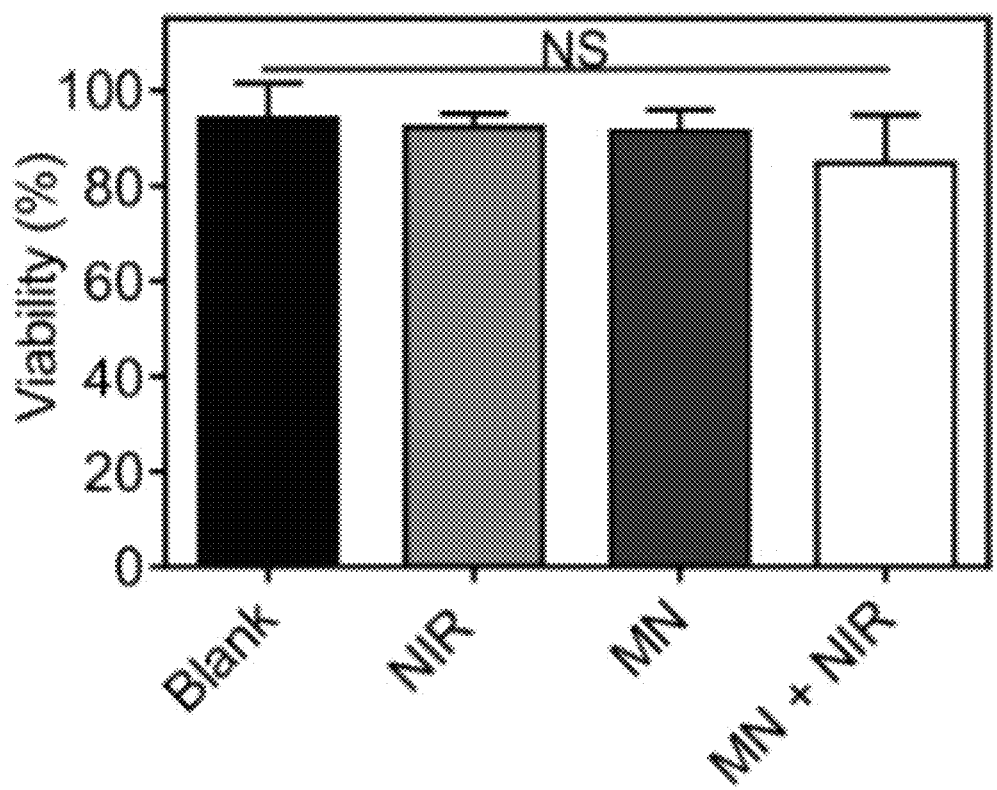
Figure 14A:
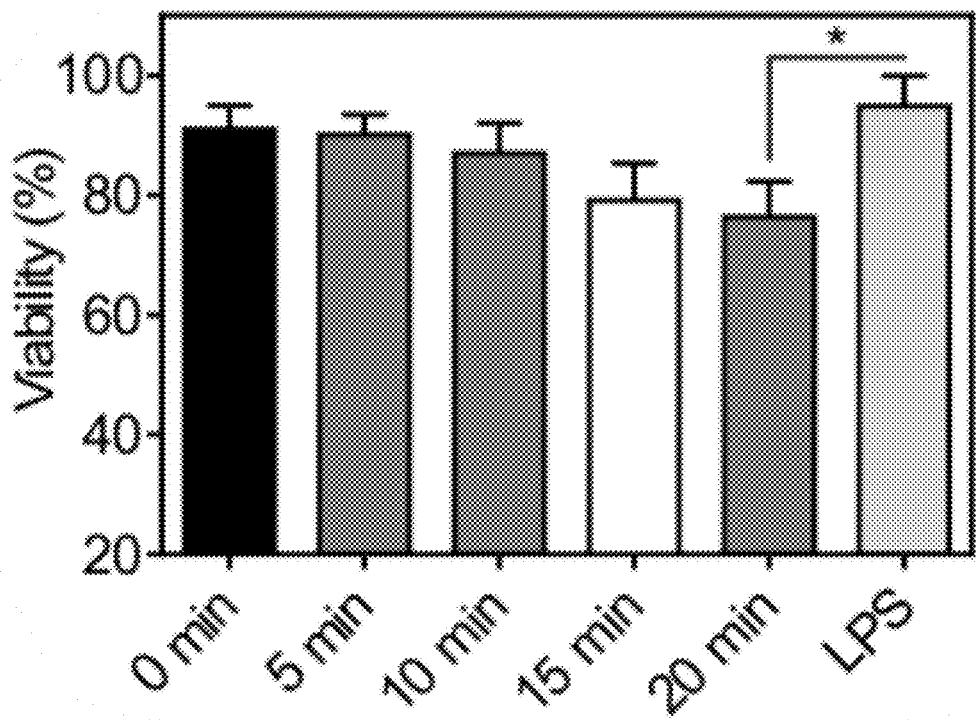
FIGS. 14A-14B evaluate DC function after in vitro activation. (A) DC viability measured by Live/Dead assay. (B) Cytokine interleukin 12 (IL-12) concentration in cell supernatants. The DCs were treated with MNs loaded with tumor lysate or lipopolysaccharide (LPS) and GM-CSF and exposed to different time periods of NIR irradiation. Data points represent mean±SD (n=3). Error bars indicate SD. Statistical significance was calculated by the Student t-test (* P<0.05).
Figure 14B:
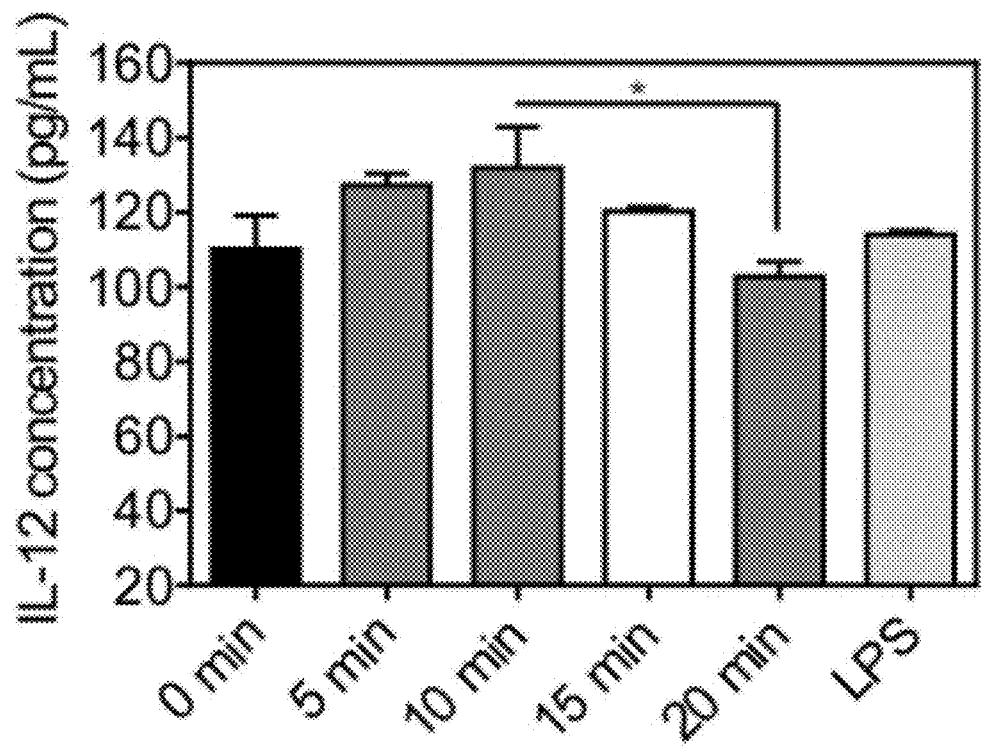
Figure 15:
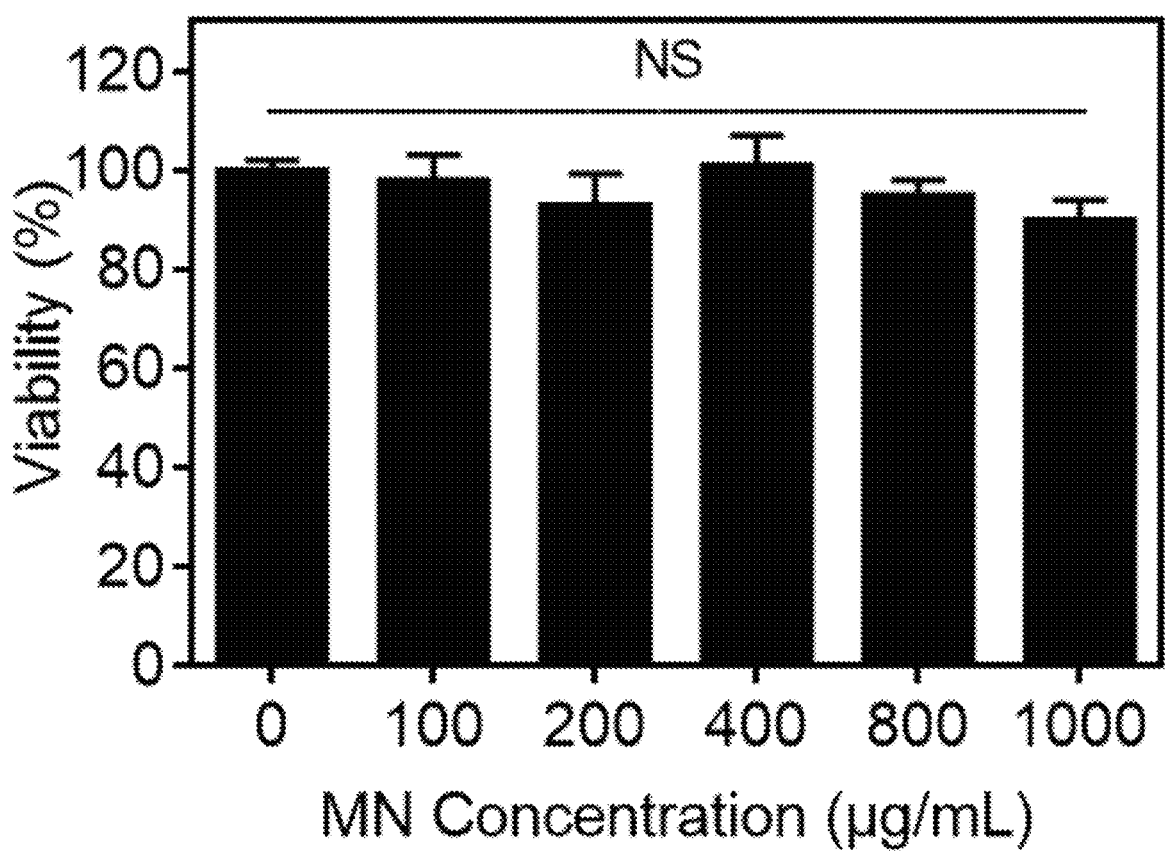
FIG. 15 is a cytotoxicity study of blank MNs. MN-array applicators were re-dissolved and added to B16F10 cells for 24 hrs of incubation. Error bars indicate SD (n=6). Statistical significance was calculated by the Student t-test (NS. P>0.05).

To evaluate whether GM-CSF in MNs provided signaling cues that could efficiently promote DC maturation, bone marrow-derived DCs were exposed to the MN suspension. The percentage of matured DCs (CD80+CD86+) substantially increased from 36.7±2.3% to 48.9±3.1% after treatment with tumor lysate- and GM-CSF-loaded MNs with 10 minutes of NIR laser irradiation (FIG. 2E). The effect of varying NIR laser irradiation time on the activation of DCs was also measured. Ten minutes of NIR irradiation allowed optimal DC activation as compared to samples treated with 5 or 15 minutes (FIG. 2E). Only 20 minutes of NIR exposure slightly impaired DC viability and functionality (FIG. 14). DCs in all other experimental conditions of either MN suspension or 10 minutes of NIR irradiation exhibited high viability (FIGS. 2F-2G and FIG. 15).

Figure 3A:
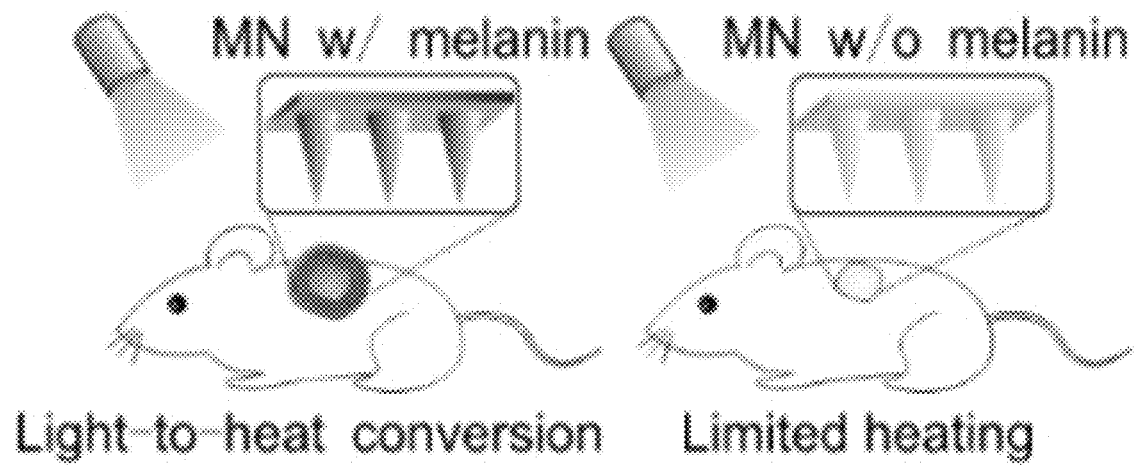
FIGS. 3A-3G demonstrate that MN applicators confer protective innate and adaptive immunity. (A) Schematic illustration of MN cancer immunotherapy. (B) Characterization of the MNs after insertion. (i) Photo of mouse dorsum skin (the area within the red line) that was treated transdermally with one MN applicator and (ii) Fluorescence signals of Cy5.5-labeled MN-array applicator over time. (C) Surface temperature changes of individual animal after MN insertion into the skin measured by an infrared thermal camera. (D) Schematic representation of the B16F10 vaccine tumor model. (E) Average tumor volumes in treated mice after tumor challenge. (F) Kaplan-Meier survival curves for treated and control mice. Data points represent mean±SD (n=8). Error bars indicate SD. Statistical significance was calculated by the Student t-test and Log-rank test (* P<0.05;  P<0.01; * P<0.001). (G) In vivo bioluminescence imaging of the B16F10 melanoma in different experimental groups and at different time points after tumor challenge. Shown were three representative mice per treatment group. The tumor growth in E, F and G was measured 10 days post tumor cell inoculation.
Figure 3B:
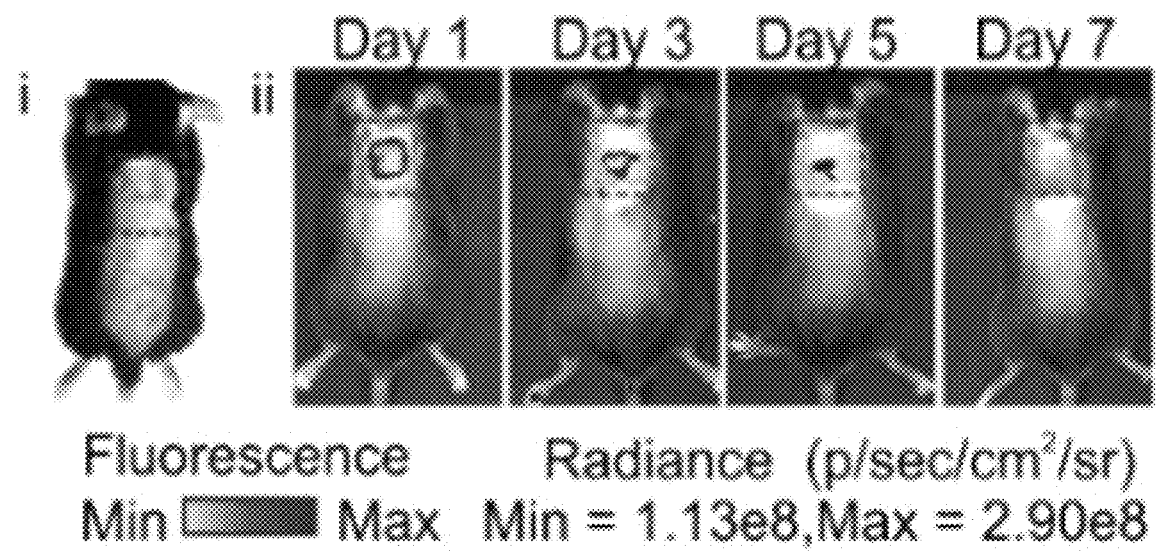
Figure 16A:
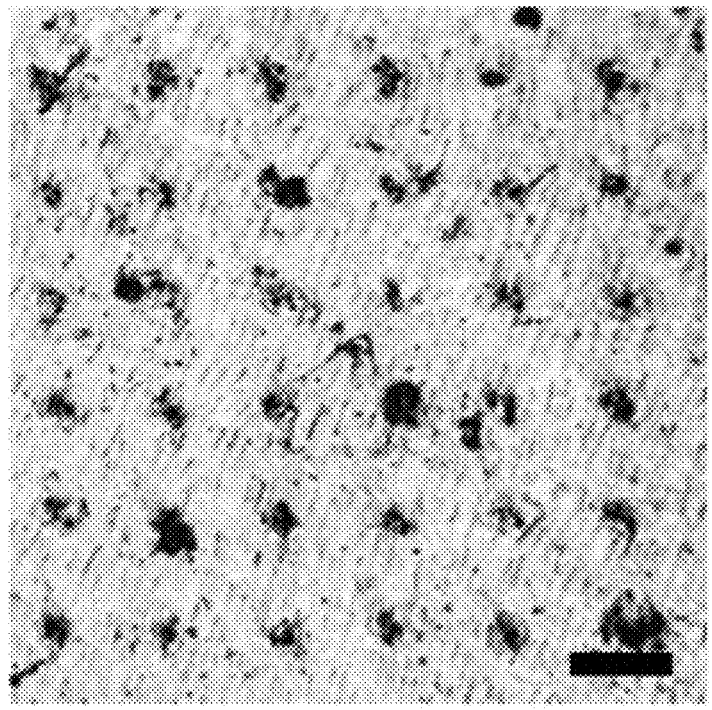
FIGS. 16A-16B characterize skin after MN insertion. (A) Image of the trypan blue and (B) H&E staining showing the penetration of the MNs into the mouse skin (scale bar: 200 μm). The region where the MN insertion took place is indicated by the black dashed line.
Figure 16B:
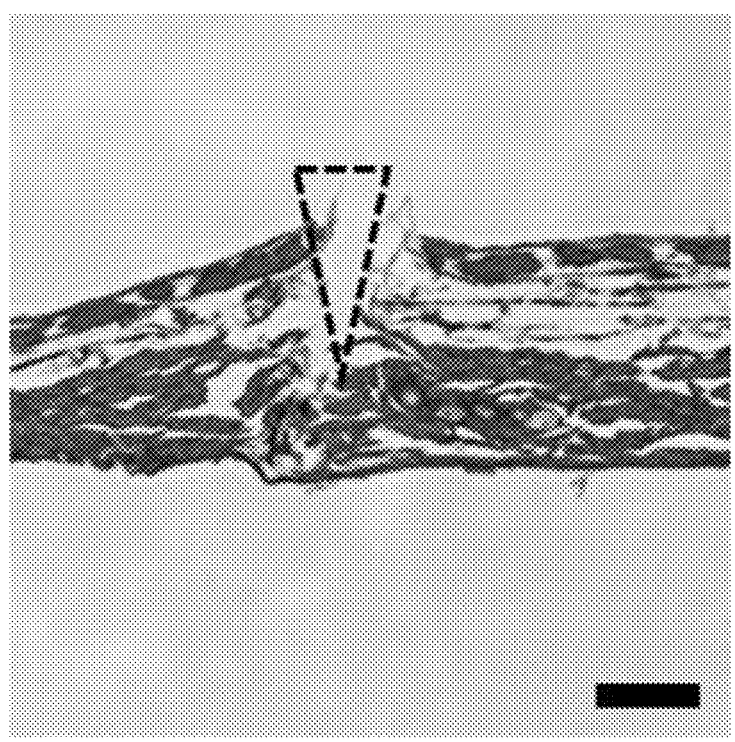

Example 3: In vivo efficacy of MN-mediated immunization upon NIR. In order to characterize the in vivo efficacy of MN-based immunization, C57BL/6J mice were treated transdermally with photo-responsive MN applicators loaded with B16F10 whole tumor lysate containing 1.5 mg extracted protein. The magnitude and duration of the immune response were measured after NIR irradiation and subsequent tumor challenge (FIG. 3A). MN applicators were applied on the mice skin of the caudal dorsal area for approximately 10 minutes and further affixed using the Skin Affix surgical adhesive. Staining with trypan blue and hematoxylin and eosin (H&E) indicated successful penetration of MNs in the excised skin (FIG. 16). The transdermal applicator remained in the skin for at least five days (FIG. 3B). Localized NIR irradiation was then delivered on the MN region for 10 minutes daily for five days (MN+NIR). Control mice were either treated with an MN applicator without NIR irradiation (MN), MN applicator loaded only with melanin (melanin) or MNs containing only hyaluronic acid with NIR irradiation (blank).

Figure 3C:
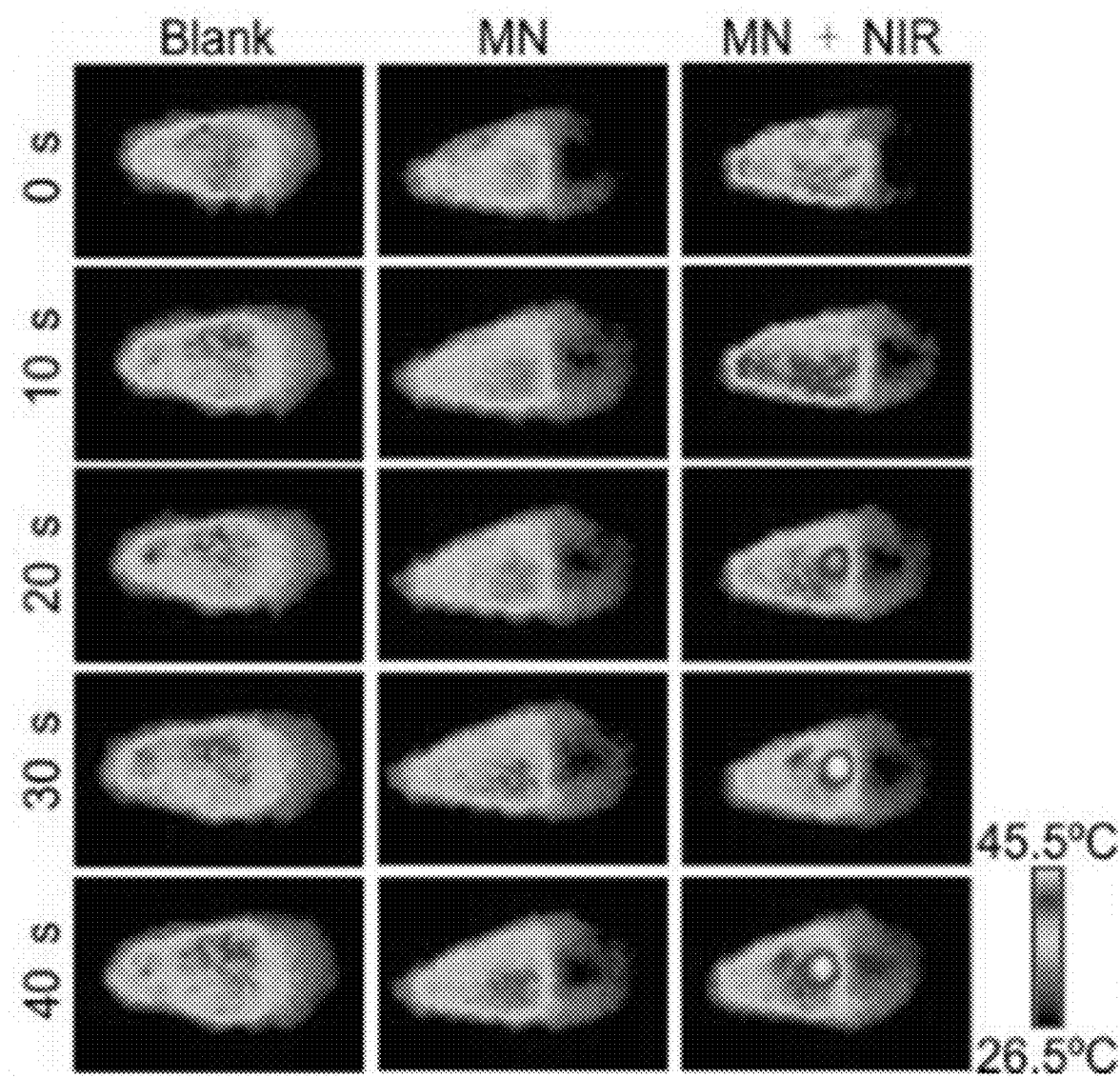

Temperature changes in the regional skin surface after vaccine MN insertion were recorded in real time using an infrared thermal camera. Light-to-heat transduction upon NIR irradiation caused a local heating effect observed in mice treated with vaccine MNs (FIG. 3C). The melanin in the applicator mediated the transdermal heating at temperatures between 38° C. and 42° C. within 30 seconds. Mild hyperthermia at the local treated site was similarly observed in mice treated with synthetic melanin-loaded MNs (FIG. 17A). In contrast, mice treated with blank MNs and NIR, and mice implanted with loaded MNs, but without NIR, showed limited variations in skin surface temperature within the normal range of 33-36° C. (FIG. 3C).

Figure 3D:
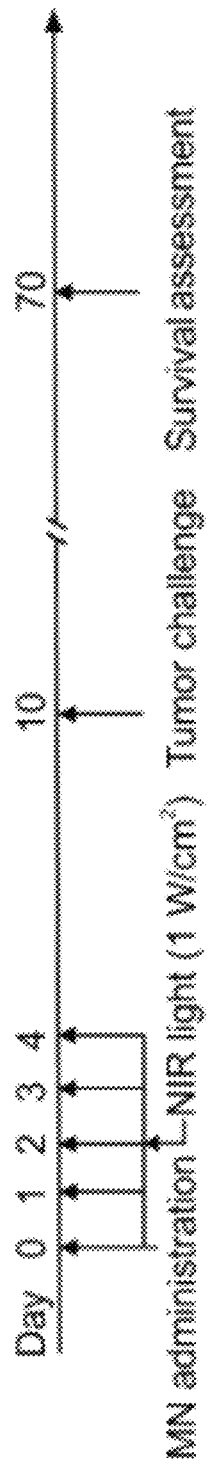
Figure 3E:
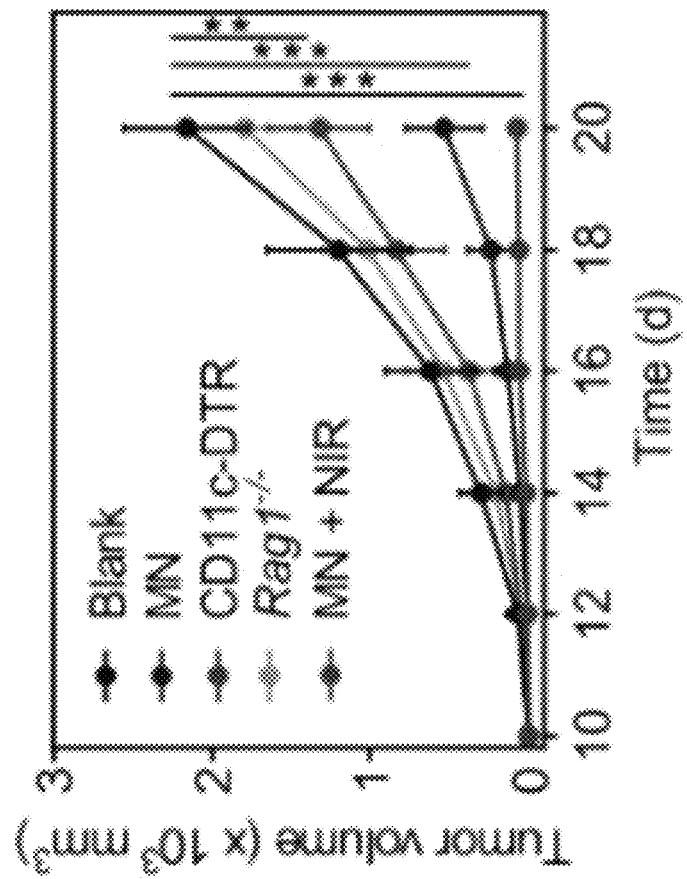
Figure 3F:
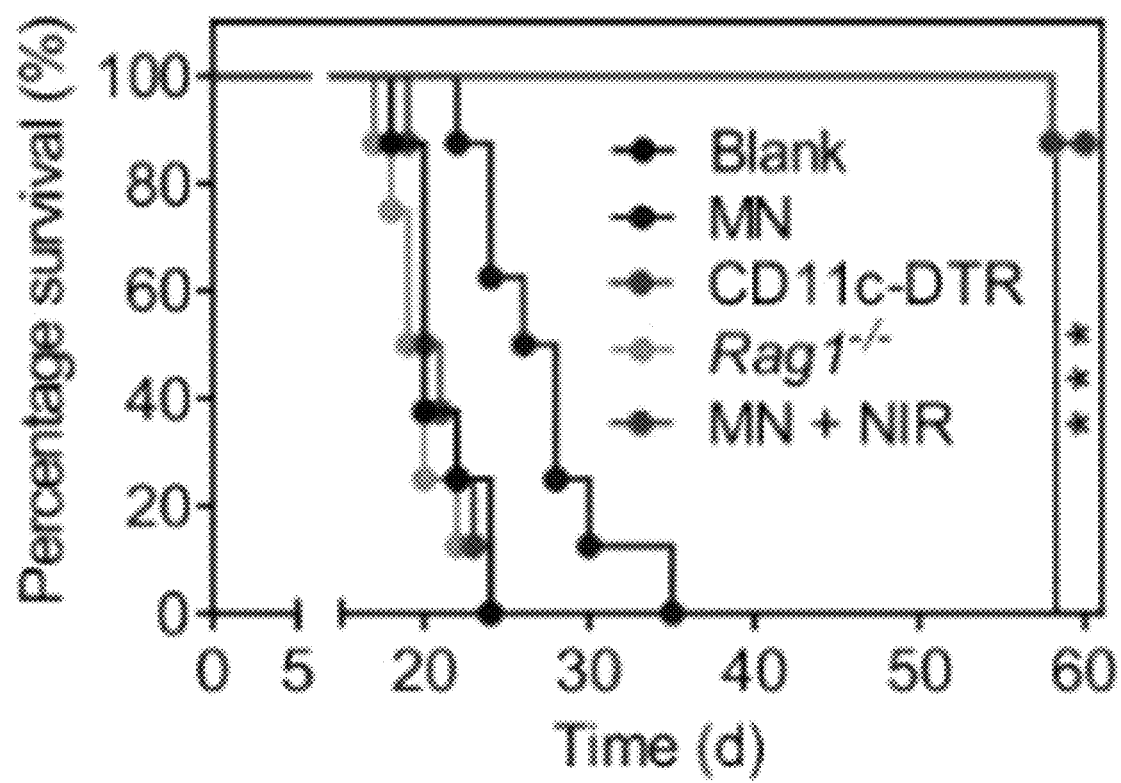
Figure 3G:
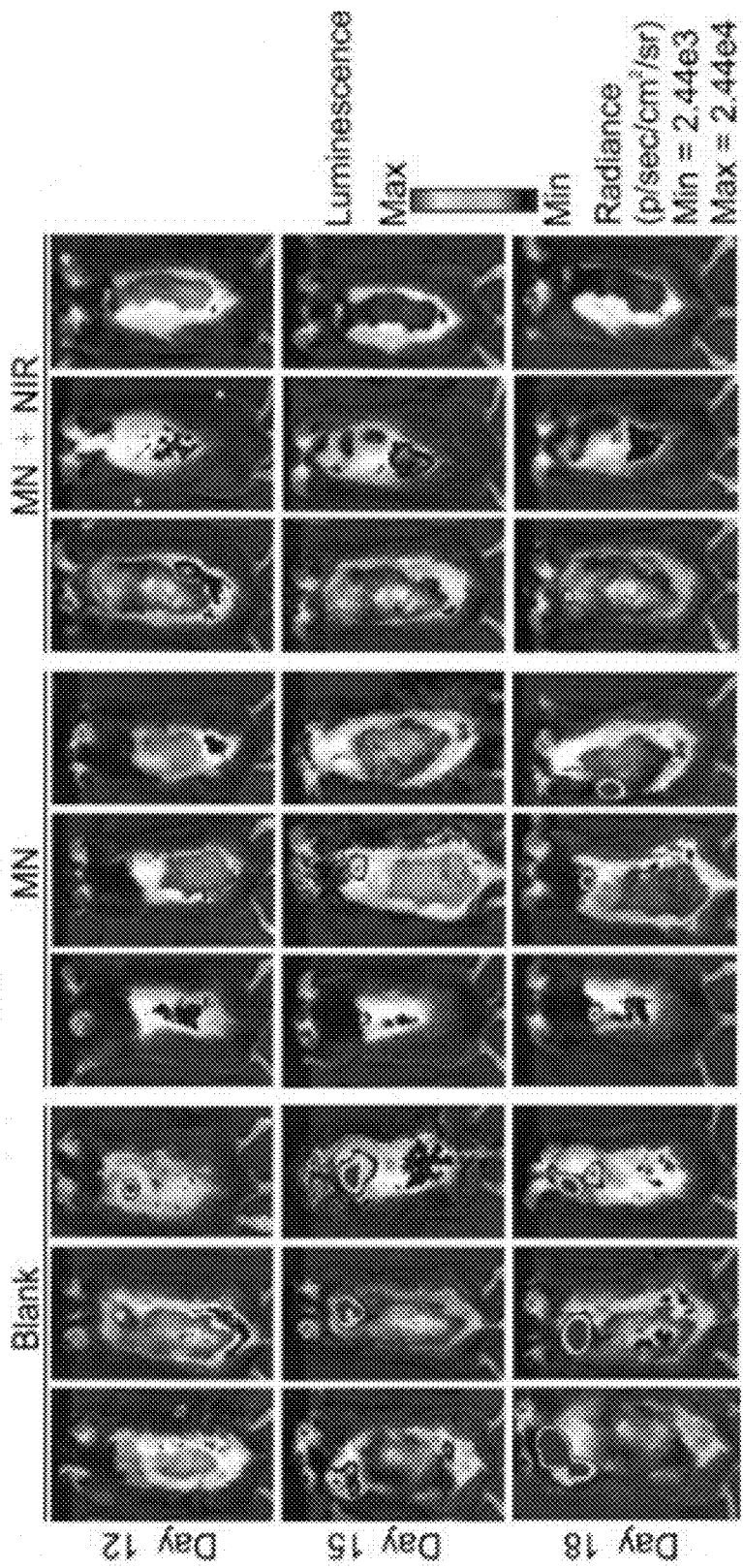

In a prophylactic mouse model, mice were implanted with B16F10 melanoma cells 10 days after vaccination (FIG. 3D). All mice treated with the blank MNs had appreciable tumor growth within 15 days post tumor cell inoculation and required euthanasia by day 25. MNs loaded with melanin and treated with NIR irradiation slightly improved the survival of the mice as some mice survived to day 25 (FIGS. 17B-17C). Similarly, MNs loaded with tumor lysate and melanin, but without NIR irradiation caused tumor protection in 13% of the mice until day 30 (FIGS. 3E-3F). In sharp contrast, mice receiving the combined (MNs loaded with tumor lysate and GM-CSF and NIR irradiation) showed long-term survival with complete tumor rejection in 87% of the treated mice (FIGS. 3E-3F and FIG. 18). Bioluminescence imaging of the B16F10 melanoma-bearing mice confirmed significant inhibition of tumor growth (FIG. 3G and FIG. 19). This was further evidenced by the measurement of tumor weight (FIG. 20) and histologic analysis (FIG. 21A).

The requirement of immune cells for the antitumor effects observed by combined immune composition-based treatments was also assessed. Depletion of CD11c+ DCs in diphtheria toxin receptor (DTR) mice was sufficient to abrogate the antitumor effect of the MN immune composition (FIGS. 3E-3F). Data in Rag1−/− mice deficient in T and B cells showed a significant loss of tumor growth suppression during treatment with combined vaccination (FIG. 18). Selective depletions of CD8+ and CD4+ T cells before combination MN vaccination were also studied. Eliminating CD8+ T lymphocytes showed no significant tumor regression compared to blank control (FIG. 22). When anti-CD4 antibody was given to the mice, there was a decrease (P<0.01) in tumor size in contrast to the control, suggesting the benefit of CD4 T cells to a lesser extent than CD8 T cells for the antitumor response (FIG. 22). The depletion of B cells and NK cells also had deleterious impact on the immune response, while not diminishing the vaccination effect toward tumor challenge (FIG. 22). Together, these results showed that the MN vaccination was associated with CD11c+ DCs and other immune cells such as T cells, B cells and NK cells.

Figure 4A:
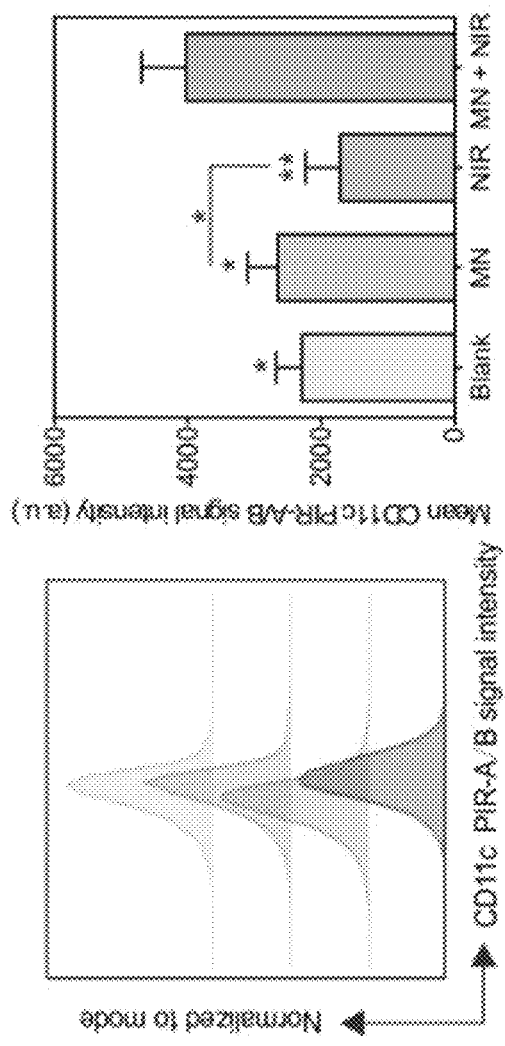
FIGS. 4A-4D demonstrate immune cell recruitment after the NIR-boosted and MN-mediated cancer immunotherapy. (A) Representative quantitative analysis of DCs (CD11c+, PIR-A/B+) infiltrated in the skin three days after treatments as assessed by flow cytometry. The indicated samples were treated with blank MN (blank), vaccine MN (MN), MN loaded with tumor lysate without GM-CSF and treated with NIR (NIR), vaccine MN and treated with NIR (MN+NIR). (B) Representative quantitative analysis of NK cells (CD49b+) in the skin upon transdermal cancer immunotherapy as assessed by flow cytometry. (C) Immunofluorescent staining and quantitative analysis of CD11c+ DCs (scale bar: 100 μm) and (D) CD49b+ NK cells (scale bar: 100 μm). Statistical significance was calculated by the Student t-test (* P<0.05; ** P<0.01). Asterisks indicate significant differences between the MN+NIR group and all other treatment groups. Data points represent mean±SD (n=3). Error bars indicate SD.
Figure 4B:
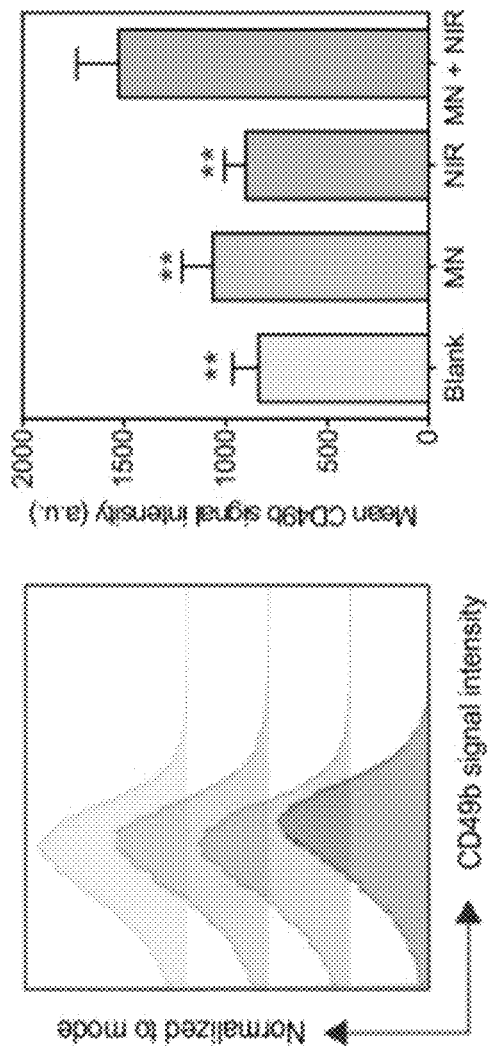
Figure 4C:
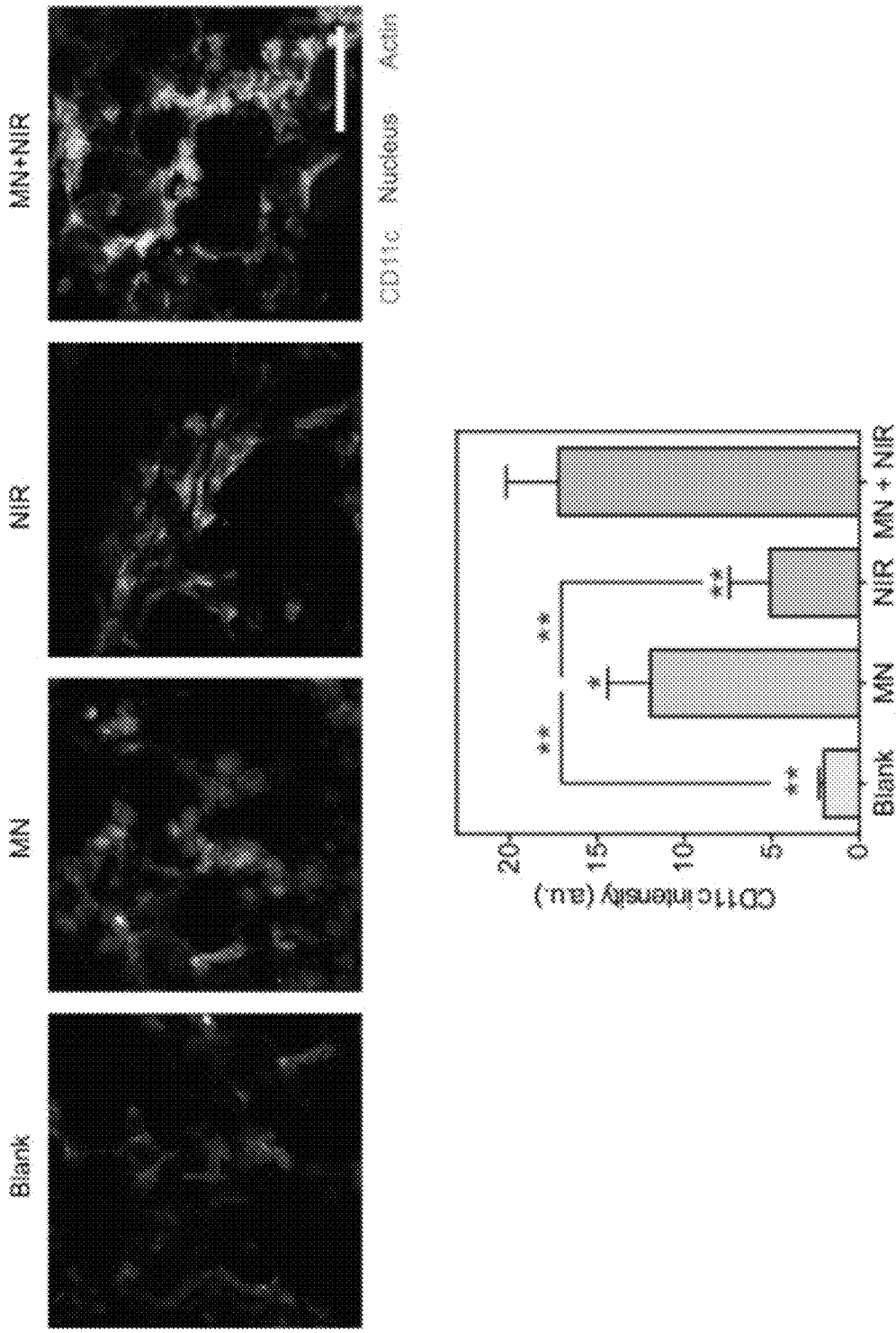
Figure 4D:
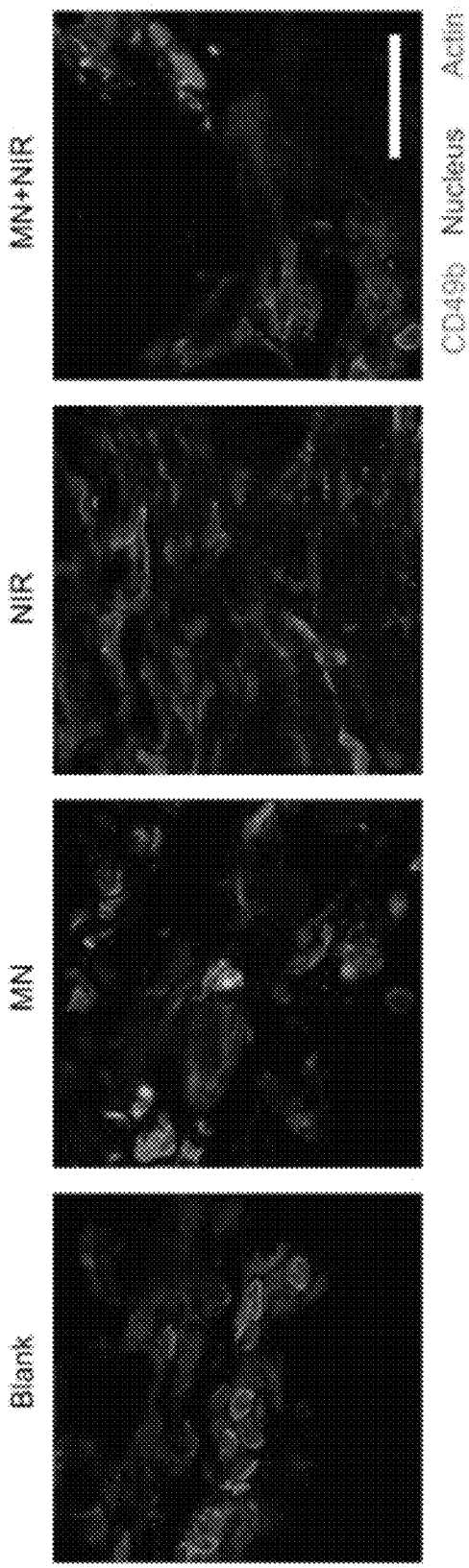
Figure 4D:
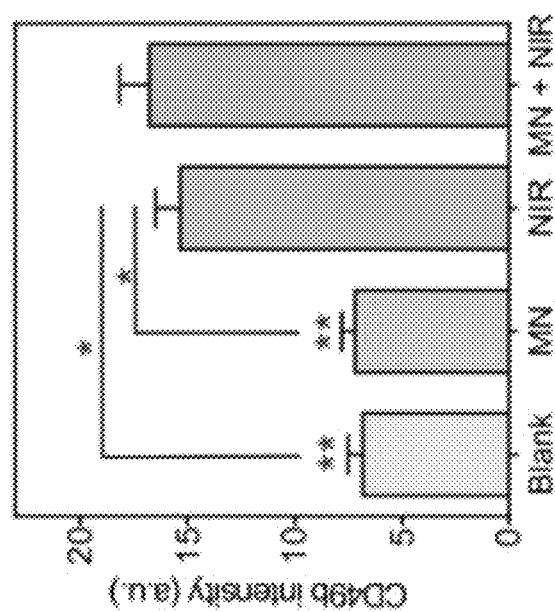
Figure 5A:
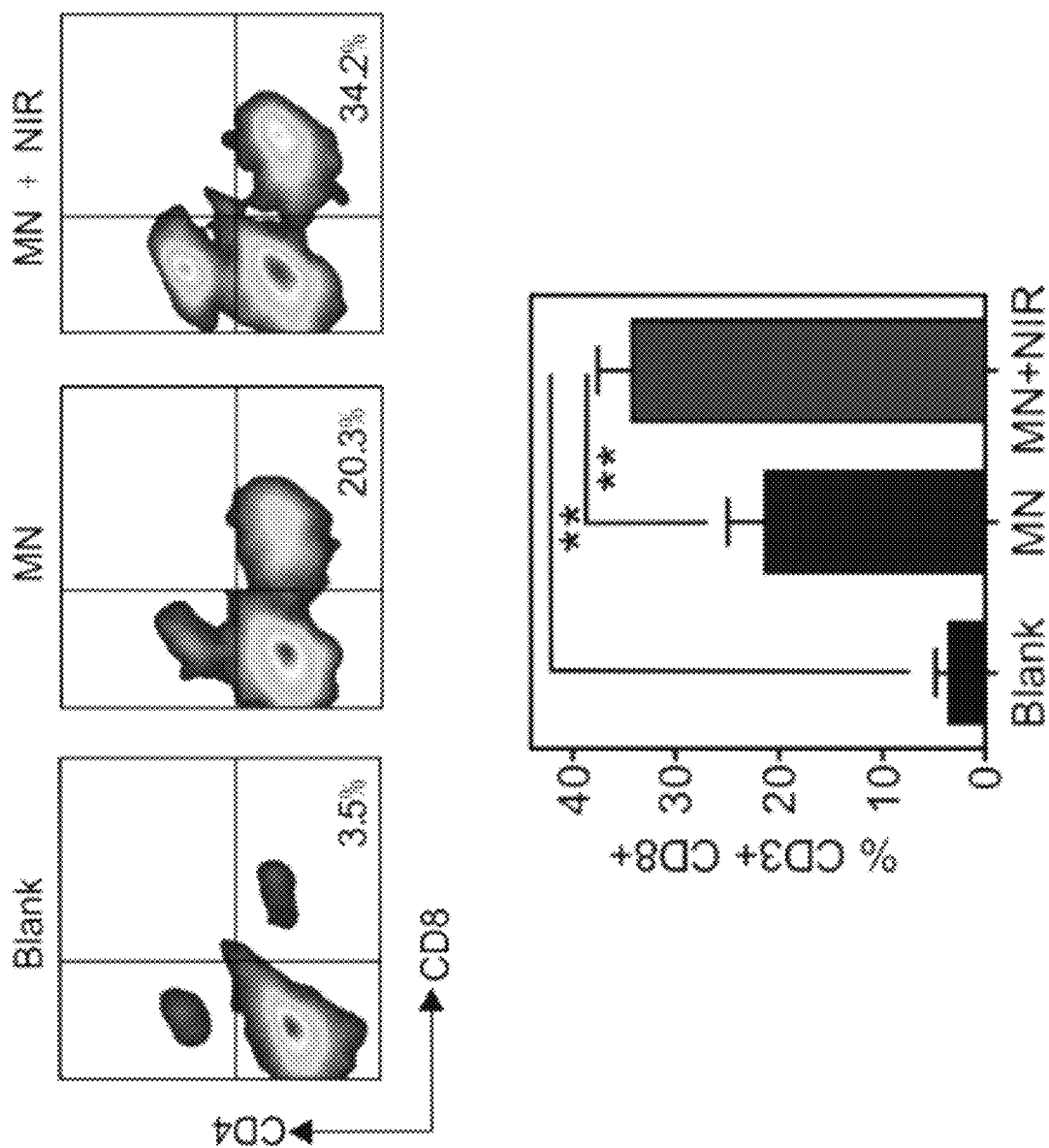
Figure 5D:
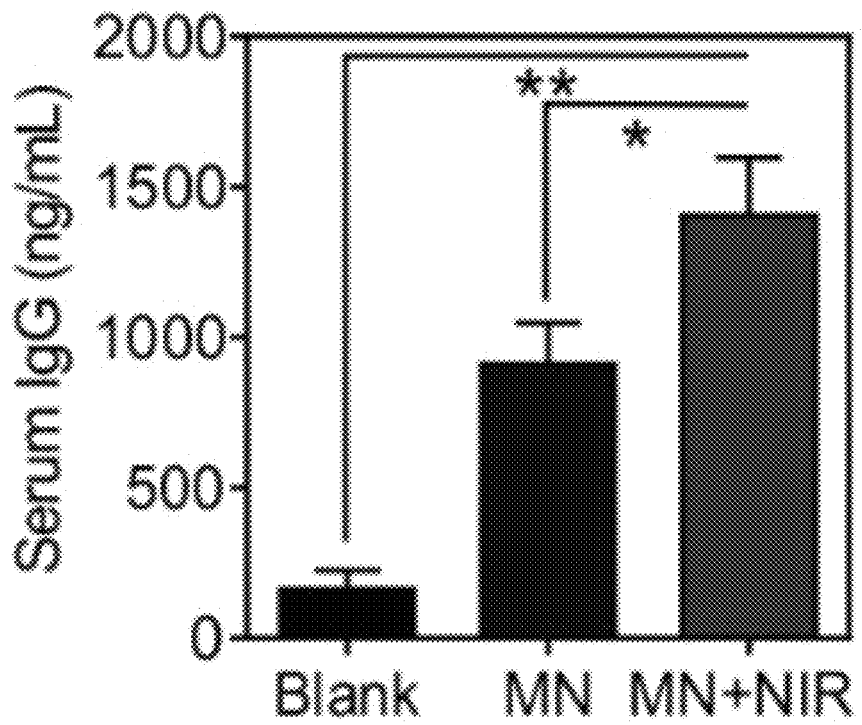
Figure 5E:
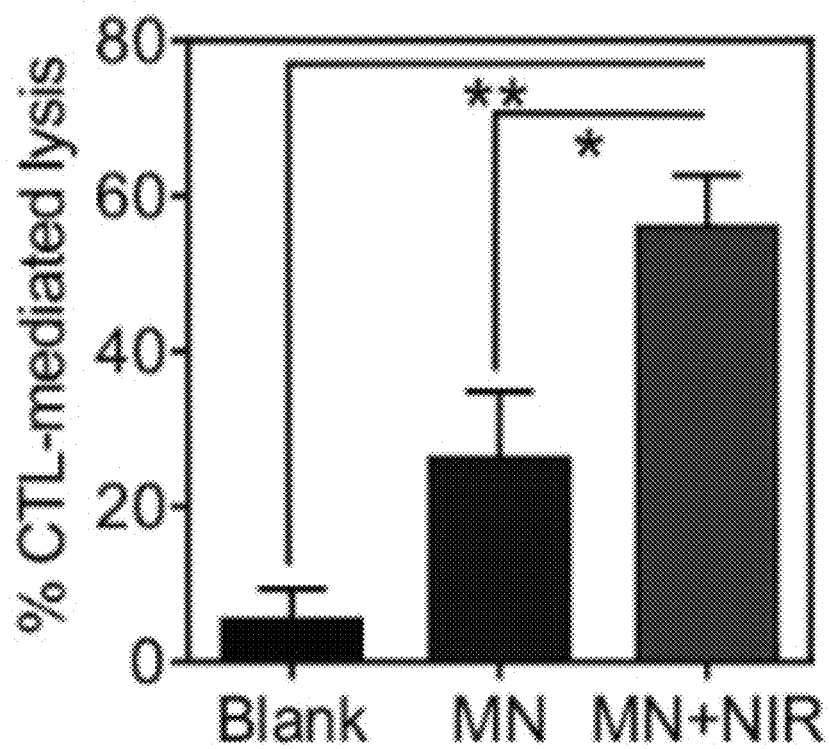

Loading of GM-CSF in the MNs played an important role in the local recruitment of DCs (CD11c+, paired Ig-like receptors of activating (PIR)-A/B+) (FIGS. 4A-4C). Three days after combined vaccination, 5.9-fold increase in accumulated DCs was observed in the skin section compared to mice treated with blank MN. NIR further augmented the effect of GM-CSF-loaded MNs on recruiting DCs (FIG. 4C). Increased localization of NK cells was also observed (FIGS. 4B-4D). In addition, the elevated local microcirculatory blood perfusion observed after NIR and MN treatment could contribute in enhancing the migration of immune cells (Table 2 and FIG. 23). Tumor infiltration by T cells upon treatment was analyzed by flow cytometry on day 15 after tumor inoculation. Approximately 9.8-fold increase in CD8+ T cells was observed in mice receiving the combined vaccination compared to control mice, whereas MN-only group showed 5.8-fold increase (FIG. 5A). Furthermore, staining with H-2Db gp100 tetramers identified B16F10-specific CD8+ T cells in tumors of treated mice. The percentage of tetramer-positive CD8+ T cells was found to be greater in the MN-treated mice compared to control mice lacking immunization (FIG. 24). Mice with combined treatment or MN-only treatment exhibited 1.5- and 1.3-fold increases in activated DCs (CD80+, CD86+), respectively in regional skin as compared to control mice (FIG. 5B). Immunofluorescence staining and in situ cell apoptosis confirmed the results obtained with flow cytometry (FIG. 5C and FIG. 21B). Local immune activation was associated with systemic immune responses. An 8-fold increase in IgG titers was measured in the serum of immunized mice as compared to mice treated with blank control (FIG. 5D). NIR treatment promoted further increase in IgG titers by day 15, and prolonged immune responses compared to control groups (FIG. 25). The in vitro analysis of splenocytes revealed 10-fold higher frequency of T cells responding to B16F10 tumor lysate in mice receiving the combined vaccination (FIG. 5E).

TABLE 2

The measurement of total local microcirculatory blood perfusion of mice receiving different treatments using the Laser Doppler flowmetry.

| Perfusion unit (PU) | Mean | S.D. | Min | Max | Area |
|---|---|---|---|---|---|
| Blank | 76.4 | 23.0 | 40.3 | 150.8 | 1111.7 |
| MN | 80.5 | 27.4 | 45.5 | 150.2 | 1196.7 |
| MN + NIR | 96.3 | 35.2 | 49.5 | 228.0 | 1420.6 |

Figure 5F:
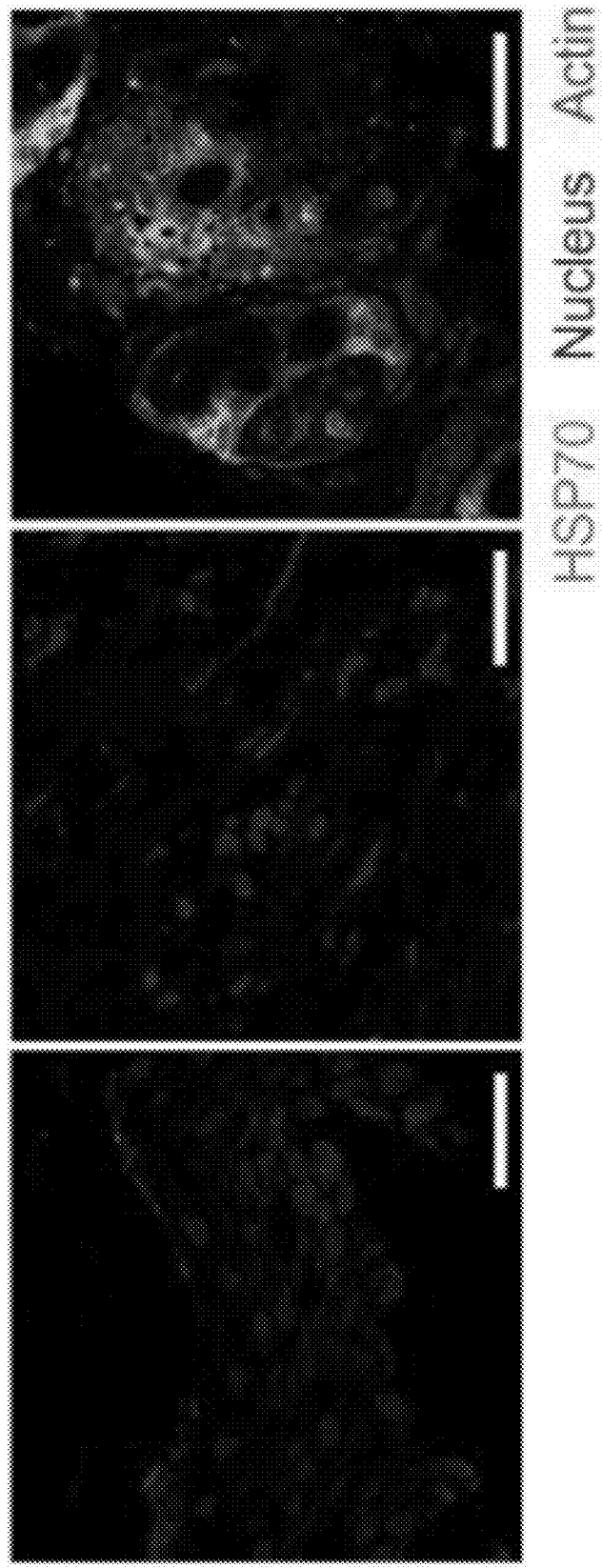
Figure 5G:
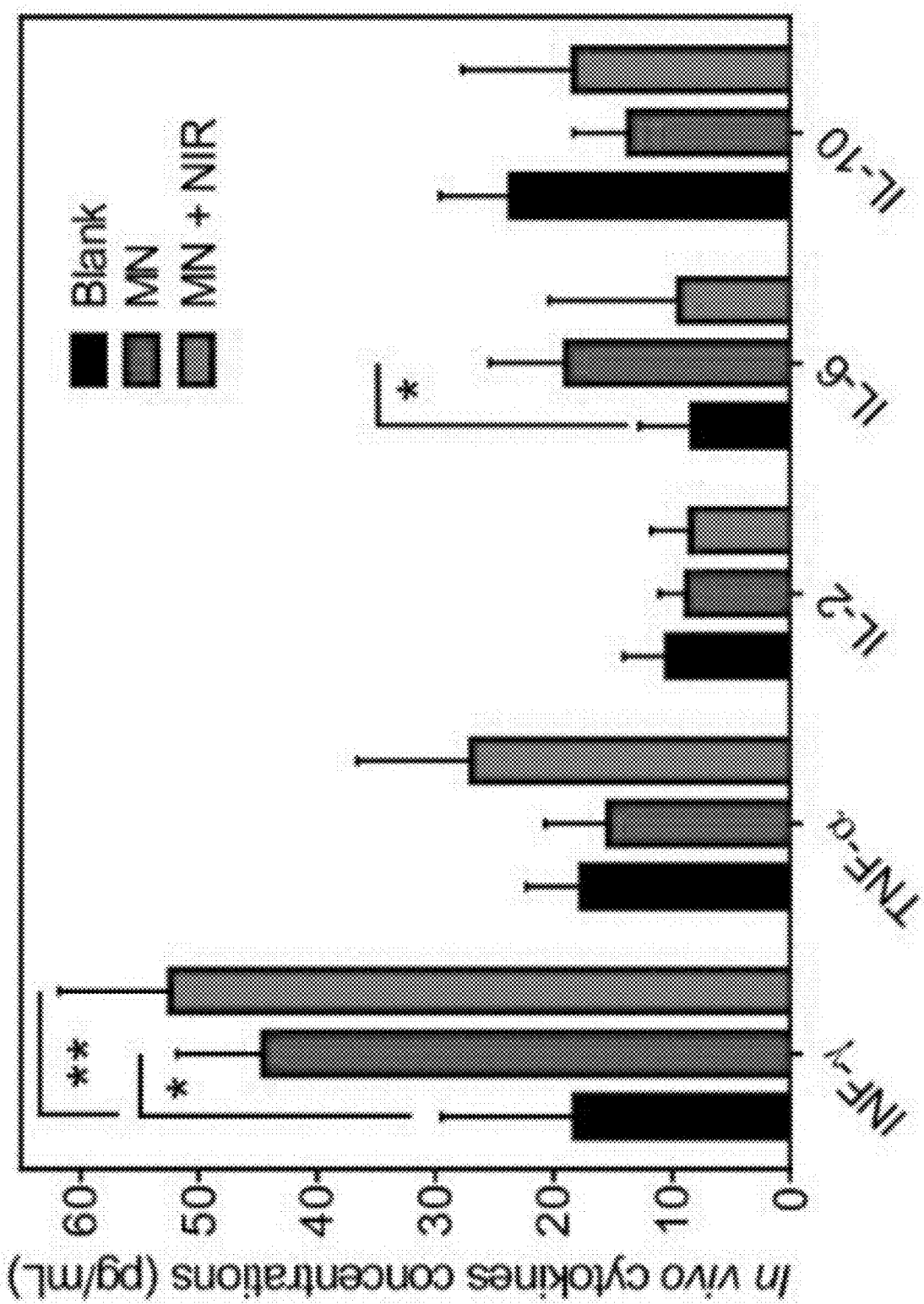

To examine that the light-to-heat transduction induced the production of danger signals and pro-inflammatory cytokines, we first measured local levels of ROS in the MN-treated surrounding tissue by flow cytometry. Samples from mice receiving the combined treatment showed approximately 4-fold increase in ROS levels compared to the untreated group, whereas 1.5-fold increase was observed after the NIR irradiation compared to the MN control (FIG. 26). In line with the elicitation of danger signals, combined vaccination caused the expression of HSP 70 and HSP 90 (FIG. 5F and FIG. 27). Danger signals from the local tissue and the antigenic molecules promote pro-inflammatory cytokine production. Consistent with this effect, we found local increases of interferon-γ (IFN-γ), tumor necrosis factor-α (TNF-α) and interleukin-6 (IL-6) in mice treated with the combined vaccination compared to MN controls (FIG. 5G and FIG. 28).

Figure 6A:
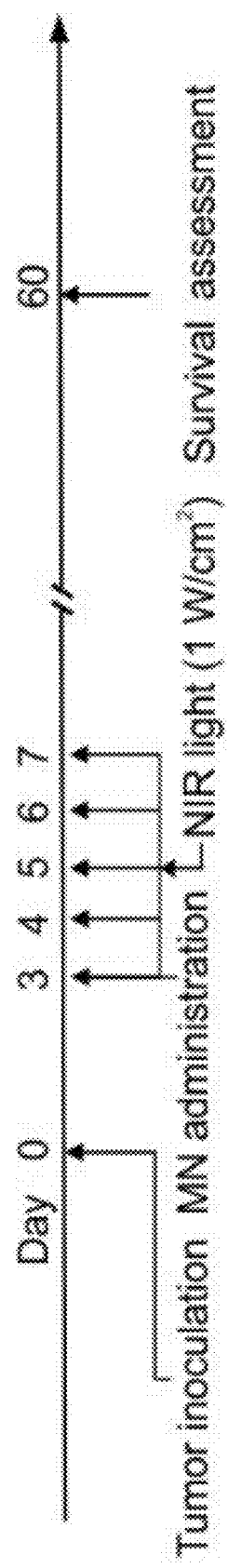
Figure 6B:
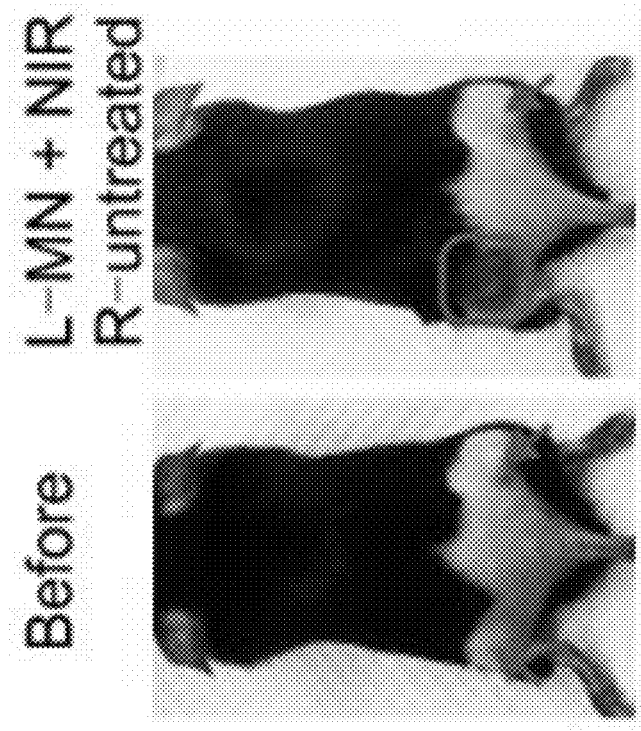
Figure 6C:
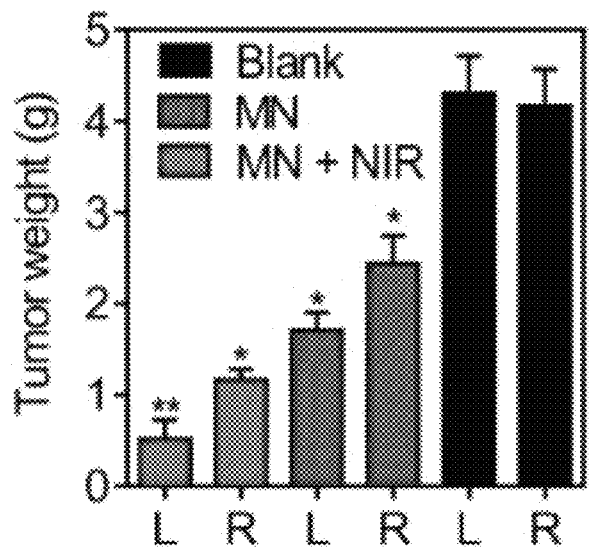
Figure 6D:
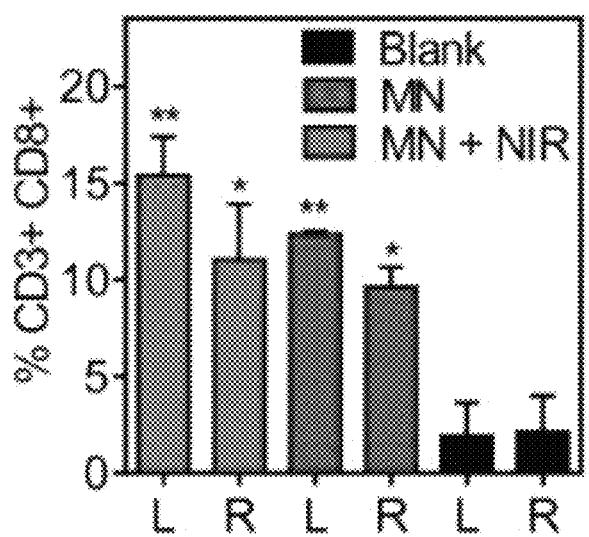
Figure 6E:
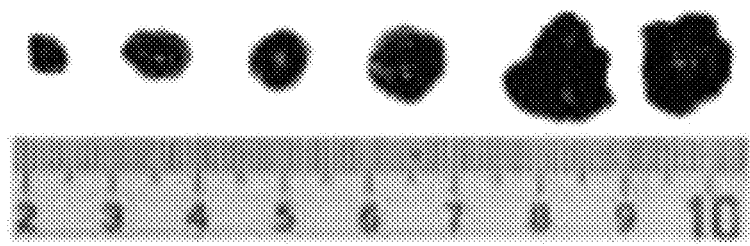
Figure 6F:
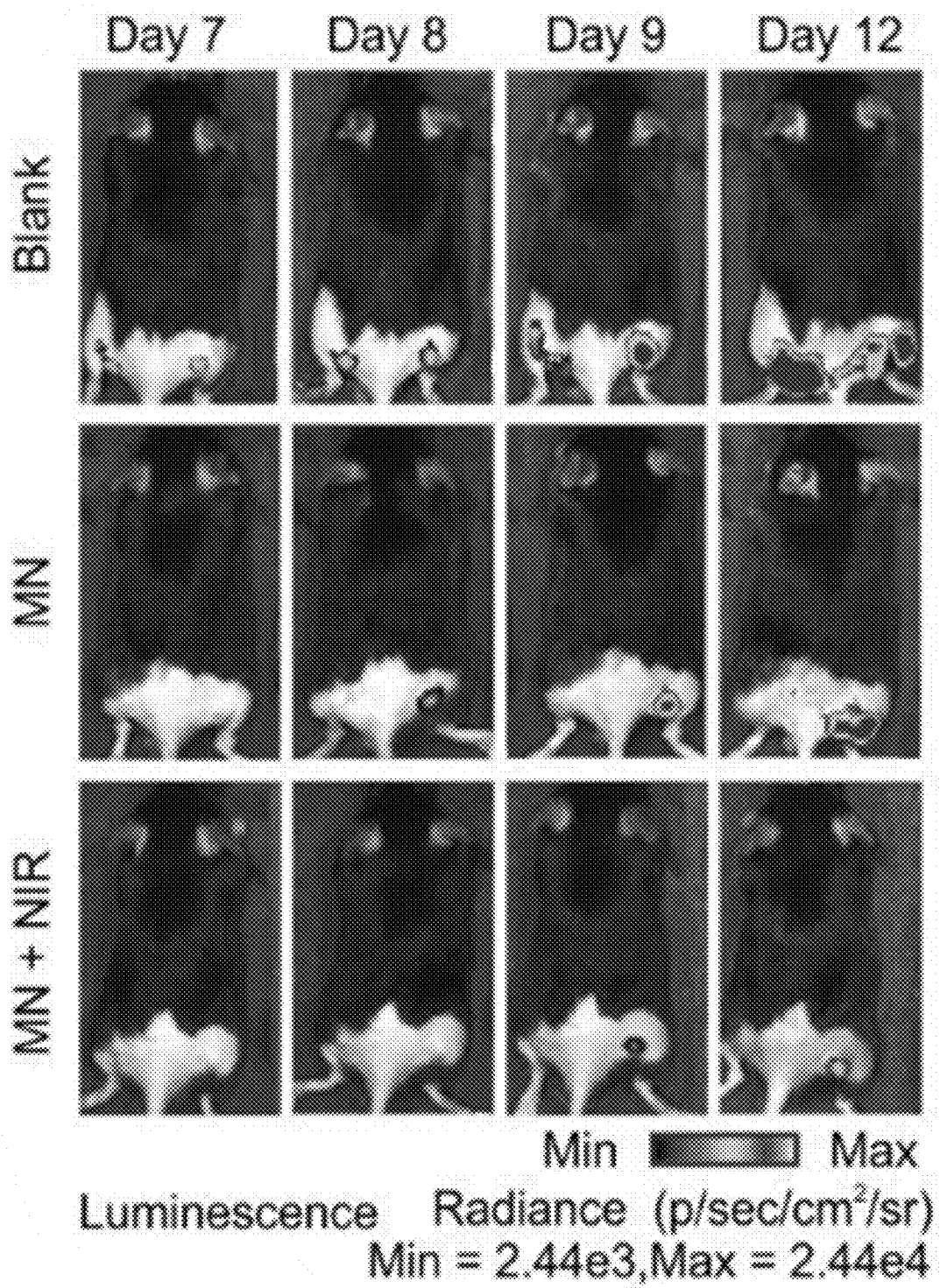
Figure 6G:
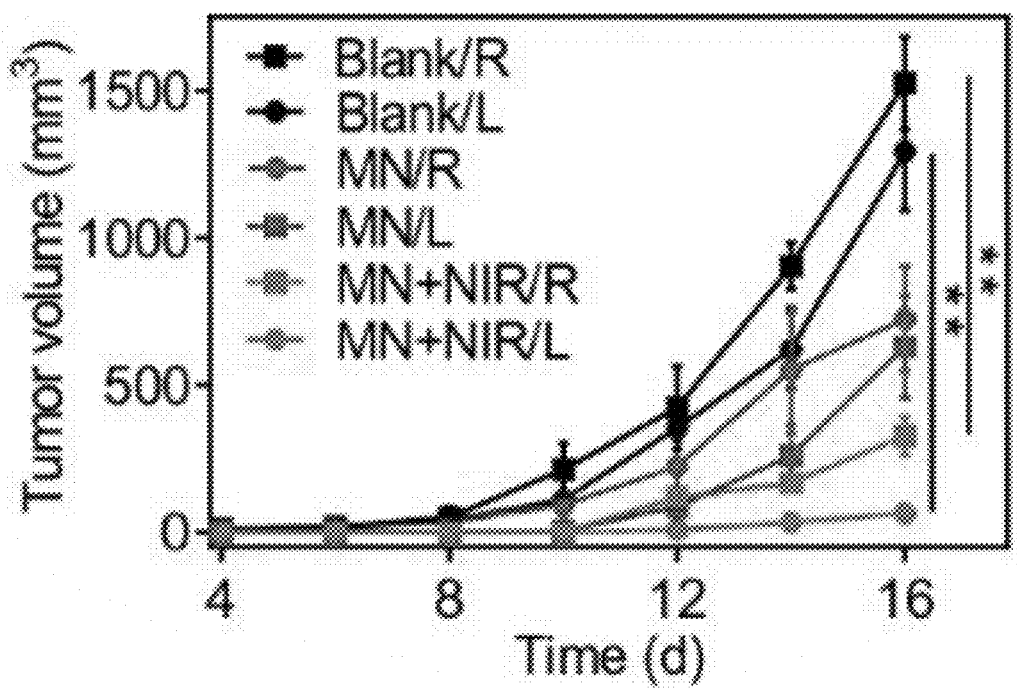
Figure 6H:
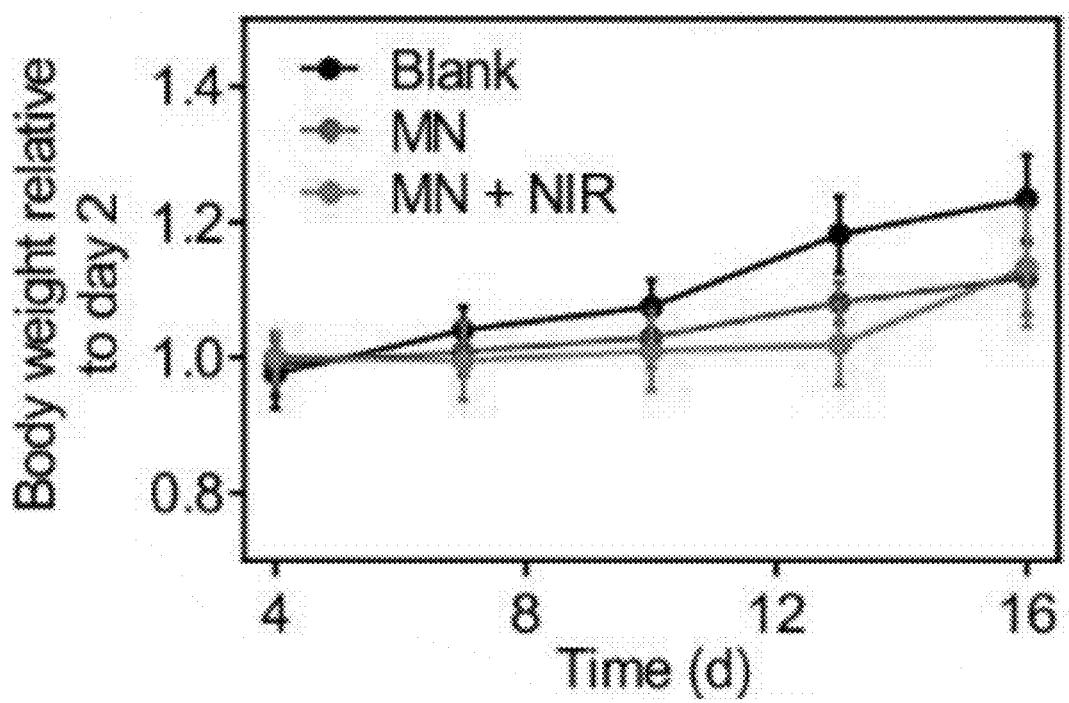
Figure 6I:
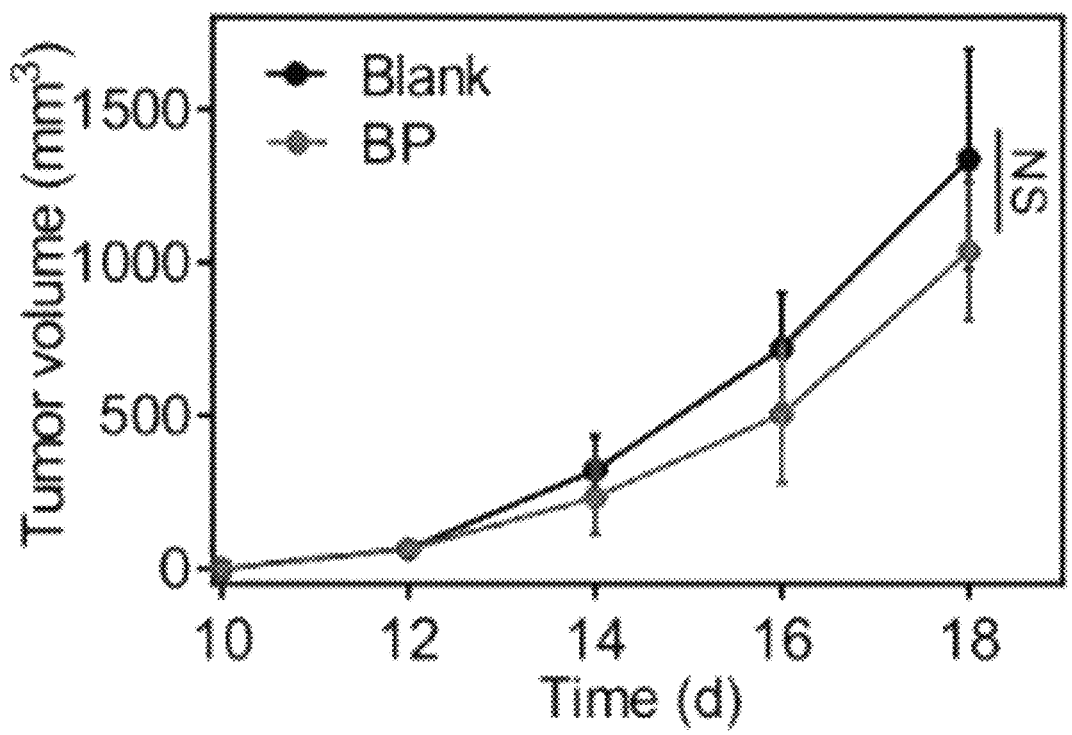
Figure 6J:
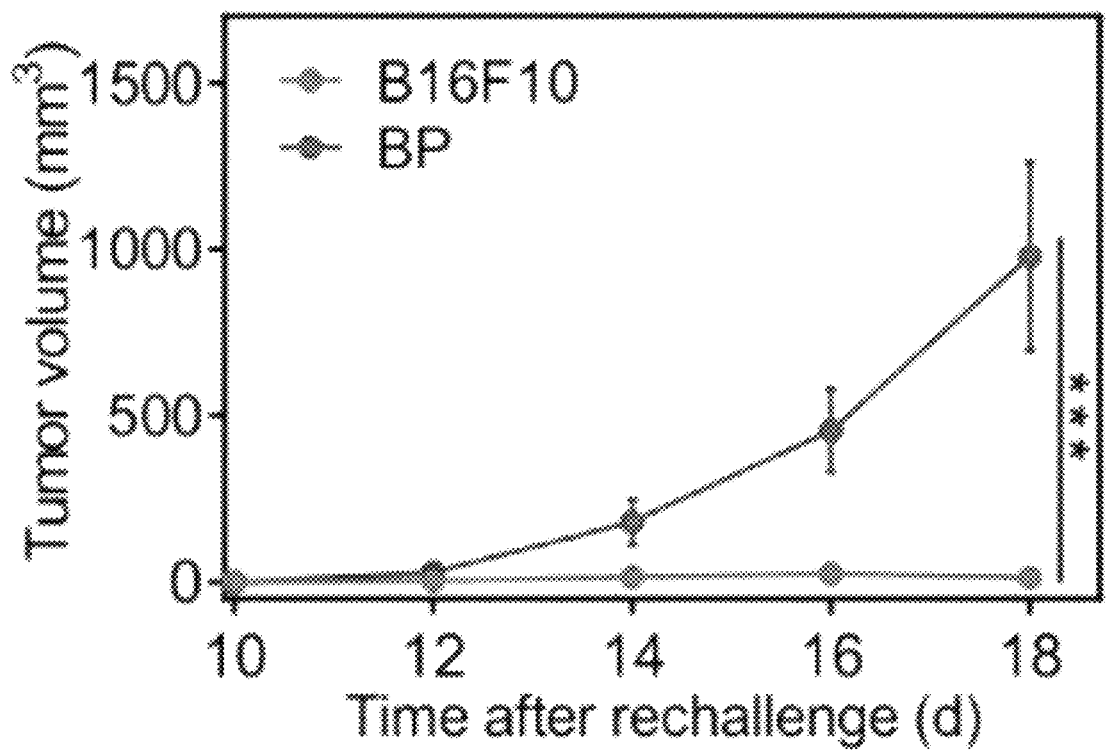

Example 4: The efficacy of photo-responsive MN applicators in distant tumors. It was further analyzed whether the local vaccination confers protection towards secondary tumors distant from the NIR and MN-treated site (FIG. 6A). Local NIR irradiation and MN treatment were performed only on the left-side tumor in B16F10 mice bearing bilateral tumors. Right-sided tumor was not injected and was shielded from light (FIG. 6B). We observed that the tumor sizes and bioluminescence signals decreased significantly on both sides of the mice that had the combined vaccination (FIGS. 6C-6G). Meanwhile, remarkable increase of activated DCs in the regional lymph node (FIG. 5B), and enhanced cytotoxic responses to B16F10 cells of the splenocytes in vitro (FIG. 5E) all indicated that systemic antitumor effect could be achieved by the transdermal immunotherapy. This effect was parallel by 5-fold increases in CD8+ T cell infiltration compared to control, which was consistent with the role of immune cells for antitumor efficacy (FIG. 6D). Distant metastases were not observed in the lungs of the mice with combinational treatment (FIG. 29). Body weight measurements indicated that the treated mice gained weight within the normal ranges (FIG. 6H). When the mice were vaccinated with tumor lysate of a different melanoma cell type (BRAFV600EPTEN−/−Duke-clone 6 cell line (BP)), minimal changes in the B16F10 tumor growth were observed (FIG. 6I) indicating the specificity of the immunological memory. Similarly, when vaccinated mice were re-challenged with B16F10 cells or BP cells, tumor protection was observed only in mice challenged with B16F10 (FIGS. 6J-6K and FIG. 30).

Figure 7A:
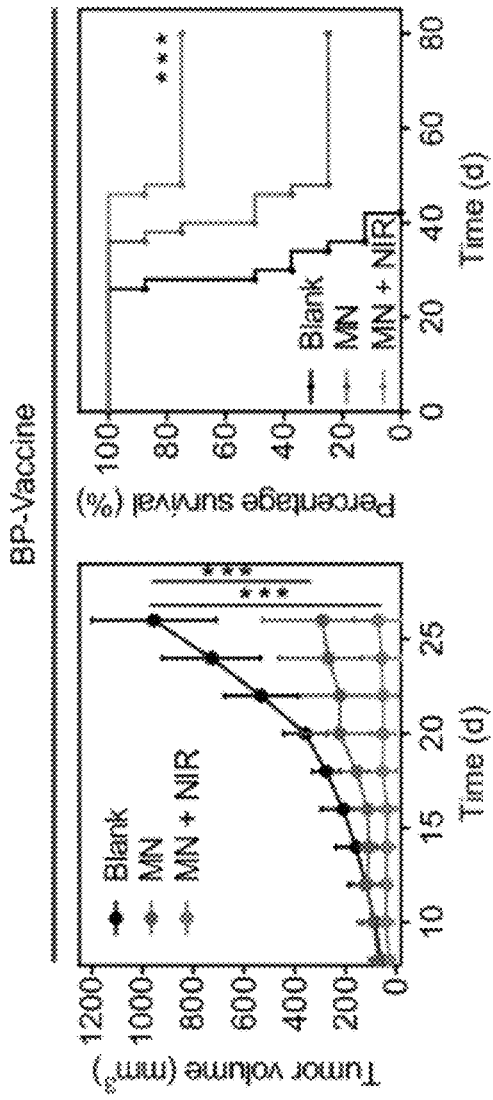
FIGS. 7A-7D demonstrate antitumor effects of local cancer immunotherapy treatment in various tumor models. (A) Average tumor growth and Kaplan-Meier survival rate of vaccinated C57BL/6J mice after BP tumor cell challenge. Mice were pretreated with blank MN (blank), MN loaded with BP tumor lysate and melanin (MN) or loaded MN combined with NIR irradiation (MN+NIR). (B) Average tumor growth and Kaplan-Meier survival rate of vaccinated BALB/cJ mice after 4T1 tumor cell challenge. Mice were pretreated with blank MN (blank), MN loaded with 4T1 tumor lysate and melanin (MN) or loaded MN combined with NIR irradiation (MN+NIR). (C) Average tumor growth and Kaplan-Meier survival rate of C57BL/6J mice bearing established BP tumors. Mice were treated with blank MN (blank), MN loaded with BP tumor lysate and melanin (MN) or loaded MN combined with NIR irradiation (MN+NIR). (D) Average tumor growth and Kaplan-Meier survival rate of BALB/cJ mice bearing established 4T1 tumors. Mice were treated with blank MN (blank), MN loaded with 4T1 tumor lysate and melanin (MN) or loaded MN combined with NIR irradiation (MN+NIR). Data points represent mean±SD (n=8). Error bars indicate SD. Statistical significance was calculated by the Student t-test and Log-rank test (* P<0.05;  P<0.01; * P<0.001).
Figure 7B:
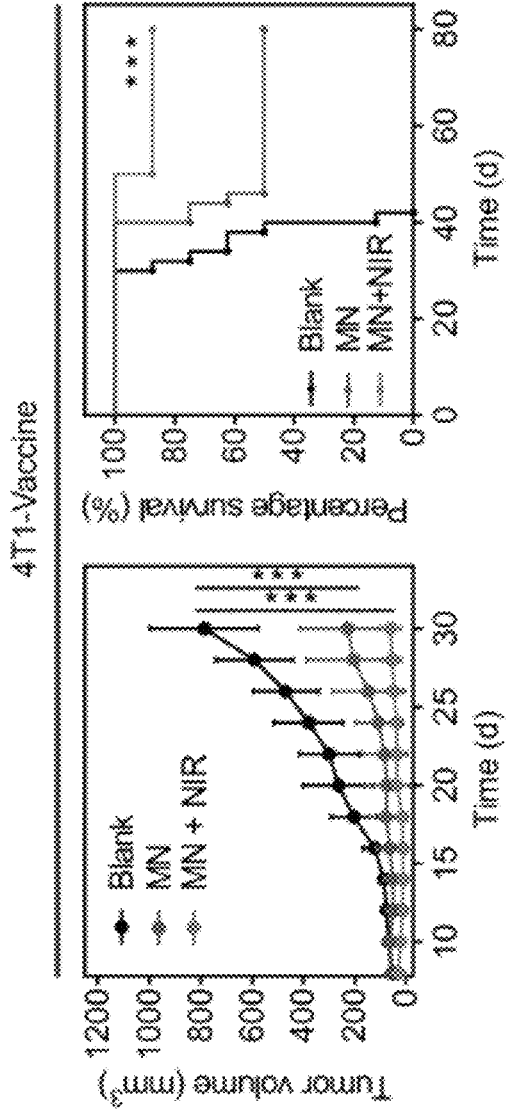
Figure 7C:
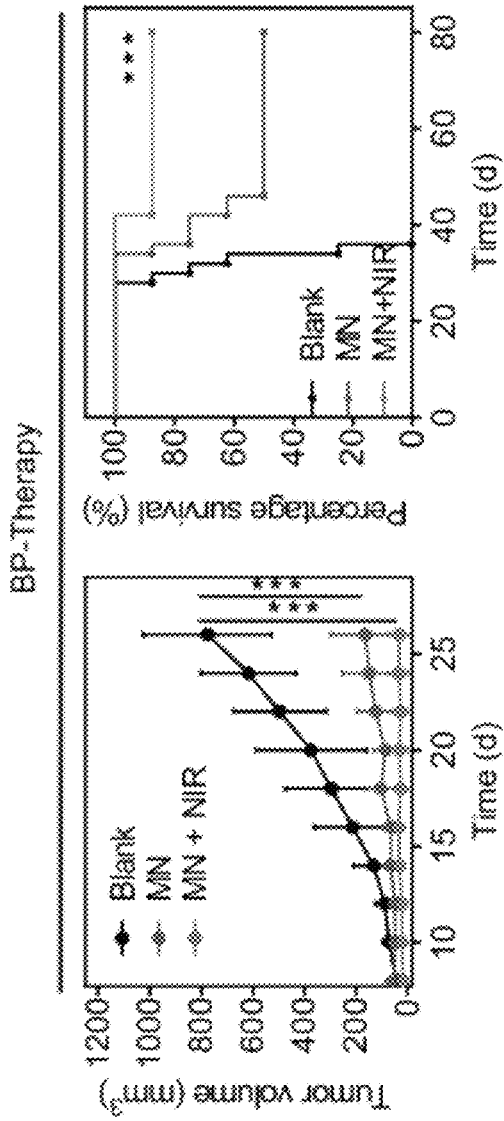
Figure 7D:
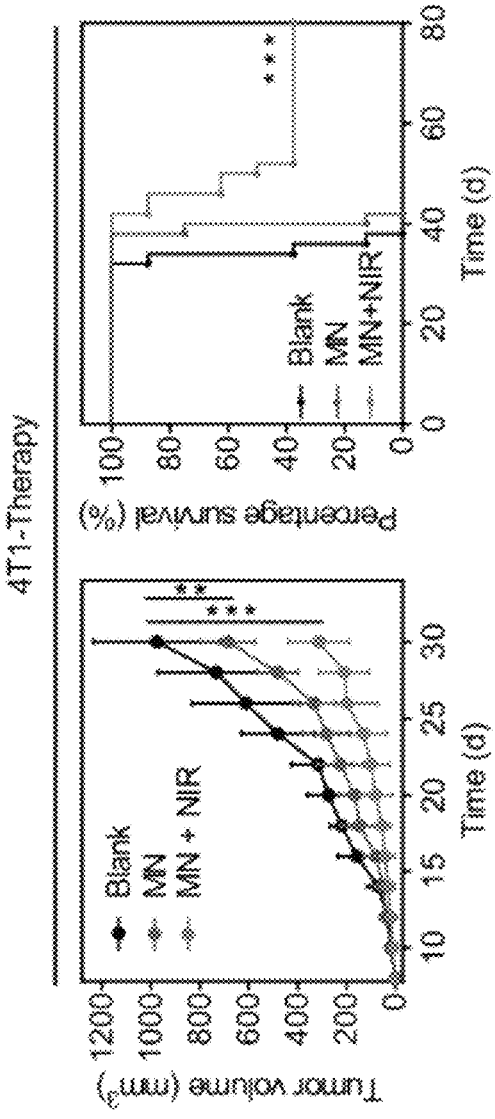

Example 5: The efficacy of photo-responsive MN applicators in other tumor models. To demonstrate that the potency of proposed vaccination is not limited to the B16 melanoma model in which there is an upregulation of the melanogenesis, a BRAFV600E mutated BP melanoma in C57BL/6J mice and a triple-negative breast cancer 4T1 carcinoma tumor in BALB/cJ mice were utilized. Studies of MN loaded with synthetic melanin (with the same amount of pigment as quantified by spectrophotometry; Table 1) and tumor lysate showed similar hyperthermic effect and significantly enhanced immune responses with combined vaccination (FIG. 31). Tumor regression and long-term survival were also achieved. Importantly, vaccination with the combined approach rendered 75% and 87% of mice resistant to BP and 4T1 engraftment, respectively (FIGS. 7A-7B and FIG. 32). In the tumor-bearing mice, MN and NIR treatment induced complete remissions in 87% and 37% of mice engrafted with BP and 4T1 cells, respectively (FIGS. 7C-7D and FIG. 32). Analysis of the local HSP70 expression showed 2.5-fold increase in BP and 4-fold in 4T1 models upon combined vaccination compared to the MN alone (FIG. 33). Production of pro-inflammatory cytokines was also induced with the combined treatment resulting in enhanced DC activation (FIG. 34 and FIG. 35). Treatments were well tolerated and did not cause weight loss or clinical signs of distant metastasis (FIG. 36 and FIG. 37).

Materials and Methods

Study Design. The present disclosure assessed the effect of a melanin-mediated transdermal applicator patch on cancer vaccine-based immunotherapy. B16F10 whole tumor lysate containing melanin was integrated into a microneedle applicator patch that allows controlled release of the cancer vaccine. Upon NIR light irradiation on the applicator patch, the local heating effect on boosting immune responses was evaluated. Mice subjects were purchased from Jackson Laboratories (USA), weighed and randomly divided into different experimental groups. The numbers of sampling and experimental replicates were included in each Figure legend.

Preparation and characterization of MNs. All MNs were prepared using silicone molds with arrays of conical holes machined by laser ablation (Blueacre Technology Ltd.). Each MN had a 300 µm by 300 µm round base tapering to a height of 800 µm with a tip radius of around 5 µm. MNs were arranged in a 15×15 array with 600 µm center-to-center spacing. GM-CSF solution (0.1 mg/mL, 10 µL final volume) was directly deposited by pipetting onto each silicone micromold surface followed by vacuum (600 mmHg) condition for 5 min to allow the solution flowing into the cavities. After that, 0.2 mL 4.0 wt % methacrylated hyaluronic acid solution mixed with N,N'-methylenebisacrylamide (2.0 wt %) and photoinitiator (Irgacure 2959; 0.05 wt %) were directly deposited by pipetting onto each silicone micromold surface followed by vacuum (600 mmHg) condition for 5 min. GM-CSF layer was crosslinked via ultraviolet irradiation (wavelength: 365 nm) for 10 sec and a piece of 4 cm×9 cm silver adhesive tape was applied around the 2 cm×2 cm micromold baseplate. Three mL of homogenized B16F10 tumor lysate (containing 1.5 mg of extracted tumor lysate proteins) in 4.0 wt % mixed methacrylated hyaluronic acid solution was added to the prepared micromold reservoir. Hyaluronic acid solution was used with different concentrations of tumor protein, ranging from about 0.25 mg/mL, about 0.5 mg/mL to about 1.0 mg/mL. Protein concentration was quantified by measuring extracted protein content in the tumor lysate supernatant using T-PER extraction reagent and Bradford assay before the MN fabrication. For the BP or 4T1 tumor lysate loaded-MNs, 50 µg melanin was dissolved in 4.0 wt % mixed methacrylated hyaluronic acid solution with tumor lysate (containing 1.5 mg of extract tumor lysate proteins, 3.0 mL final volume) to fabricate the MN matrix. For the blank MNs without tumor lysate, mixed methacrylated hyaluronic acid was used without the tumor lysate. For the melanin-loaded MNs, 50 µg melanin was dissolved in 4.0 wt % mixed methacrylated hyaluronic acid solution to fabricate the MN matrix. The stock 100 mg/mL melanin solution was prepared by dissolving melanin in 1.0 M sodium hydroxide and heating to 99° C. for 10 min. Final formulation was dried at 25° C. in a vacuum desiccator overnight. After desiccation was completed, needle arrays were carefully separated from the silicone molds and cross-linked via ultraviolet irradiation. The needle base was tailored into a square shape. Fluorescent MNs were fabricated with phalloidin labeled tumor lysate and Rhodamine B or Cy5.5 labeled hyaluronic acid. Morphology of MNs was characterized on a FEI Verios 460L field-emission scanning electron microscope operating at 20 kV after sputter coating with gold/palladium at the Analytical Instrumentation Facility. Cross-sections of MNs were obtained by cutting 5 µm slides using Thermo Scientific HN 525NX Cryostat and stained with Alexa Fluor 488 or 660-phalloidin and Hoechst. Fluorescence images of MNs were taken by the Olympus IX70 multi-parameter fluorescence microscope.

NIR-responsive property of MN. To evaluate the property of the photo-responsive MN applicator in response to NIR light irradiation, samples were irradiated with 808 nm NIR laser light. The diode infrared laser module (Opto Engine LLC, MDL-N-808) was approved by laser safety officer of the North Carolina State University (NC State) Environmental Health and Safety Center. The MN applicators were placed on a piece of white paper with the needle tips facing down. The laser wire was fixed in place using a plate stand with a support rod and a clamp. The distance between the applicator and spot light was fixed at 10 cm, and the spot size was ~1 $cm^2$. The output energy of the diode infrared laser module was adjusted within 1.0 W, and led to the intensity per unit area ($E=I/d^2$) of 1.0 watt/$cm^2$ (at 808 nm) (W/$cm^2$). The NIR light was irradiated continuously or intermittently as needed. Surface temperature changes of the MN applicator backing were recorded and the highest temperature was controlled below 42° C. in real time using a thermal imager (FLIR E4) and a non-contact infrared thermometer gun (Leegoal). For intermittent irradiation, the MNs were repeatedly exposed to the 1.0 W/$cm^2$ laser and the local temperature reached approximately 42° C. for 1 min. Subsequently, the laser was turned off for 1 min. This cycle was repeated four times to assess the responsive behavior of MN-array applicator under repeated NIR irradiation. For the continuous irradiation, samples with different parameters were tested. The effect of melanin content on the light responsive behavior was tested on MNs loaded with tumor lysate of difference protein concentration or blank MN with hyaluronic acid. Quantitative surface temperature changes of the representative MNs were recorded under continuous NIR irradiation at 1.0 W/$cm^2$. In a separate experiment, the laser power flux was controlled. During continuous NIR exposure for 2 min, the maximal temperature of the MN surface was recorded and plotted. The effect of MN backing thickness on the light responsive behavior was tested on MNs with continuous NIR irradiation at 1.0 W/$cm^2$. The thickness of the MN applicator was measured with an average value of 181 µm and a standard deviation of 12.5 µm using a digimatic indicator (Mitutoyo Corp. ID-C112E Series 543). MN applicator samples with different backing thickness were used: 169 µm, 175 µm, 179 µm, 181 µm and 202 µm.

In vitro DC activation. Bone marrow was collected by flushing the femur and tibia with complete RPMI 1640 medium containing 10% fetal bovine growth serum. After lysis of red blood (Lysates solution, Cwbiotech), 1×$10^6$ bone marrow cells were seeded in six well culture dishes with 3.0 mL of the culture medium containing 20 ng/mL GM-CSF and 50 µM Beta Mercaptoethanol (Biorad, Hercules, CA, USA). On day 3, an additional 4.0 mL of the same medium with GM-CSF was added into the plates. On day 6, half of the culture supernatant was collected and centrifuged. Cells were resuspended in RPMI medium and added back into the original plates. On day 7, non-adherent cells were collected and used as bone marrow derived DCs for further research use. Another murine DC cell line, JAWS II cells were cultured in Minimum Essential Medium Eagle Alpha Modification (MEM, Sigma) supplied with 5 ng/mL GM-CSF. DCs were left unstimulated or stimulated for 12 hrs with 100 µg/mL of blank MN or tumor lysate-loaded MN release medium or 100 ng/mL lipopolysaccharide (LPS). Following the stimulation, the cells were exposed to 1.0 $W/cm^2$ NIR irradiation at a distance of 10 cm for 0, 5, 10, 15, 20 min respectively. After cell incubation for 4 hrs, the supernatants were collected and measured by IL-12 p70 Mouse ELISA Kit (Thermo Fisher, MC0121). The cells were washed and stained with live-dead assay (Thermo Fisher, L3224), CD80+ and CD86+ maturation marker-specific antibodies and subsequently analyzed by the confocal microscopy and flow cytometer. Both bone marrow-derived DC cells and JAWS II cell line were used for characterization of DC activation. The live/dead assay imaging data was obtained from the JAWS II cell line.

Mice and in vivo tumor models. Female C57BL/6J mice, BALB/cJ mice, CD11c-diphtheria toxin receptor (DTR) transgenic mice (B6.FVB-Tg(Itgax-DTR/EGFP)57Lan/J; stock no. 004509), Rag1−/− knockout mice (B6.12957-Rag1tm1Mom/J; stock no. 002216) were purchased from the Jackson Lab. Mice were weighed and randomly divided into different groups. On day 0, healthy mice were treated with MNs loaded with tumor lysates and GM-CSF, blank MNs loaded with synthetic melanin without tumor lysate or blank MNs containing hyaluronic acid only (blank). MN applicators were applied into the skin of the caudal dorsal area for approximately 10 min and further fixed using Skin Affix surgical adhesive (Medline Industries, Inc.). Following injection of the MNs, NIR irradiation was performed on the localized MN region for 10 min each day for five successive days after immunization (MN+NIR). The diode infrared laser module at 808 nm (Opto Engine LLC, MDL-N-808) was approved by laser safety officer of the NC State Environmental Health and Safety Center. Mice in the control groups were either treated with vaccine MNs without NIR irradiation (MN), blank MNs loaded with synthetic melanin without tumor lysate with NIR irradiation (melanin) or blank MNs containing hyaluronic acid only with NIR irradiation (blank). Surface temperature changes of the regional skin were recorded and controlled below 42° C. in real time using a thermal imager (FLIR E4) and a non-contact infrared thermometer gun (Leegoal). On day 10, $1\times10^6$ B16F10 tumor cell lines in 25 µL PBS were subcutaneously transplanted into the flank of the C57BL/6J mice, CD11c-DTR transgenic mice and Rag1−/− knockout mice. Tumor-free mice were re-challenged with $1\times10^6$ B16F10 tumor cells in 25 µL PBS 80 days after the first tumor inoculation. For the depletion antibody study, specific T cell, B cell and NK cell populations were depleted in mice models. Mice were i.p. given 200 µg of antibody purified from mouse thymus or spleen dissolved in 200 µL of PBS. Antibodies against CD4 (Biolegend, LEAF 100435) and CD8 (Biolegend, LEAF 100735), CD19 (Biolegend, LEAF 152402) and NK-1.1 (Biolegend, LEAF 108712) were administered twice weekly for three weeks, starting one week before the tumor inoculation. Depletions were confirmed by flow cytometry of splenic suspension. For another melanoma model, $1\times10^6$ BP tumor cells in 25 µL PBS were subcutaneously transplanted into the flank of the C57BL/6J mice. For the carcinoma tumor model, $1\times10^6$ 4T1 tumor cells in 25 µL PBS were subcutaneously transplanted into the flank of the BALB/cJ mice. For experimental metastasis model, $1\times10^5$ tumor cells were intravenously infused into mice via the tail vein. In another set of experiments, tumor cells were subcutaneously transplanted into the flank of the mice on day 0. The tumor-bearing mice were weighed and randomly divided into four groups when the tumor volume reached around 50 $mm^3$ on day 3. After that, the mice were peritumorally administrated with sterile MN loaded with tumor lysate and GM-CSF (MN) or blank MN containing hyaluronic acid only (blank). After that, NIR light was irradiated on the MN applicator for 10 min during the following five days from day 3 to day 7. Tumor growth was measured by a digital caliper or monitored by bioluminescence signals of luciferase-tagged cells. The tumor volume ($mm^3$) was calculated as ½×long diameter×(short diameter).

To assess potential toxicity, mice were monitored daily for weight loss. H&E staining was performed on the organs collected from the mice following the standard procedure (Histology Laboratory at NC State College of Veterinary Medicine). Lungs were excised and macroscopically visible metastases were counted. The resected primary tumors were stored at −20° C. for immunofluorescence staining or fixed in 4% paraformaldehyde for subsequent analysis.

Identification of DC subsets, T cells and cytokines. Antibodies used was purchased from Thermo Fisher Scientific and Biolegend Inc. Staining antibodies, including CD3 (Thermo Fisher Scientific, A18644), CD4 (Thermo Fisher Scientific, A18667), CD8 (Thermo Fisher Scientific, A18609), CD11c (Biolegend, 117309), CD49b (Biolegend, 108909), CD80 (Biolegend, 104707), CD86 (Biolegend, 105007), PIR-AB (gp91, Biolegend, 144103), Tetramer (MBL International, H-2Db gp100 EGSRNQDWL-P) and fluorogenic CellROX™ Deep Red Reagent (Biolegend, C10422) were used for FACS and were analyzed following manufacturers' instructions. Organs (skin, tumor, lymph node, spleen) were harvested and minced into 2-4 mm pieces using scissors or scalpel blade. A single cell suspension was prepared in the Cell Staining Buffer (BioLegend, 420201). CellROX Reagents at predetermined optimum concentrations were added to the cells and incubated on ice for 20-30 min in the dark for ROS detection. The relevant tetramer PE was stained at room temperature for 30 min in dark before additional staining with appropriately conjugated fluorescent antibodies. Stained cells were analyzed on a Calibur FACS instrument (BD) and were analyzed using flowJo software. To determine the concentration of different cytokines at the MN vaccine site, the applicator and adjacent tissue were excised and digested with tissue protein extraction reagent (Pierce). Cytokine concentrations in the extracted applicator were analyzed with a BioLegend's LEGENDplex™ bead-based immunoassays, according to the manufacturer's instructions.

Statistical analysis. Statistical analysis was evaluated using GraphPad Prism (6.0). Statistical analysis were performed with the paired the Student t-test and ANOVA. P values for Kaplan-Meier curves were calculated with Log-rank test. P values of 0.05 or less were considered significant.

Study Approval. All mouse studies were performed following animal protocols approved by the Institutional Animal Care and Use Committee at North Carolina State University and the University of North Carolina at Chapel Hill.

Cell culture. The mouse melanoma cell line B16F10 and mouse mammary carcinoma cell line 4T1 were purchased from the American Type Culture Collection. B16F10-luc and BRAFV600EPTEN−/−(BP) (generated by Dr. Brent A. Hanks's lab at Duke) cells were obtained from Dr. Leaf Huang at University of North Carolina at Chapel Hill. B16F10 cells were maintained in the Dulbecco's Modified Eagle Medium (DMEM, Gibco, Invitrogen) supplemented with 10% fetal bovine serum (Invitrogen, Carlsbad, CA), 100 U/mL penicillin (Invitrogen) and 100 U/mL streptomycin (Invitrogen). 4T1 and BP cells were maintained in the Roswell Park Memorial Institute (RPMI) 1640 Medium (Gibco, Invitrogen) supplemented with 10% fetal bovine serum (Invitrogen, Carlsbad, CA), 100 U/mL penicillin (Invitrogen) and 100 U/mL streptomycin (Invitrogen). Cells were cultured in an incubator (Thermo Scientific) at 37° C. under an atmosphere of 5% $CO_2$ and 90% relative humidity and were sub-cultivated approximately every 3 days at 80% confluence using 0.25 wt % trypsin at a split ratio of 1:3.

Protein and melanin quantification of tumor lysates. Primary tumors were collected from the B16F10 melanoma-bearing mice. For the quantification of tumor lysate protein, 3 mL T-PER Tissue Protein Extraction Reagent was added to 1.5 g tumor tissue and homogenized using sonication. After incubation on ice for 2 hrs, lysates were centrifuged for 20 min at 10,000×g at 4° C. to pellet tissue debris and the protein concentration of the resulting supernatants was determined using a Coomassie Plus™ (Bradford) Assay Kit. For the quantification of melanin, homogenized tumor tissue was resuspended in 1 M sodium hydroxide and heated to 99° C. for 10 min. Melanin concentration was determined by measuring the absorbance at 475 nm and calculated based on a standard curve. For preparation of the microneedles (MNs), 3 mL phosphate-buffered saline (PBS) medium buffer was added to 1.5 g tumor tissue and homogenized by sonication.

Mechanical strength test. Mechanical strength of microneedles with a stress-strain gauge was determined by pressing a stainless steel plate against MNs on an MTS 30G tensile testing machine. Initial gauge was 2.00 mm between the tips of MN and the plate, with 10.00 N as the load cell capacity. Speed of the plate approaching MNs was set as 0.1 mm/s. Failure force of the MN was recorded as the force at which the needle began to buckle.

Skin penetration test. To evaluate the skin penetrating capacity of MNs, they were inserted into the skin of mice for 10 min. Mice were euthanized and skin samples were stained with trypan blue for 10 min before imaging by an optical microscopy (Leica EZ4 D stereomicroscope). In separate experiments, skin samples were stained with hematoxylin and eosin (H&E) (Histology Laboratory at NC State College of Veterinary Medicine).

Granulocyte-macrophage colony-stimulating factor (GM-CSF) release profile. The amount of GM-CSF released from MNs was detected by ELISA (eBioscience Mouse GM-CSF ELISA Kit) according to the manufacturer's protocol. The release of GM-CSF from MNs was monitored by immersing the tips of MNs into PBS medium buffer in 37° C. under moderate shaking. Near infrared (NIR) irradiation was performed on the MNs for 10 min per day for 3 days. At pre-determined time points, 100 μL of the medium was collected for analysis and additional 100 μL of the fresh medium was added. The absorption intensity of GM-CSF was determined at 450 nm by a microplate reader (Infinite M200 PRO, Tecan). The concentration of tumor lysate proteins were also analyzed by Bradford assay at the same time. The percentage of bioactive GM-CSF was assessed by an in vitro bioactivity assay and calculated by normalizing the amount of GM-CSF bioactivity to the amount of GM-CSF protein detected by ELISA. The bioactivity assay utilized the bone marrow derived dendritic cells (DCs) isolated from C57BL/6J mice (female, aged 6-8 weeks; Jackson Laboratories). 10% v/v of AlamarBlue reagent was added to each cell culture well, and after incubation for 4 hrs at 37° C., plates were read at the absorbance of 490 nm. All standards and samples were normalized to the blank controls, and the bioactivity of the experimental samples was determined relative to the standard curve.

Cytotoxicity study. Cytotoxicity studies toward blank MN formulations with various dissolved concentrations were performed using B16F10 cells. Cells were seeded into 96-well plates at a density of $5 \times 10^3$ cells per well and cultivated in 100 μL of DMEM (25 mM glucose) with 10% FBS, 1× penicillin-streptomycin (Pen-Strep), 1× L-Glutamine and 2.5 μL of Beta Mercaptoethanol per 500 mL media. Plates were then incubated in 5% $CO_2$ at 37° C. for 12 hrs to reach 70-80% confluence before adding serial dilutions of the released media incubated with MN solution. After incubation with samples for 24 hrs, cells were washed with PBS solution and incubated with 100 μL of fresh FBS-free DMEM and 20 μL of freshly prepared 3-(4,5-dimethylthiazol-2-yl)-2,5-diphenyltetrazolium bromide solution (MTT solution, 5.0 mg/mL). Plates were incubated for additional 4 hrs at 37° C. in the dark. Afterwards, the solution was carefully removed and 100 μL dimethyl sulfoxide was added. Absorbance of the plates was read at 590 nm and a reference wavelength of 630 nm using a microplate reader (Infinite M200 Pro, Tecan, Morrisville, NC, USA) within 10 min.

In vivo bioluminescence and imaging. Bioluminescence images were collected with a Xenogen IVIS Spectrum Imaging System. Living Image software (Xenogen) was used to acquire the data 10 min after intraperitoneal injection of D-luciferin (Pierce) in Dulbecco's phosphate-buffered saline (DPBS) (15 mg/mL) into animals (10 μL/g of body weight).

Confocal microscopy. Regional skin and tumors were dissected and fixed in 4% paraformaldehyde at 4° C. and then embedded in OCT compound (Sakura Finetek) and flash-frozen in an isopentane bath on dry ice. Frozen samples were sectioned (5 μm thickness), mounted on microscope slides, and stored at −20° C. For staining of CD3 (Thermo Fisher Scientific, A18644), CD4 (Thermo Fisher Scientific, A18667), CD8 (Thermo Fisher Scientific, Cat A18609), CD11c (Biolegend, 117309), CD49b (Biolegend, 108909), heat shock proteins 70 (HSP70) (Abcam, ab2787) and HSP90 (Abcam, ab1429) by immunofluorescence, the slides were washed twice, permeabilized for 30 min using a 0.1% Triton X100 solution, and subsequently blocked for one hour using a 1% bovine serum albumin (BSA) solution. After blocking, primary monoclonal antibody at 1/200 dilution was applied overnight at 4° C., followed by washing and incubation with secondary antibody at 1/400 dilution. Secondary antibodies were added to some samples, including Goat anti-Rat IgG Secondary Antibody (Thermo Fisher A18866), Rabbit anti-Rat IgG (H+L) Secondary Antibody (Thermo Fisher Scientific, A18920). Slides were washed thrice, applied with Hoechst 33342 or 4',6-Diamidino-2-Phenylindole, Dihydrochloride (DAPI) to stain the cell nucleus and covered with coverslips. For the terminal deoxynucleotidyl transferase dUTP nick end labeling (TUNEL) apoptosis staining, the fixed tumor sections were stained by the In Situ Cell Death Detection Kit (Roche Applied Science) according to the manufacturer's protocol.

Hoechst 33342 was used for nuclear staining. Samples were imaged using the Olympus IX70 multi-parameter fluorescence microscope and a confocal microscope (Zeiss). Images were processed using the ImageJ software.

Isolation of tumor-infiltrating cells and lymphoid tissue cells. B16F10 tumor cell samples were isolated by grinding tumors through 40 μm nylon cell strainer (Corning) in RPMI. BP and 4T1 tumor samples were minced with scissors before incubation with trypsin/EDTA (0.25%/0.1%) for 20 min. Tumor cells were homogenized by repeated pipetting and filtered through a 40 μm cell strainer in RPMI to generate single-cell suspensions. Cell suspensions were washed once with complete RPMI. Lymphoid tissue cells were isolated from mouse skin into single cell suspension as described. All samples were re-suspended in fluorescence-activated cell sorting (FACS) buffer (PBS/0.5% albumin) before testing.

Cytotoxic T lymphocyte activity. Splenocytes harvested from mice were stimulated in vitro with tumor lysate. Cells were washed through the strainer 3 times with excess PBS and then cultured together with B16F10 target cells in 96-well culture plates at the effective target cell ratio of 500:1. After 24 hrs, the supernatants were collected to detect the lactate dehydrogenase (LDH) leakage level with a non-radioactive cytotoxicity assay (Thermo Scientific), which indicated the level of specific lysis of target cells by effective cells. The percentage of specific lysis was calculated according to % specific lysis=((experimental LDH release−effective cell LDH release)/(maximum LDH release−spontaneous LDH release))×100%.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

For reasons of completeness, various aspects of the invention are set out in the following numbered clauses, as well as the following claims:

Clause 1. A photo-responsive dermal applicator for use in photoimmunotherapy, the dermal applicator comprising a transdermal microneedle array comprising a plurality of microneedles, each microneedle comprising a base portion and a tip portion, an immunogenic composition comprising at least one tumor antigen, and a photo-sensitive biological pigment.

Clause 2. The dermal applicator of clause 1, wherein the immunogenic composition and the biological pigment are encapsulated within the microneedle array using a polymeric matrix comprising at least one of glycosaminoglycans, polysulfated glycosaminoglycans, glucosoglycans, polysulfated glucosoglycans, glucosaminoglycans, mucopolysaccharides, carboxymethylcellulose (CMC), poly(lactide-co-glycolide) (PLGA), polyvinylpyrrolidone (PVP), polyvinyl alcohol (PVA), poly(acrylic acid) (PAA), poly-L-lactic acid (PLA), maltose, chitosan, alginate, and derivatives and combinations thereof.

Clause 3. The dermal applicator of clause 1 or 2, wherein the polymeric matrix comprises hyaluronic acid.

Clause 4. The dermal applicator of clauses 1 to 3, wherein the at least one tumor antigen is derived from inactivated tumor lysate or a neoantigen.

Clause 5. The dermal applicator of clauses 1 to 4, wherein the at least one tumor antigen is derived from melanoma, Leukemia, breast cancer, lung cancer, bladder cancer, brain cancer, cervical cancer, ovarian cancer, colorectal cancer, and any related cancer.

Clause 6. The dermal applicator of clauses 1 to 4, wherein the at least one tumor antigen is derived from a B16F10 melanoma, a $BRAF^{v600E}$ melanoma, or 4T1 breast tumor.

Clause 7. The dermal applicator of clauses 1 to 5, wherein the at least one tumor antigen comprises an immunogenic epitope from the subject.

Clause 8. The dermal applicator of clauses 1 to 7, wherein the photo-sensitive biological pigment is at least one of a melanin, a carotenoid, a xanthophyll, a bilirubin, or a combination thereof.

Clause 9. The dermal applicator of clauses 1 to 8, wherein the immunogenic composition further comprises an immunostimulant.

Clause 10. The dermal applicator of clause 9, wherein the immunostimulant comprises at least one of granulocyte-macrophage colony-stimulating factor (GM-CSF), a CpG nucleotide, interleukin (IL)-7, IL-15, and combinations thereof, and wherein the immunostimulant is capable of stimulating an immune cell.

Clause 11. The dermal applicator of clause 9, wherein the immunostimulant comprises at least one immune checkpoint inhibitor.

Clause 12. The dermal applicator of clauses 1 to 11, wherein the immunogenic composition and the photo-sensitive biological pigment are encapsulated within the base portion of the plurality of microneedles, and wherein the immunostimulant is encapsulated within the tip portion of the plurality of microneedles, the tip portion distal to the base portion.

Clause 13. The dermal applicator of clause 12, wherein the immunostimulant is encapsulated within the tip portion of the plurality of microneedles by crosslinking methacrylated hyaluronic acid.

Clause 14. The dermal applicator of clauses 1 to 13, further comprising a means for delivering light energy to the applicator to stimulate an immune response in a subject.

Clause 15. The dermal applicator of clause 14, wherein the light energy comprises near infrared (NIR) light.

Clause 16. A method of treating a subject with a tumor, the method comprising contacting an area of the subject's skin with the photo-responsive dermal applicator of clause 1, and delivering light energy to the dermal applicator; wherein the light energy transforms into heat and further stimulates an immune response in the subject against the tumor.

Clause 17. The method of clause 16, wherein the delivery of light energy to the dermal applicator comprises delivering near infrared (NIR) light, UV light, or light with wavelengths at from 10 nm to about 1000 nm.

Clause 18. The method of clause 16 or 17, wherein the delivery of light energy to the dermal applicator comprises delivering NIR light for about 5 minutes to about 20 minutes.

Clause 19. The method of clauses 16 to 18, wherein the delivery of light energy to the dermal applicator comprises delivering NIR light at least once per day for about one day to about seven consecutive days.

Clause 20. The method of clauses 16 to 19, wherein the at least one tumor antigen is derived from inactivated tumor lysate or a neoantigen.

Clause 21. The method of clauses 16 to 19, wherein the at least one tumor antigen is derived from a melanoma, Leukemia, breast cancer, lung cancer, bladder cancer, brain cancer, cervical cancer, ovarian cancer, colorectal cancer, and any related cancer.

Clause 22. The method of clauses 16 to 21, wherein the photo-sensitive biological pigment comprises melanin, and wherein delivering NIR light to the dermal applicator stimulates the melanin to create a hyperthermic microenvironment.

Clause 23. The method of clause 22, wherein the temperature of the hyperthermic microenvironment is from about 35° C. to about 45° C.

Clause 24. The method of clauses 16 to 23, wherein the immunogenic composition further comprises an immunostimulant.

Clause 25. The method of clause 24, wherein the immunostimulant comprises at least one of granulocyte-macrophage colony-stimulating factor (GM-CSF), a CpG nucleotide, interleukin (IL)-7, IL-15, and combinations thereof, and wherein the immunostimulant is capable of stimulating an immune cell.

Clause 26. The method of clause 24, wherein the immunostimulant comprises at least one immune checkpoint inhibitor.

Clause 27. A method of inhibiting tumor formation in a subject, the method comprising contacting an area of the subject's skin with the photo-responsive dermal applicator of clause 1, and delivering light energy to the dermal applicator, wherein the delivery of light energy to the dermal applicator stimulates an immune response in the subject against the tumor.

Clause 28. The method of clause 27, wherein the delivery of light energy to the dermal applicator comprises delivering near infrared (NIR) light, UV light, or light with wavelengths from about 10 nm to about 1000 nm.

Clause 29. The method of clause 27 or 28, wherein the delivery of light energy to the dermal applicator comprises delivering NIR light for about 5 minutes to about 20 minutes.

Clause 30. The method of clauses 27 to 29, wherein the delivery of light energy to the dermal applicator comprises delivering NIR light at least once per day for about one day to about seven consecutive days.

Clause 31. The method of clauses 27 to 30, wherein the at least one tumor antigen is derived from inactivated tumor lysate or a neoantigen.

Clause 32. The method of clauses 27 to 31, wherein the at least one tumor antigen is derived from a melanoma, Leukemia, breast cancer, lung cancer, bladder cancer, brain cancer, cervical cancer, ovarian cancer, colorectal cancer, and any related cancer.

Clause 33. The method of clauses 27 to 32, wherein the photo-sensitive biological pigment comprises melanin, and wherein delivering NIR light to the dermal applicator stimulates the melanin to create a hyperthermic microenvironment.

Clause 34. The method of clause 33, wherein the temperature of the hyperthermic microenvironment is from about 35° C. to about 45° C.

Clause 35. The method of clauses 27 to 34, wherein the immunogenic composition further comprises an immunostimulant.

Clause 36. The method of clause 35, wherein the immunostimulant comprises at least one of granulocyte-macrophage colony-stimulating factor (GM-CSF), a CpG nucleotide, interleukin (IL)-7, IL-15, and combinations thereof, and wherein the immunostimulant is capable of stimulating an immune cell.

Clause 37. The method of clause 36, wherein the immunostimulant comprises at least one immune checkpoint inhibitor.

What is claimed is:

1. A photo-responsive dermal applicator for use in photoimmunotherapy, the dermal applicator comprising:
    a transdermal microneedle array comprising a plurality of microneedles, each microneedle comprising a base portion and a tip portion, wherein the tip portion is distal to the base portion;
    an immunogenic composition comprising at least one tumor antigen;
    an immunostimulant; and
    a photo-sensitive biological pigment comprising melanin;
    wherein the immunogenic composition, the immunostimulant, and the photo-sensitive biological pigment are encapsulated within the transdermal microneedle array using a polymeric matrix comprising hyaluronic acid, wherein the immunogenic composition and the photo-sensitive biological pigment are encapsulated within the base portion of the plurality of microneedles, and wherein the immunostimulant is encapsulated within the tip portion of the plurality of microneedles.

2. The dermal applicator of claim 1, wherein the polymeric matrix further comprises at least one of glycosaminoglycans, polysulfated glycosaminoglycans, glucosoglycans, polysulfated glucosoglycans, glucosaminoglycans, mucopolysaccharides, carboxymethylcellulose (CMC), poly (lactide-co-glycolide) (PLGA), polyvinylpyrrolidone (PVP), polyvinyl alcohol (PVA), poly(acrylic acid) (PAA), poly-L-lactic acid (PLA), maltose, chitosan, alginate, and derivatives and combinations thereof.

3. The dermal applicator of claim 1, wherein the at least one tumor antigen is derived from inactivated tumor lysate or a neoantigen.

4. The dermal applicator of claim 1, wherein the at least one tumor antigen is derived from melanoma, Leukemia, breast cancer, lung cancer, bladder cancer, brain cancer, cervical cancer, ovarian cancer, or colorectal cancer.

5. The dermal applicator of claim 1, wherein the at least one tumor antigen is derived from a B16F10 melanoma, a BRAFv600E melanoma, or 4T1 breast tumor.

6. The dermal applicator of claim 1, wherein the at least one tumor antigen comprises an immunogenic epitope from a subject.

7. The dermal applicator of claim 1, wherein the photo-sensitive biological pigment further comprises a carotenoid, a xanthophyll, a bilirubin, or a combination thereof.

8. The dermal applicator of claim 1, wherein the immunostimulant comprises at least one of granulocyte-macrophage colony-stimulating factor (GM-CSF), a CpG nucleotide, interleukin (IL)-7, IL-15, or combinations thereof, and wherein the immunostimulant is capable of stimulating an immune cell.

9. The dermal applicator of claim 1, wherein the immunostimulant comprises at least one immune checkpoint inhibitor.

10. The dermal applicator of claim 1, wherein the immunostimulant is encapsulated within the tip portion of the plurality of microneedles by crosslinking methacrylated hyaluronic acid.

11. The dermal applicator of claim 1, further comprising a means for delivering light energy to the applicator to stimulate an immune response in a subject.

12. The dermal applicator of claim 11, wherein the light energy comprises near infrared (NIR) light.

13. A method of treating a subject with a tumor, the method comprising:
contacting an area of the subject's skin with the photo-responsive dermal applicator of claim 1, and delivering light energy to the dermal applicator;
wherein the delivery of light energy to the dermal applicator stimulates an immune response in the subject against the tumor.

14. The method of claim 13, wherein the delivery of light energy to the dermal applicator comprises delivering NIR light for about 5 minutes to about 20 minutes at least once per day for about one day to about seven consecutive days.

15. The method of claim 13, wherein the at least one tumor antigen is derived from a melanoma, Leukemia, breast cancer, lung cancer, bladder cancer, brain cancer, cervical cancer, ovarian cancer, or colorectal cancer.

16. The method of claim 13, wherein delivering NIR light to the dermal applicator stimulates the melanin to create a hyperthermic microenvironment.

17. The method of claim 13, wherein the immunostimulant comprises at least one of granulocyte-macrophage colony-stimulating factor (GM-CSF), a CpG nucleotide, interleukin (IL)-7, IL-15, or combinations thereof, and wherein the immunostimulant is capable of stimulating an immune cell.

* * * * *